US012285331B2

(12) United States Patent
Johnson et al.

(10) Patent No.: US 12,285,331 B2
(45) Date of Patent: Apr. 29, 2025

(54) SYSTEMS, DEVICES, AND METHODS RELATING TO THE MANUFACTURE OF IMPLANTABLE PROSTHETIC VALVES

(71) Applicants: Foldax, Inc., Salt Lake City, UT (US); California Institute of Technology, Pasadena, CA (US)

(72) Inventors: Garrett Johnson, Costa Mesa, CA (US); Jason G. Beith, Santa Ana, CA (US); Marek Lhotak, Irvine, CA (US); Praveen De Silva, Irvine, CA (US); Peter Millson, Salt Lake City, UT (US); Francis P. Maguire, Salt Lake City, UT (US); Morteza Gharib, Altadena, CA (US)

(73) Assignees: Foldax, Inc., Salt Lake City, UT (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 16/820,274

(22) Filed: Mar. 16, 2020

(65) Prior Publication Data
US 2021/0038379 A1 Feb. 11, 2021

Related U.S. Application Data

(60) Provisional application No. 62/904,496, filed on Sep. 23, 2019, provisional application No. 62/819,839, filed on Mar. 18, 2019.

(51) Int. Cl.
*A61F 2/24* (2006.01)
*A61L 27/18* (2006.01)
*C08G 18/61* (2006.01)

(52) U.S. Cl.
CPC .......... *A61F 2/2418* (2013.01); *A61F 2/2415* (2013.01); *A61L 27/18* (2013.01);
(Continued)

(58) Field of Classification Search
CPC .................. A61F 2/07; A61F 2002/072; A61F 2002/075; A61F 2002/077; A61F 2/2418;
(Continued)

(56) References Cited

U.S. PATENT DOCUMENTS 3,550,206 A 12/1970 Von Der Heide
3,964,433 A 6/1976 Swartz
(Continued)

FOREIGN PATENT DOCUMENTS

EP 2030750 A1 3/2009
RU 2425657 C2 8/2011
(Continued)

OTHER PUBLICATIONS

US 5,489,289 A, 02/1996, Love et al. (withdrawn)
(Continued)

*Primary Examiner* — Brian A Dukert
*Assistant Examiner* — Rebecca Lynee Zimmerman
(74) *Attorney, Agent, or Firm* — Kurt T. Mulville; VLP Law Group LLP

(57) ABSTRACT

Improved prosthetic valves, their methods of manufacture, and systems and devices for manufacturing the valves are described. The prosthetic valves can be configured for transcatheter implantation. The prosthetic valves can have artificial leaflets. The prosthetic valves can be manufactured in numerous ways, such as by polymeric dipping processes and/or electrospinning. Sponge-like polymers for valves and other medical devices are also disclosed.

17 Claims, 40 Drawing Sheets

(52) U.S. Cl.
CPC ........ *C08G 18/61* (2013.01); *A61F 2240/004* (2013.01); *A61L 2430/20* (2013.01)

(58) Field of Classification Search
CPC .............. A61F 2/2415; A61F 2240/004; A61F 2/9522; A61F 2/24–2496; A61F 2002/2484–2896; A61L 27/18; A61L 2430/20; A61L 27/50; A61L 27/56; C08G 18/61

See application file for complete search history.

(56) References Cited

U.S. PATENT DOCUMENTS

| | | | |
|---|---|---|---|
| 3,983,581 A | 10/1976 | Angell et al. | |
| 4,222,126 A | 9/1980 | Boretos et al. | |
| 4,265,694 A | 5/1981 | Boretos et al. | |
| 4,291,420 A | 9/1981 | Reul | |
| 4,364,127 A | 12/1982 | Pierce et al. | |
| 4,473,423 A | 9/1984 | Kolff | |
| 4,490,859 A | 1/1985 | Black et al. | |
| 4,506,394 A | 3/1985 | Bédard | |
| 4,556,996 A | 12/1985 | Wallace | |
| 4,626,255 A | 12/1986 | Reichart et al. | |
| 4,759,759 A | 7/1988 | Walker et al. | |
| 4,778,461 A | 10/1988 | Pietsch et al. | |
| 4,888,009 A | 12/1989 | Lederman et al. | |
| 4,906,423 A | 3/1990 | Frisch | |
| 5,037,434 A | 8/1991 | Lane | |
| 5,147,391 A | 9/1992 | Lane | |
| 5,258,023 A | 11/1993 | Reger | |
| 5,376,113 A | 12/1994 | Jansen et al. | |
| 5,449,385 A | 9/1995 | Religa et al. | |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,653,749 A | 8/1997 | Love et al. | |
| 5,713,953 A | 2/1998 | Vallana et al. | |
| 5,861,028 A | 1/1999 | Angell | |
| 5,928,281 A | 7/1999 | Huynh et al. | |
| 6,117,169 A | 9/2000 | Moe | |
| 6,171,335 B1 | 1/2001 | Wheatley et al. | |
| 6,174,331 B1 | 1/2001 | Moe et al. | |
| 6,283,994 B1 | 9/2001 | Moe et al. | |
| 6,283,995 B1 | 9/2001 | Moe et al. | |
| 6,287,334 B1 | 9/2001 | Moll et al. | |
| 6,334,873 B1 | 1/2002 | Lane et al. | |
| 6,454,798 B1 | 9/2002 | Moe | |
| 6,461,382 B1 | 10/2002 | Cao | |
| 6,475,239 B1 | 11/2002 | Campbell et al. | |
| 6,478,819 B2 | 11/2002 | Moe | |
| 6,562,069 B2 | 5/2003 | Cai et al. | |
| 6,596,024 B2 | 7/2003 | Chinn | |
| 6,613,086 B1 | 9/2003 | Moe et al. | |
| 6,666,885 B2 | 12/2003 | Moe | |
| 6,716,244 B2 | 4/2004 | Klaco | |
| 6,755,857 B2 | 6/2004 | Peterson et al. | |
| 6,780,200 B2 | 8/2004 | Jansen | |
| 6,953,332 B1 | 10/2005 | Kurk et al. | |
| 6,984,700 B2 | 1/2006 | Benz et al. | |
| 7,247,167 B2 | 7/2007 | Gabbay | |
| 7,262,260 B2 | 8/2007 | Yilgor et al. | |
| 7,365,134 B2 | 4/2008 | Benz et al. | |
| 7,473,275 B2 | 1/2009 | Marquez | |
| 7,563,280 B2 | 7/2009 | Anderson et al. | |
| 7,641,687 B2 | 1/2010 | Chinn et al. | |
| 7,682,389 B2 | 3/2010 | Beith | |
| 7,776,084 B2 | 8/2010 | Johnson | |
| 7,803,186 B1 | 9/2010 | Li et al. | |
| 7,833,565 B2 | 11/2010 | O'Connor et al. | |
| 7,871,435 B2 | 1/2011 | Carpentier et al. | |
| 7,959,674 B2 | 6/2011 | Shu et al. | |
| 7,988,900 B2 | 8/2011 | Beith | |
| 8,216,631 B2 | 7/2012 | O'Connor et al. | |
| 8,845,720 B2 | 9/2014 | Conklin | |
| 9,301,837 B2 | 4/2016 | Beith | |
| 10,266,657 B2 | 4/2019 | Gunatillake et al. | |
| 2001/0021872 A1 | 9/2001 | Bailey et al. | |
| 2002/0062150 A1 | 5/2002 | Campbell et al. | |
| 2002/0198594 A1 | 12/2002 | Schreck | |
| 2003/0023302 A1 | 1/2003 | Moe et al. | |
| 2003/0055496 A1 | 3/2003 | Cai et al. | |
| 2004/0034408 A1* | 2/2004 | Majercak | A61F 2/2475 623/901 |
| 2005/0096736 A1 | 5/2005 | Osse et al. | |
| 2005/0113910 A1 | 5/2005 | Paniagua et al. | |
| 2005/0149181 A1 | 7/2005 | Eberhardt | |
| 2006/0047338 A1 | 3/2006 | Jenson et al. | |
| 2006/0184239 A1 | 8/2006 | Andrieu et al. | |
| 2006/0235512 A1 | 10/2006 | Osborne et al. | |
| 2006/0241744 A1 | 10/2006 | Beith | |
| 2006/0265052 A1* | 11/2006 | You | A61F 2/844 623/1.22 |
| 2007/0255400 A1 | 11/2007 | Parravicini et al. | |
| 2008/0154358 A1 | 6/2008 | Tansley et al. | |
| 2009/0132035 A1 | 5/2009 | Roth et al. | |
| 2010/0047436 A1 | 2/2010 | Beith | |
| 2010/0161045 A1 | 6/2010 | Righini | |
| 2011/0224780 A1 | 9/2011 | Tabor et al. | |
| 2011/0264196 A1* | 10/2011 | Savage | A61F 2/2418 623/2.11 |
| 2011/0282440 A1 | 11/2011 | Cao et al. | |
| 2012/0035719 A1 | 2/2012 | Forster et al. | |
| 2012/0078347 A1 | 3/2012 | Braido et al. | |
| 2012/0232646 A1 | 9/2012 | Agathos | |
| 2013/0096674 A1 | 4/2013 | Iobbi | |
| 2013/0184813 A1 | 7/2013 | Quadri et al. | |
| 2013/0268066 A1 | 10/2013 | Rowe | |
| 2013/0310928 A1 | 11/2013 | Morriss et al. | |
| 2013/0325116 A1 | 12/2013 | Sundler et al. | |
| 2014/0005773 A1 | 1/2014 | Wheatley | |
| 2014/0012371 A1 | 1/2014 | Li | |
| 2014/0114407 A1 | 4/2014 | Rajamannan | |
| 2014/0155997 A1* | 6/2014 | Braido | A61F 2/2409 623/2.37 |
| 2014/0167308 A1 | 6/2014 | Li | |
| 2014/0180400 A1* | 6/2014 | Bruchman | A61F 2/2415 623/2.17 |
| 2014/0180402 A1 | 6/2014 | Bruchman et al. | |
| 2014/0214158 A1 | 7/2014 | Board et al. | |
| 2015/0112421 A1* | 4/2015 | Barnes | A61F 2/2412 623/2.11 |
| 2015/0119980 A1 | 4/2015 | Beith et al. | |
| 2015/0224231 A1* | 8/2015 | Bruchman | A61F 2/2418 156/70 |
| 2015/0320554 A1 | 11/2015 | Beith et al. | |
| 2015/0328000 A1* | 11/2015 | Ratz | A61F 2/2445 623/2.37 |
| 2016/0038281 A1* | 2/2016 | Delaloye | A61F 2/2418 623/2.18 |
| 2016/0214303 A1 | 7/2016 | Gerstenhaber et al. | |
| 2016/0296324 A1 | 10/2016 | Bapat et al. | |
| 2017/0049566 A1* | 2/2017 | Zeng | A61F 2/2412 |
| 2017/0071735 A1 | 3/2017 | Guttenberg et al. | |
| 2017/0119923 A1 | 5/2017 | Gunatillake et al. | |
| 2017/0281336 A1 | 10/2017 | Lane et al. | |
| 2017/0354498 A1* | 12/2017 | Frisby | A61F 2/2436 |
| 2018/0008406 A1* | 1/2018 | Bruchman | A61L 27/507 |
| 2018/0116794 A1 | 5/2018 | Beith | |
| 2018/0125646 A1* | 5/2018 | Bruchman | A61F 2/2412 |
| 2018/0221146 A1* | 8/2018 | Jana | D01D 5/0007 |
| 2018/0263769 A1 | 9/2018 | Hariton et al. | |
| 2018/0346654 A1 | 12/2018 | Gunatillake et al. | |
| 2019/0029828 A1 | 1/2019 | Carpentier et al. | |
| 2019/0060661 A1 | 2/2019 | Beith et al. | |
| 2019/0274828 A1* | 9/2019 | Delaloye | A61F 2/2409 |
| 2019/0343625 A1 | 11/2019 | Gharib et al. | |
| 2020/0022807 A1* | 1/2020 | Karciauskas | A61F 2/2418 |
| 2020/0060814 A1* | 2/2020 | Murphy | A61F 2/2475 |

(56) References Cited

U.S. PATENT DOCUMENTS

| | | | |
|---|---|---|---|
| 2020/0246141 A1* | 8/2020 | Peterson | A61F 2/2433 |
| 2020/0289260 A1* | 9/2020 | Kuang | A61F 2/2436 |

FOREIGN PATENT DOCUMENTS

| | | |
|---|---|---|
| WO | 2002100301 | 12/2002 |
| WO | WO 2004/019825 A1 | 3/2004 |
| WO | 2007140964 | 12/2007 |
| WO | WO 2013/160651 A1 | 10/2013 |
| WO | WO 2014/170870 A2 | 10/2014 |
| WO | WO 2016/098073 A1 | 6/2016 |
| WO | 2016138416 | 9/2016 |
| WO | WO 2019/028374 A1 | 2/2019 |

OTHER PUBLICATIONS

"Morphology and surface properties of high strength siloxane poly(urethane-urea)s developed for heart valve application" Journal of Biomedical Materials Research Loshini S. Dandeniyage, Raju Mar. 4, 2018 (Year: 2018).*

"PCT Invitation to Pay Additional Fees, PCT/US2020/022948", Jun. 18, 2020, 2 pages.

"PCT Search Report and Written Opinion, PCT/US2020/022948", Aug. 28, 2020, 18 pages.

EP, 15789241.5 Supplementary Search Report, Oct. 27, 2017.

WO, PCT/US2015/013980 ISR and Written Opinion, May 28, 2015.

WO, PCT/US2017/058588 ISR and Written Opinion, Feb. 21, 2018.

WO, PCT/US2018/045202 ISR and Written Opinion, Nov. 22, 2018.

WO, PCT/US2018/064792 ISR and Written Opinion, Apr. 15, 2019.

Dandeniyage, L.S., et al., "Development of high strength siloxane poly(urethane-urea) elastomers based on linked macrodiols for heart valve applications", J. Biomed. Mater. Res. Part B, 2018, vol. 106, No. 5, pp. 1712-1720.

Pibarot, P., et al., "Prosthetic Heart Valves: Selection of the Optimal Prosthesis and Long-Term Management", Circulation, 2009, vol. 119, pp. 1034-1048.

Webb, J. G., et al., "Transcatheter Aortic Valve Replacement for Bioprosthetic Aortic Valve Failure: The Valve-in-Valve Procedure", Circulation, 2013, vol. 127, pp. 2542-2550.

Yilgör, E., et al., "Silicone containing copolymers: Synthesis, properties and applications", Progress in Polymer Science, 2014, vol. 39, No. 6, pp. 1165-1195.

* cited by examiner

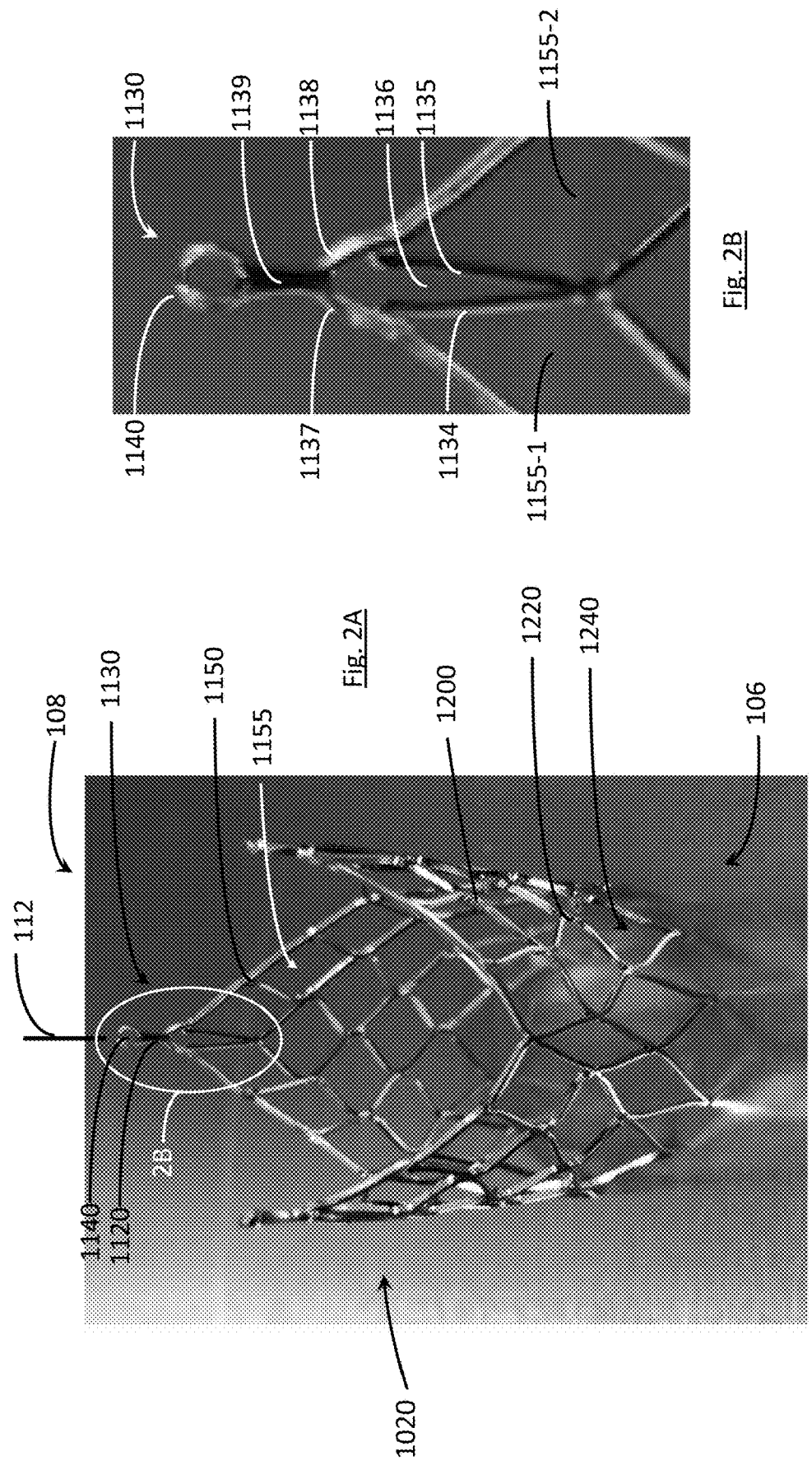

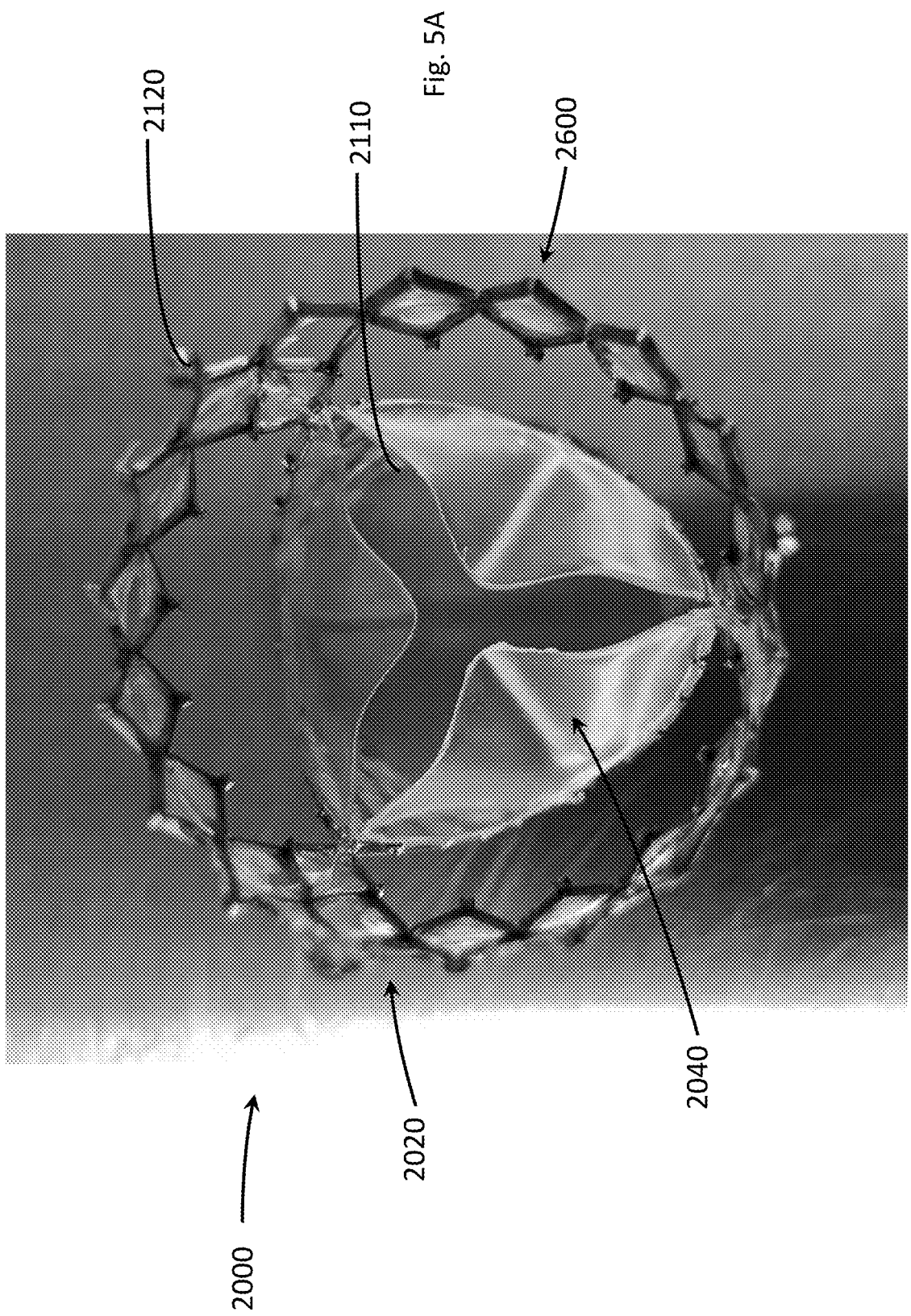

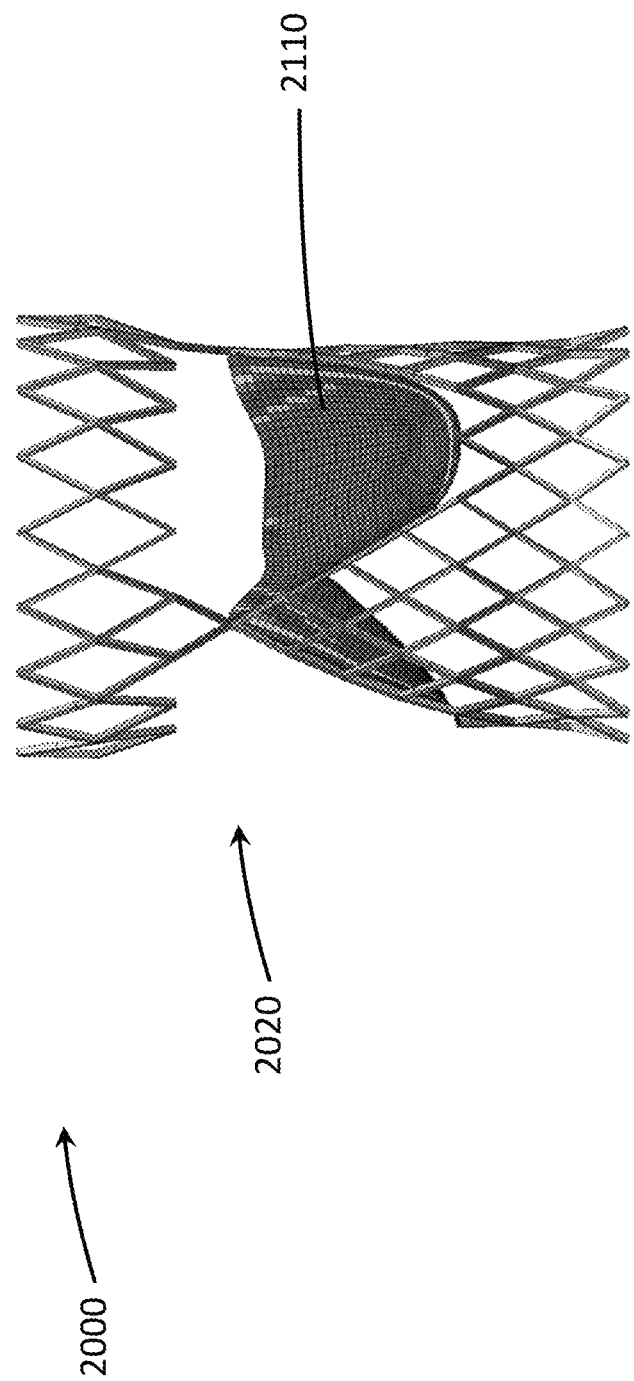

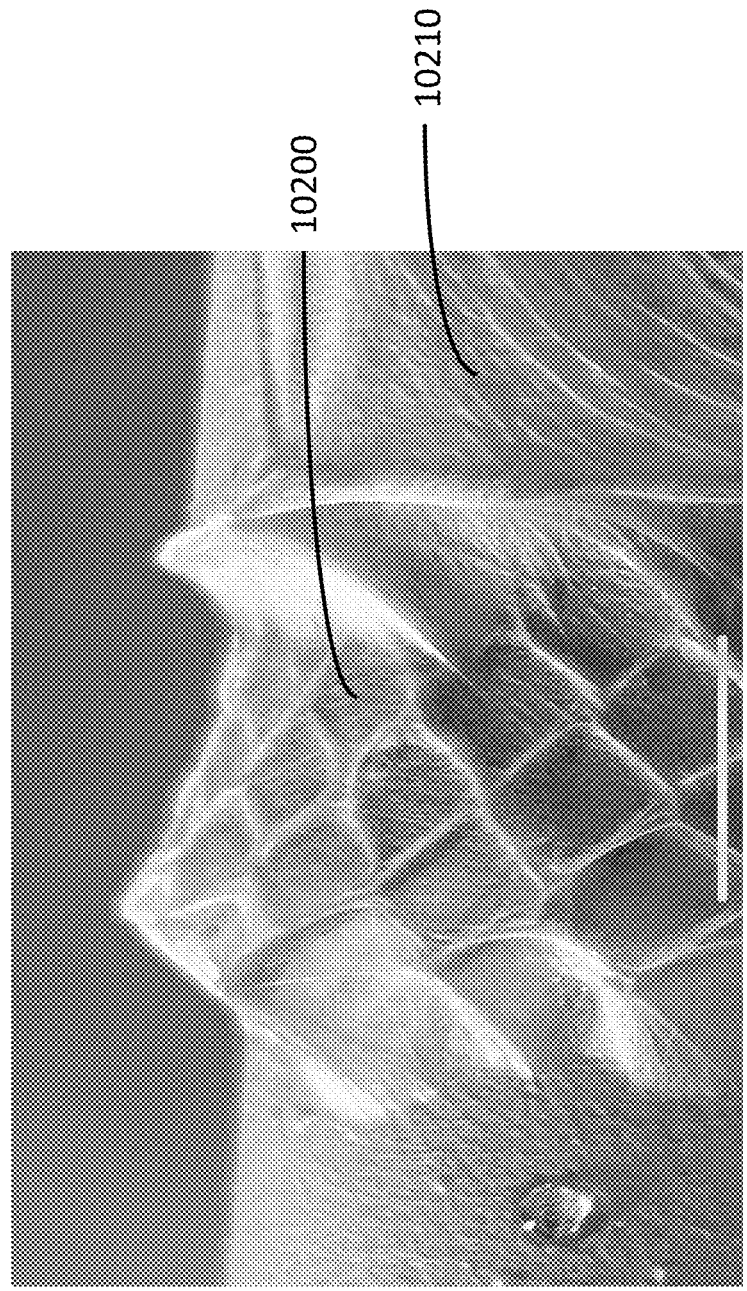

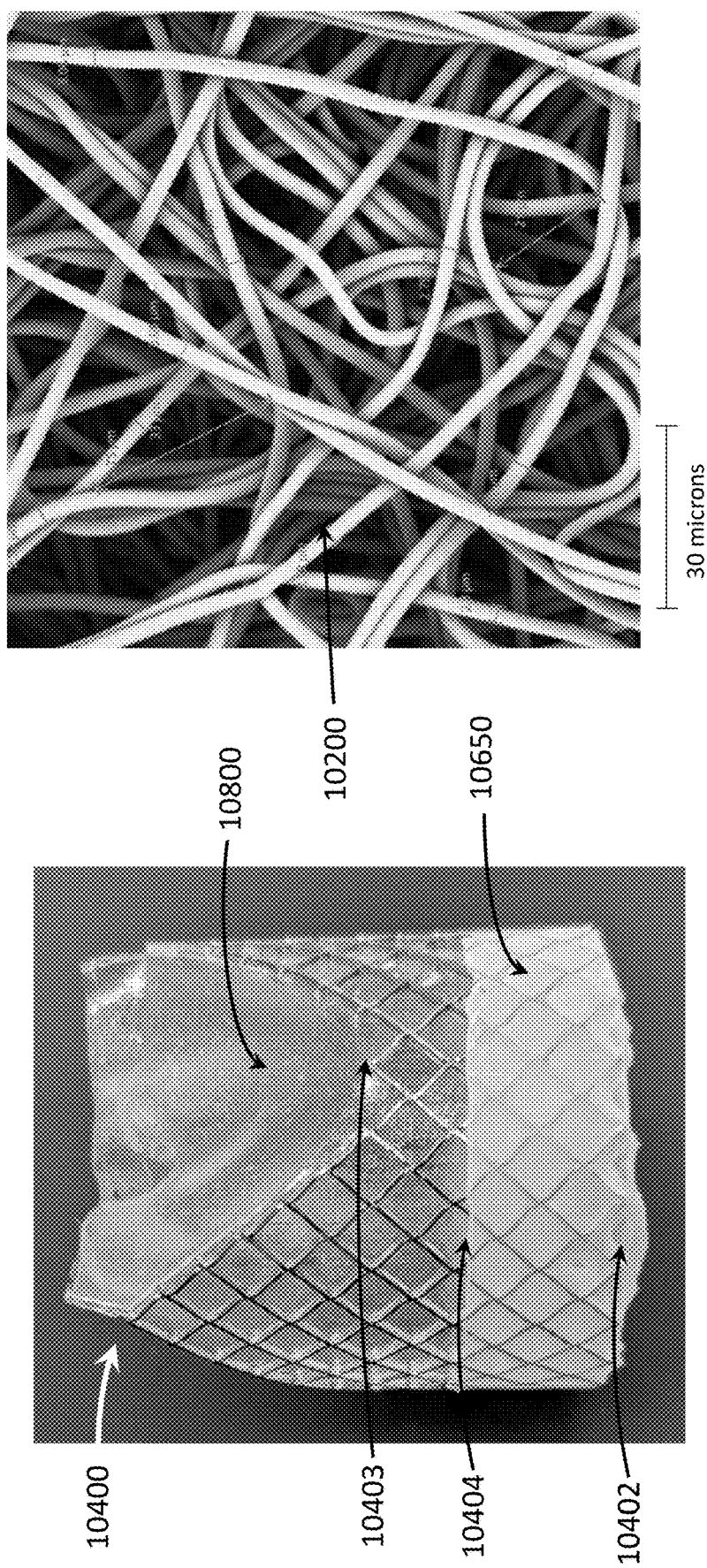

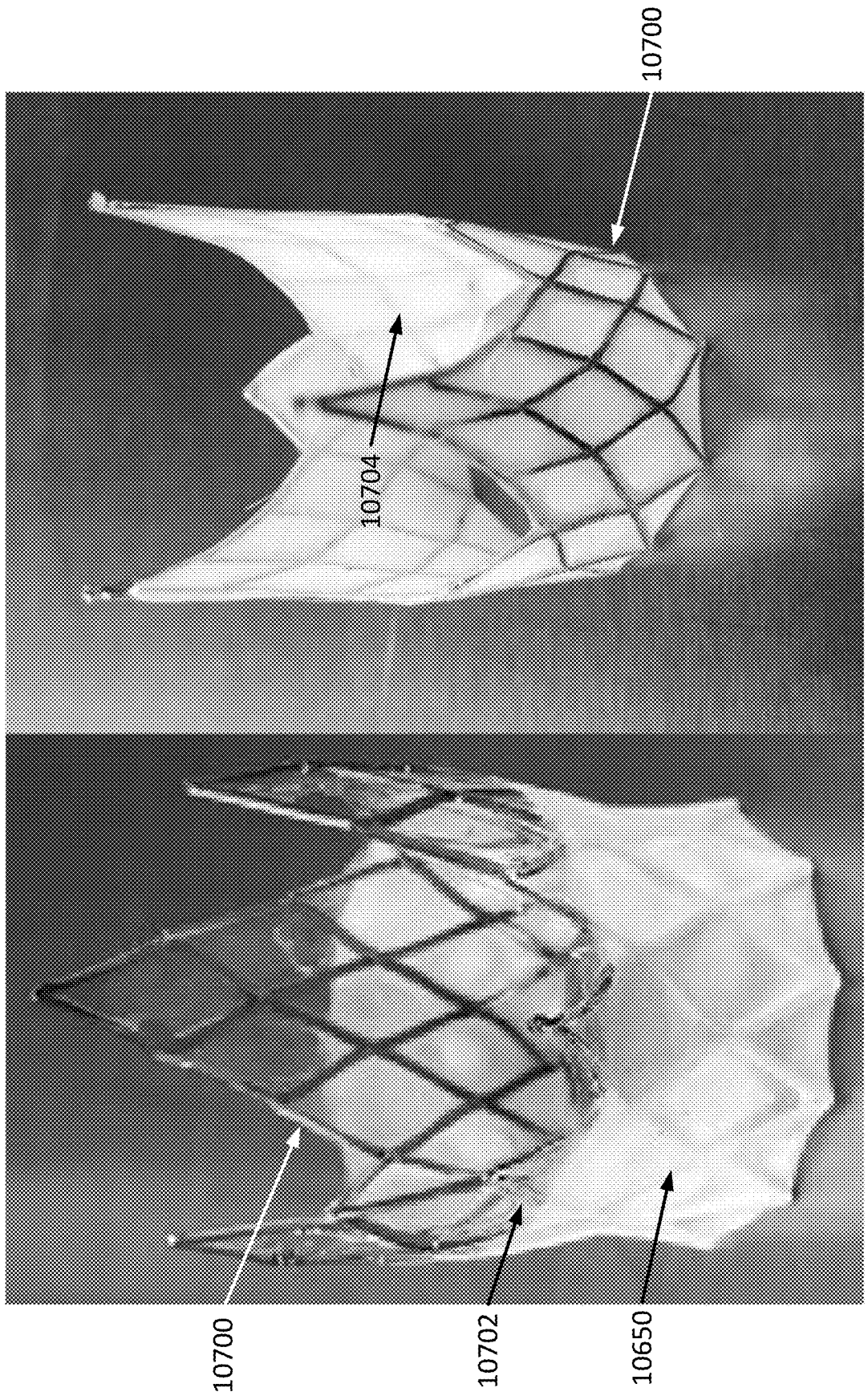

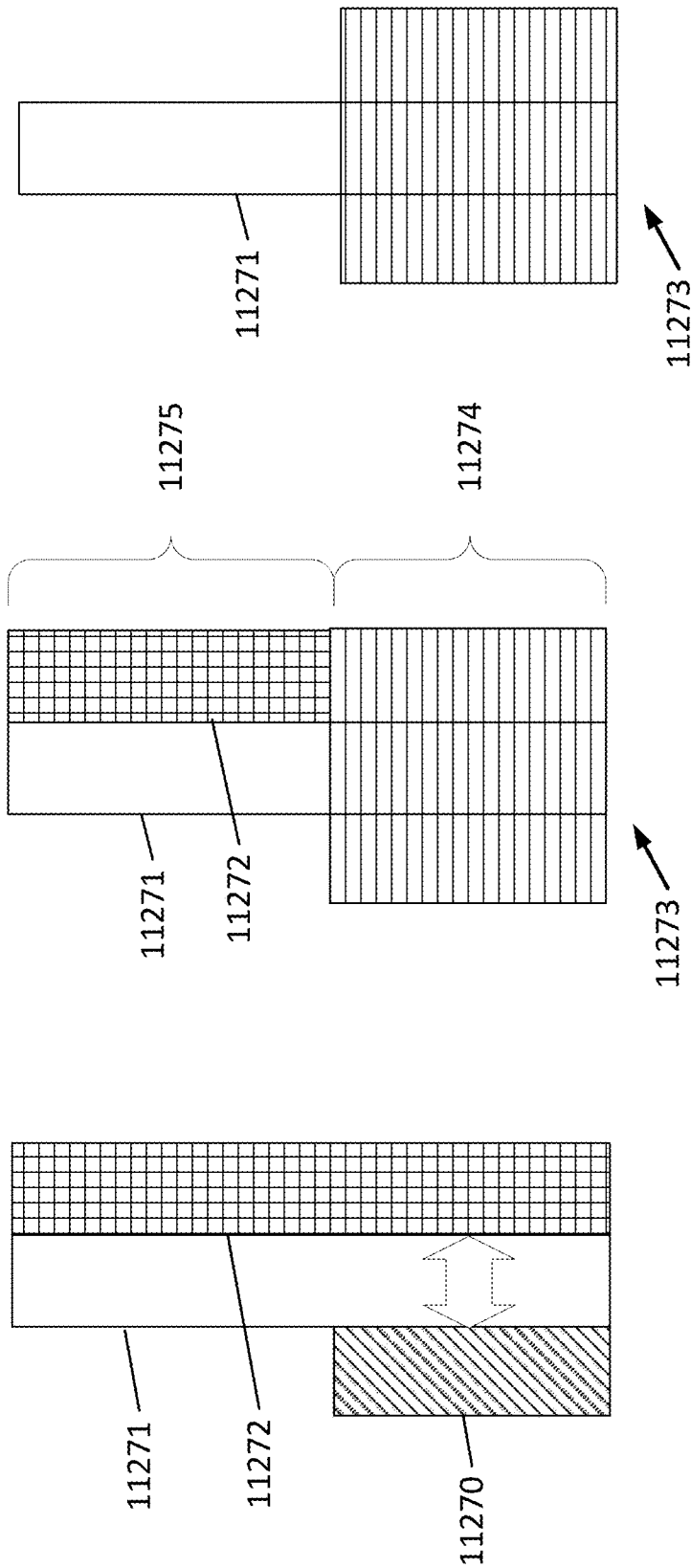

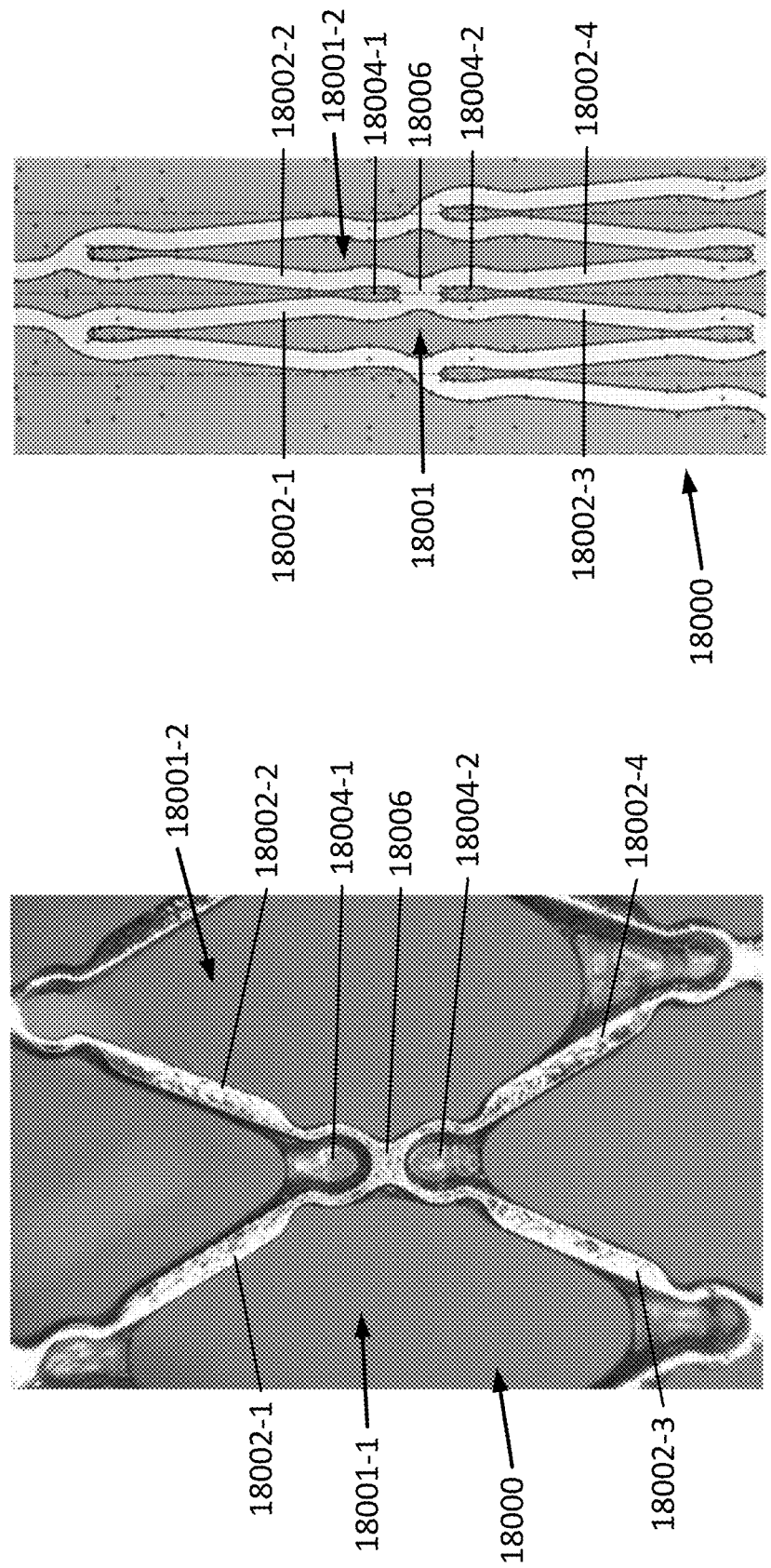

SYSTEMS, DEVICES, AND METHODS RELATING TO THE MANUFACTURE OF IMPLANTABLE PROSTHETIC VALVES

CROSS-REFERENCE TO RELATED APPLICATIONS

This application claims the benefit of and priority to U.S. Provisional Patent Application Ser. No. 62/819,839, filed Mar. 18, 2019 and U.S. Provisional Patent Application Ser. No. 62/904,496, filed Sep. 23, 2019, both of which are incorporated by reference herein in their entireties and for all purposes.

FIELD

The subject matter described herein relates generally to improved replacement valves, and more particularly to improved techniques for the manufacture and manufacturability of prosthetic valves, such as implantable prosthetic heart valves having two or more artificial polymeric leaflets.

BACKGROUND

The human heart has a number of valves for maintaining the flow of blood through the body in the proper direction. The major valves of the heart are the atrioventricular (AV) valves, including the bicuspid (mitral) and the tricuspid valves, and the semilunar valves, including the aortic and the pulmonary valves. When healthy, each of these valves operates in a similar manner. The valve translates between an open state (that permits the flow of blood) and a closed state (that prevents the flow of blood) in response to pressure differentials that arise on opposite sides of the valve.

A patient's health can be placed at serious risk if any of these valves begin to malfunction. Although the malfunction can be due to a variety of reasons, it typically results in either a blood flow restricting stenosis or a regurgitation, where blood is permitted to flow in the wrong direction. If the deficiency is severe, then the heart valve may require replacement.

Substantial effort has been invested in the development of replacement heart valves, most notably replacement aortic and mitral valves. There is currently substantial interest in the transcatheter implantation of prosthetic valves. Transcatheter valve implementations often involve a bioprosthetic valve integrated with an artificial arterial stent. This method offers the advantages of a tissue based valve with the minimally invasive catheter based implantation technique. Examples of such transcatheter implantation techniques include aortic valve replacement techniques, such as transcatheter aortic valve implantation (TAVI) and transcatheter aortic valve replacement (TAVR), and mitral valve replacement techniques such as transcatheter mitral valve implantation (TMVI) and transcatheter mitral valve replacement (TMVR). These techniques involve introducing the valve prosthesis to the patient's body by way of a catheter, and then expanding the prosthesis over the existing damaged heart valve (as opposed to resecting the native valve first). Transcatheter implantations of bioprosthetic valves suffer from the finite life span of the biological tissue used to form the valve leaflets, further exacerbated by the catheter based implantation. In order to fit the valve into a catheter, the valve must be reduced to a smaller cross-sectional size than the size necessary for operation in the aortic or mitral valve position. This size reduction can create creases and crimps in the tissue leaflets, and these creases and crimps are susceptible to calcification at a higher rate than uncreased tissue.

For these and other reasons, needs exist for improved implantable valves, and for improved systems, devices, and methods for manufacturing implantable valves.

SUMMARY

Provided herein are a number of example embodiments of prosthetic valves configured for implantation through a catheter or other intravascular delivery device, with some embodiments directed to surgically implantable valves. The valves can be configured for use as aortic or mitral heart valves, venous valves, or others. The intravascular embodiments generally include a stent or support structure coupled with a valvular body having two or more artificial polymeric leaflets. The intravascularly implantable prosthetic valves can be contracted to a reduced radial dimension that permits passage through the patient's vasculature or otherwise introduced into the patient's body at a dimension smaller than that required post-implantation. The prosthetic valves can expand, in many embodiments autonomously, to an expanded configuration for operation in regulating the patient's blood flow. The prosthetic valves can be configured as aortic, mitral, tricuspid, and pulmonic valve replacements. Numerous different embodiments of expandable and contractable frames are described, as are features that can be included in those frames.

Systems, devices, and methods for manufacturing or use in manufacturing a prosthetic heart valve are also provided. Many of these embodiments utilize a dip casting or dipping process that involves immersing some or all of an element of the prosthetic valve (or used in formation of the prosthetic heart valve) into a wet polymer to form a coating of polymer thereon. The polymer can then be cured to form a coating on a portion of the heart valve or to form a component of the heart valve itself. Numerous variations of method embodiments are disclosed, and these methods themselves can be altered, rearranged, and supplemented with additional steps.

Systems, devices, and methods for manufacturing or use in manufacturing a prosthetic heart valve are also provided. Many of these embodiments utilize electrospinning polymer onto a frame to form the valve. Numerous variations of method embodiments are disclosed, and these methods themselves can be altered, rearranged, and supplemented with additional steps.

Systems, devices, and methods utilizing sponge-like polymers are disclosed, as are methods of manufacturing sponge-like polymers. The sponge-like polymers can be utilized in a wide range of medical devices, such as valves, stents, replacement discs and vertebrae, filters, tissue scaffolds, and vascular patches.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 2A is a perspective view depicting an example embodiment of an expanded frame for use with a prosthetic valve.

FIG. 2B is a perspective view of region 2B of FIG. 2A.

FIG. 5A is a top down view depicting an example embodiment of a prosthetic valve.

FIG. 5C is a sideview depicting an example embodiment of a prosthetic valve.

FIG. 10A is an image of an example embodiment of a sealing skirt.

FIG. 10D is an image of an example embodiment of a valve.

FIG. 10E is a magnified image of a sealing skirt of a valve.

FIGS. 10F-10H are images of example embodiments of a frame with a sealing skirt.

FIG. 10I is an image of a frame having an inner liner.

FIGS. 11E-11G are cross-sectional illustrations depicting a portion of a valve prosthesis at various stages of manufacture.

FIG. 18A is an image of a portion of an example embodiment of a frame having polymer welled within pockets of a frame in an expanded state.

FIG. 18B is an illustration of a portion of an example embodiment of a frame in a crimped state.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The example embodiments described herein relate to improved implantable prosthetic valves, such as prosthetic heart valves having a support structure, stent, or frame coupled with two or more leaflets, and techniques for the manufacture and manufacturability of implantable valves. These embodiments are particularly suited for artificial (not biological tissue) polymeric leaflets, and the resulting artificial valves offer advantages comparable to current approaches with the added benefit of a longer life span. Valves with polymer-based leaflets are advantageous because polymers can offer the same structural support as biological tissue, while being much thinner and allowing the valve to be more easily contracted for delivery. This in turn results in less stress on the polymer as it is contracted which prevents long-term degradation of the valve leaflets. In addition, the manufacturing methods described herein permit fabrication of a valve without suturing or molding leaflets to a support structure or stent, thus promoting high quality repeatable results.

While the embodiments described herein are particularly suited to heart valves (aortic and mitral), they can be likewise used in peripheral valves or others. The embodiments can likewise be used with stents and stent graft devices, or other medical devices implantable within the human body.

Figure 1A:
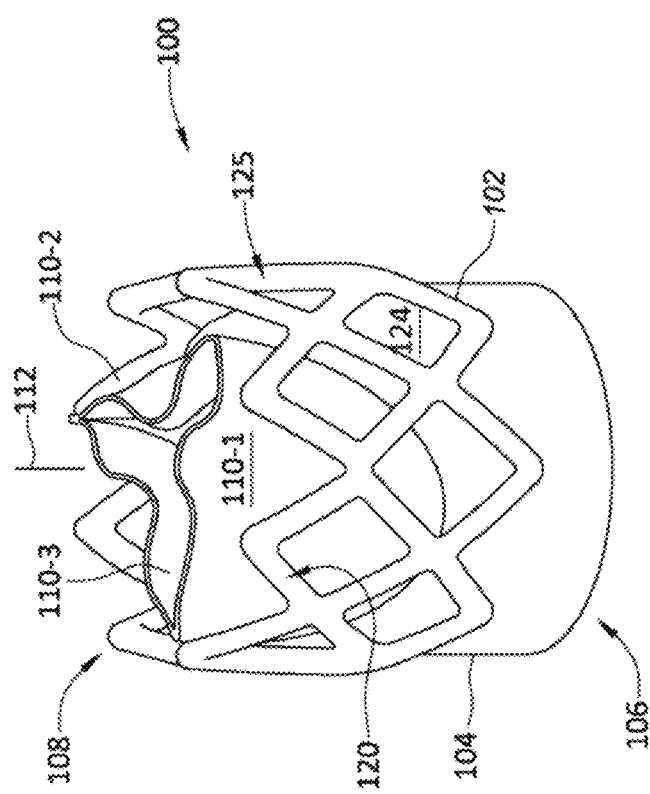
FIG. 1A is a perspective view depicting a prosthetic valve known in the art.

FIG. 1A is a perspective view depicting an example implantable prosthetic valve 100 known in the art having a support structure 102 and a valvular body 104. In this embodiment the valvular body is configured as an aortic replacement valve and has three valve leaflets 110-1, 110-2, and 110-3. Valve 100 is configured to allow blood to flow from an upstream end 106 (sometimes referred to as the proximal end or inflow end) to a downstream end 108 (sometimes referred to as the distal end or outflow end) and valve 100 has a longitudinal axis 112 extending between upstream end 106 and downstream end 108 parallel to the primary direction of blood flow through the valve.

Figure 1B:
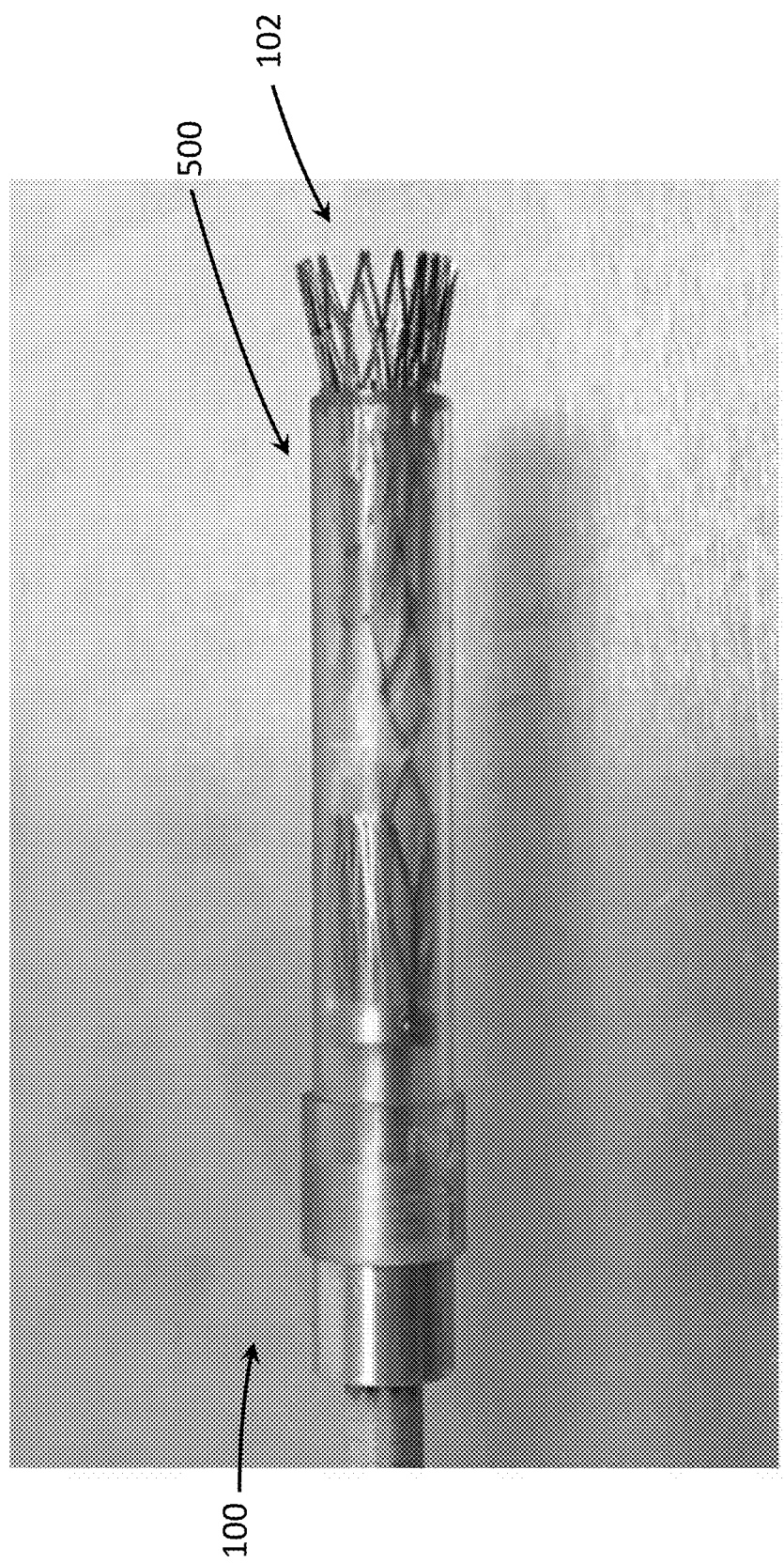
FIG. 1B is a side view depicting an example embodiment of a contracted frame for use with a prosthetic valve.

Many embodiments of valves described herein can be configured for transcatheter implantation (unless otherwise stated), and thus can transition between, on the one hand, an expanded or operative configuration (having a relatively larger radial dimension) for regulating blood flow and, on the other hand, a contracted, crimped, or deliverable configuration (having a relatively smaller radial dimension) that permits insertion in a delivery device (e.g., catheter) for intravascular or transapical delivery. FIG. 1B shows a valve 100 reduced in size from the expanded state to a contracted state. FIG. 1B shows support structure 102 in a contracted state within a delivery device 500. All embodiments of valves described herein can be self-expandable, such that the valve expands from the contracted state to the expanded state automatically upon exiting or being released from the delivery device without assistance from another entity, or balloon expandable, such that the valve expands with the assistance of an inflatable balloon or other expandable member.

Support structure 102 is coupled with valvular body 104 and provides radial and longitudinal support for body 104. As shown in FIG. 1A, the body of support structure 102 includes multiple struts 120 coupled together in a unitary or monolithic body. Each strut 120 is coupled with another strut at a location that is deformable for transition of structure 102 between the expanded (shown here) and contracted states. In this example, struts 120 are interconnected in a crossing pattern, or lattice, such that multiple open regions 124 are present. These open regions 124 have a four-sided diamond shape in the configuration shown here. Support structure 102 can also be referred to as a frame or stent.

Example Embodiments of Prosthetic Valves

FIG. 2A is a perspective view depicting an example embodiment of a frame 1020, which is a support structure for an implantable prosthetic valvular body, e.g., valvular body 1040 (not shown in this figure). This embodiment can be reduced in size from an expanded to a contracted state. In the embodiment of FIG. 2A, the body of frame 1020 includes multiple struts 1200 coupled together in a unitary or monolithic body. Each strut 1200 is coupled with another strut, e.g., at a location 1220, that is deformable for transition of frame 1020 between the expanded and contracted states (FIG. 1 shows the frame 102 in an expanded state). In this embodiment, struts 1200 are interconnected in a crossing pattern, or lattice, such that multiple open regions 1240 are present.

These open regions 1240 generally have a four-sided diamond shape in the expanded configuration shown here. The open region 1240 and the struts 1200 forming the sides (four struts in this embodiment) of open region 1240 are together referred to as a cell 1155 of the frame. Many of the struts 1200 are generally oriented at an angle with respect to longitudinal axis 112.

At the downstream 108 side of frame 1020, there are three commissure positions. Each commissure position aligns with the intersection between two adjacent leaflets (not shown). Thus, this embodiment is configured for use with a three leaflet valvular body. One of these commissure positions is indicated by reference number 1120. At the top of this position 1120, a strut 1130 is formed with a deflection attenuation feature that advantageously stiffens that portion of frame 1020. This feature 1130 may facilitate prevention of excess deflection under full diastolic loading. In this example embodiment feature 1130 is T-shaped, although in other embodiments the feature may have an alternative arrangement.

Referring to FIG. 2A, along the edge 1150 of the frame 1020, at the downstream 108 end, where the upstream edge of a valve's leaflet would be (not shown here, see, e.g., FIG. 3), the struts 1200 form a continuous edge 1150. This configuration can minimize leaflet stress in that region. This continuous edge 1150 is constructed by connecting a non-uniform, unique lattice of individual frame cells 1155 formed by struts 1200. Each cell 1155 of the frame 1020 can be uniquely designed to achieve the angled geometry desired by the edge 1150. This frame 1020 design enables open coronary access and supra-annular leaflet placement, which has been shown to lead to clinically significant lower gradient levels.

Region 1130 is shown in greater detail in FIG. 2B. Whereas adjacent diamond-shaped cells share struts, in the region of the deflection attenuation feature 1130 the adjacent cells 1155-1 and 1155-2 each has its own interior strut 1134 and 1135, respectively. The downstream portion of cells 1155-1 and 1155-2 are coupled with struts 1137 and 1138, respectively, forming a relatively smaller cell 1136. A longitudinal strut 1139 extends downstream from the junction between struts 1137 and 1138, and is capped at the downstream end 108 with a loop 1140, which is used to attach the frame 2020 to a delivery system (not shown) such as with a tether.

Figure 3:
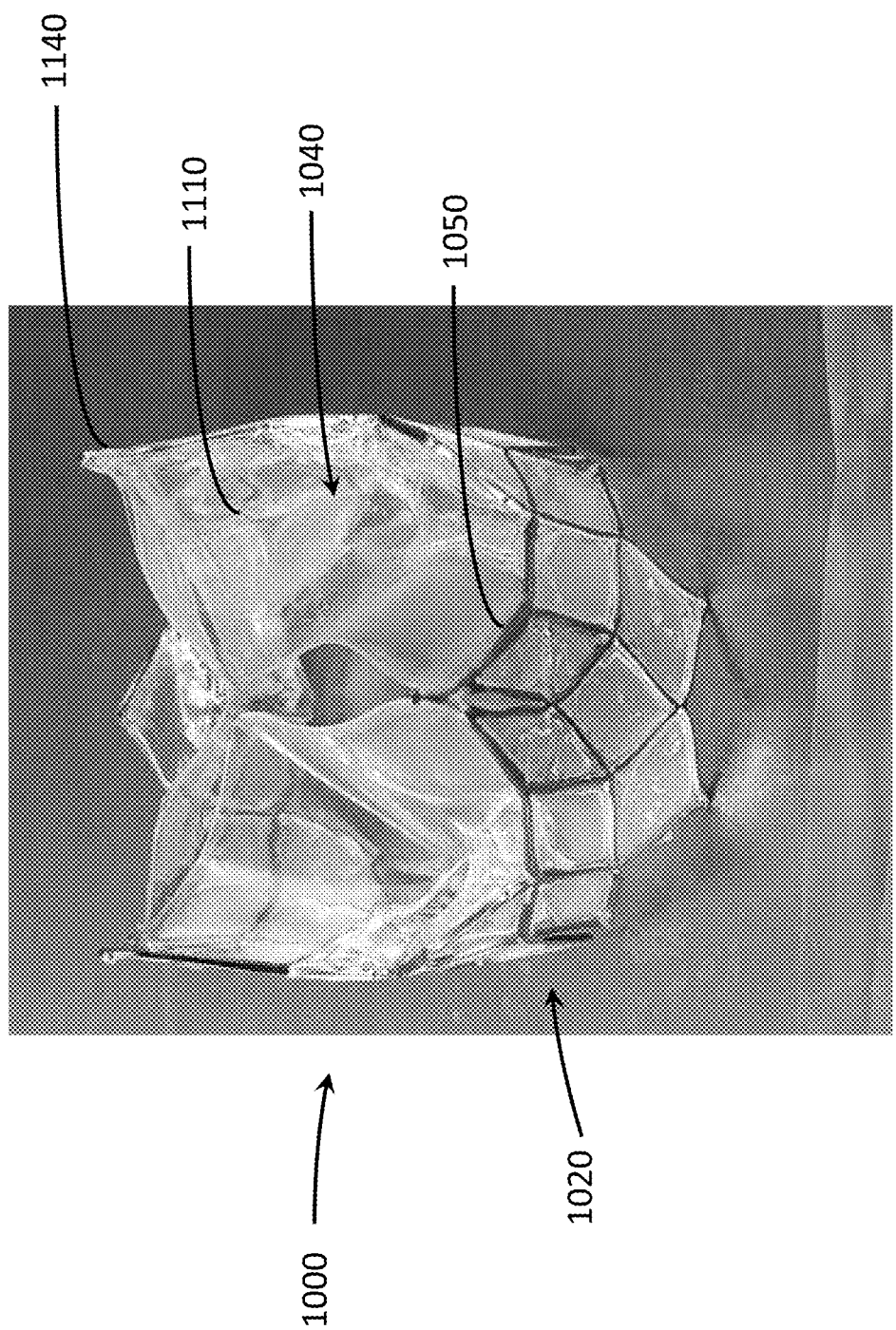
FIG. 3 is a top down view depicting an example embodiment of a prosthetic valve.

FIG. 3 depicts an embodiment of valve 1000 is shown with frame 1020 in the expanded state supporting a valvular body 1040 in a partially open state. The valvular body 1040 includes three leaflets 1110, each with an outer upstream edge 1050 attached to and supported by the frame 1020 at a commissure position 1120. This embodiment of frame 1020 is similar to that of FIGS. 2A-2B but with a shorter longitudinal length.

Figure 4:
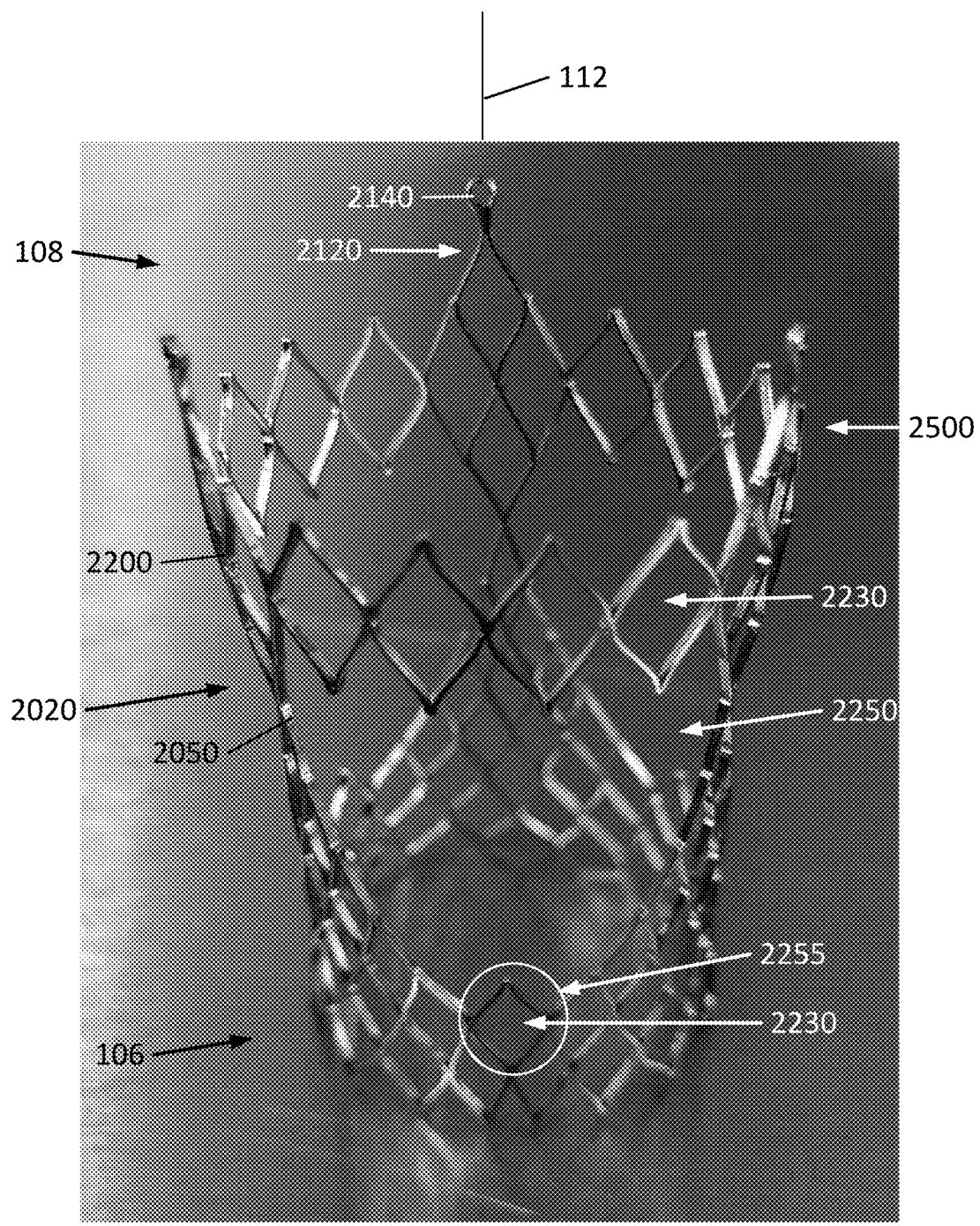
FIG. 4 is a perspective view depicting an example embodiment of a frame for use with a prosthetic valve.
Figure 5B:
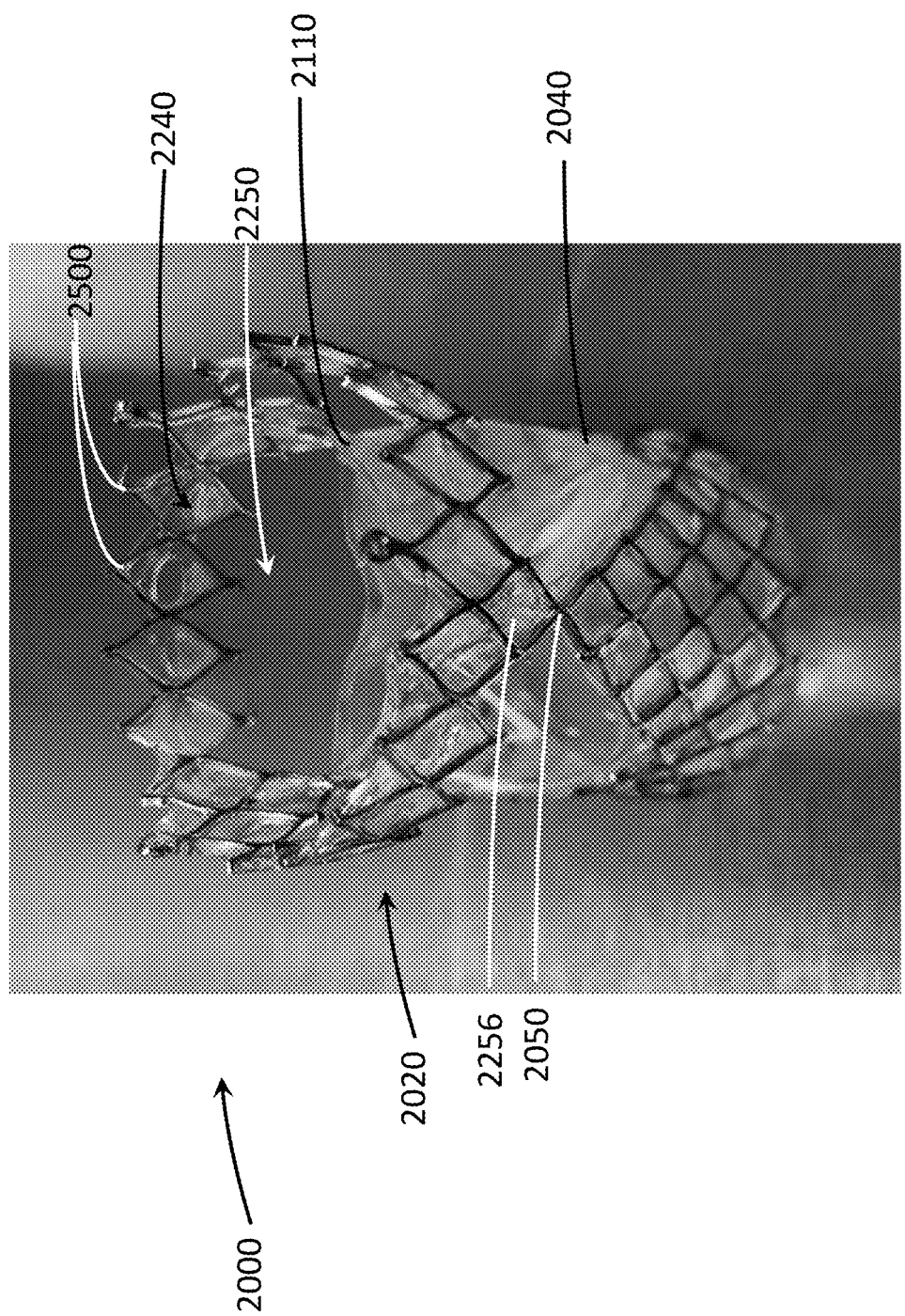
FIG. 5B is a perspective view depicting an example embodiment of a prosthetic valve.

FIG. 4 is a perspective view depicting example embodiment of a stent or frame 2020, which is a supporting structure for an implantable valvular body (see valve 2000 of FIGS. 5A-5C). In the embodiment of FIG. 4, frame 2020 includes multiple struts 2200 deflectably coupled together. In this embodiment the frame 2020 is a unitary or monolithic structure machined or cut from a single source object, such that the struts are seamlessly interconnected. Alternatively, one or more of the struts can be formed individually and then physically coupled together to form the frame, where each strut connection is a weld or other form of attachment. The struts 2200 are deformable for transition of frame 2020 between the expanded and contracted states. In this embodiment, struts 2200 are also arranged in a crossing pattern, or lattice, such that multiple interior regions 2230 are present.

These interior regions 2230 generally have a four-sided diamond shape in the configuration shown here. The interior regions 2230 and the struts 2200 forming the sides (four struts in this embodiment) of region 2230 constitute a cell 2255 of the frame 2020. Adjacent cells 2255 share at least one strut 2200. In the expanded configuration, many of the struts 2200 are generally oriented at an angle with respect to longitudinal axis 112, whereas that angle is reduced in the contracted state.

FIG. 5A shows valve 2000 with frame 2020 from downstream end 108, supporting a valvular body 2040 having three valve leaflets 2110. Each valve leaflet 2110 is supported by frame 2020 at or near a commissure position 2120. FIG. 5B shows a perspective view of valve 2000 with frame 2020, supporting valvular body 2040. FIG. 5C is a side view of a simulation of valve 2000 showing frame 2020 and individual leaflets 2110 (but omitting the rest of the valvular body and any polymer within the frame cells for ease of illustration).

In the embodiments of FIGS. 4 and 5A-5C, downstream end 108 of frame 2020 includes a crown or crown section 2500 located upstream to commissure positions 2050. In these embodiments, crown 2500 includes a single row of cells 2255 repeated continuously around the circumference of frame 2020. Crown 2500 includes six additional cells 2255, three of which are located adjacent and downstream to the single row to form crests 2120 (discussed below), and three of which (cells 2256) are located adjacent and upstream to the single row above commissure positions 2050.

Crown 2500 can aid in reducing deflection experienced by the frame 2020, which can lead to lower valvular leaflet stresses. Additionally, crown 2500 can function as a straightening feature to help stabilize inflow side 106 if incorrectly implanted at an oblique angle. If the native annulus is oval, crown 2500 can also help keep the prosthetic valve round, therefore functioning with lower stress. Crown 2500 can also provide additional anchoring in the sinutubular junction (STJ). Crown 2500 can also help keep the valve straight and/or aligned if deployed at an angle. The cells of crown 2500 can be filled with polymer (see FIG. 5B) or can be absent of polymer, for example, to minimize effect on blood flow through the cells. Crown 2500 may also allow for the release of the valve 2000 at a later stage, once the prosthetic valve 2000 is semi-functional, allowing assessment of anchoring and/or flow without fully releasing the valve 2000.

Crests 2120 and are each aligned with a commissure position 2050. Only one of the crest positions 2120 and commissure positions 2050 are labeled in FIG. 4. The top or downstream end of crest 2120 is coupled with a locking feature 2140, which in this embodiment is a loop that can be used to attach the frame to the delivery system (not shown) such as with a tether. Other structures such as a hook or strut can be used as the locking feature. In other embodiments, crests 2120 and locking features 2140 can be offset from commissure positions 2050. For example, crests 2120 and locking features 2140 can be moved from the commissure aligned positions shown in FIG. 5A to positions 2600 halfway between commissure positions 2050. The valve is typically deployed inflow-end first when implanted. When locking features 2140 are aligned with commissure positions 2050, the operation of the valve (regulation of blood flow by the leaflets) begins relatively later than for configurations where locking features 2140 are positioned midway between commissures 2050 (such as in positions 2600). Thus, placement of locking features 2140 in positions 2600 can permit earlier valve operation during the deployment.

Three open regions 2250 are positioned below (on the upstream side of) crown 2500 in the waist area of frame 2020 are defined in between commissure positions 2120. As shown in FIG. 4, these open regions 2250 in the waist area are generally located in between the downstream 108 and upstream 106 ends and are larger in size than any given cell 2255 within frame 2020. In one embodiment, downstream end 108 of open region 2250 has a width of multiple columns of cells 2255, whereas the upstream end 106 of open region 2250 is narrower, and the length of open region 2250 is defined by multiple rows of cells 2255. These open regions 2250 can have a longitudinal length (measured parallel to longitudinal axis 112) greater than the longitudinal length of the leaflets (see FIG. 5B) which provides a gap on the downstream side of the leaflet's free edge that enables direct access to the coronaries in the case of subsequent coronary intervention, if required. These open regions 2250 also may allow free flow into coronaries and prevent the need to radially align, or "clock," the valve with respect to the coronary anatomy. These open regions 2250 can also allow access to and/or from the coronaries for a diagnostic or treatment device.

In other embodiments, crown 2500 can include multiple rows of cells 2255, can form crests 2120 with multiple cells or with non-cell structures, can omit crests 2120 altogether, and/or can omit the cells 2256 connecting the single row to commissure positions 2050 with or without another structure that provides an adequate gap for coronary intervention.

The leaflets 2110 of the valvular body 2040 are formed just below the top of open region 2250. In this embodiment, valvular body 2040 is formed on or attached to frame 2020 in a manner such that most or all of interior regions 2230 are at least partially sealed or entirely sealed (such that no aperture exists) with polymer in either film or fiber form, including regions 2230 in the crown feature 2500 and regions 2230 in the main body of the valve beneath the crown. In other embodiments, regions 2230 of crown feature 2500 are open and free of polymer. Valvular body 2040 with leaflets 2110 may further be formed outside of frame 2020, which may facilitate crimping.

Figure 5F:
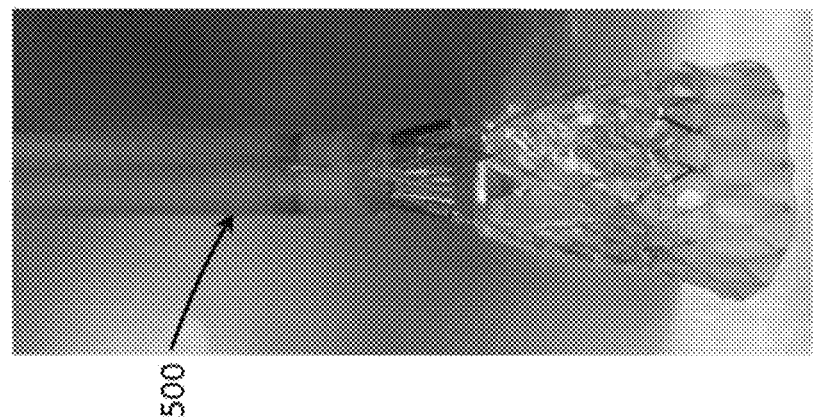
FIG. 5F is a side view depicting an example embodiment of a partially contracted frame for use with a prosthetic valve.
Figure 5E:
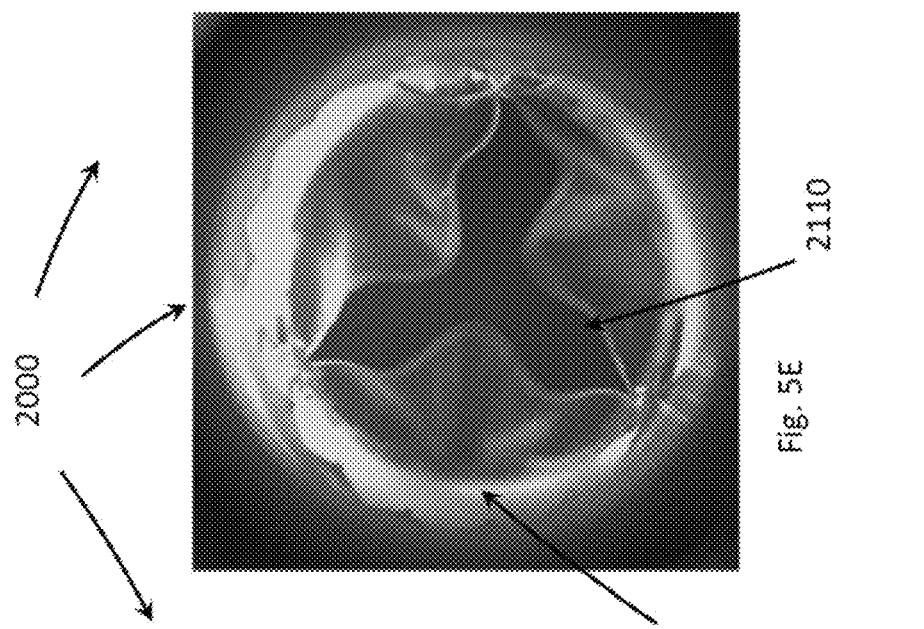
FIG. 5E is a top down view depicting an example embodiment of a prosthetic valve.
Figure 5D:
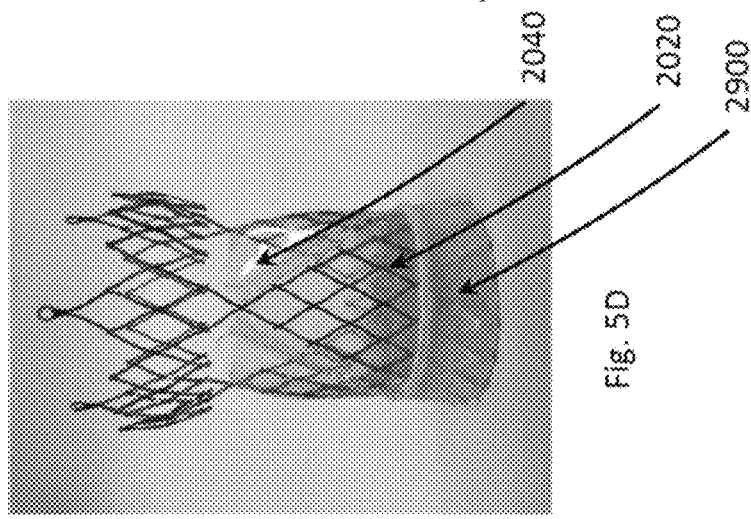
FIG. 5D is a sideview depicting an example embodiment of a prosthetic valve.

FIG. 5D is another side view of valve 2000 having frame 2020 and valvular body 2040 within frame 2020. Also shown is a seal 2900 that is configured as a sealing skirt on the inflow end 106 of frame 2020. Seal 2900 is suturelessly attached to the prosthesis by way of polymer bonding with the frame and/or polymer on the frame. FIG. 5E shows a valve 2000 from the outflow 108 end. Leaflets 2110 of valvular body 2040 can be seen from this view. FIG. 5F shows valve 2000 in a partially contracted state with the outflow end within a delivery device 500, as would occur during deployment.

While the embodiments of valve 1000 and 2000 have a generally right cylindrical upstream end, these embodiments can alternatively have a curved or scalloped upstream end. Scalloped ends are known to those of skill in the art (see, e.g., U.S. Pat. No. 9,301,837, which is incorporated by reference herein in its entirety and for all purposes.

While not required, frames 1020 and 2020 are preferably fabricated in stages from one or more materials (e.g., a primary or core structure of one material with a secondary structure or coating of the same or another material). In all embodiments described herein, the material for the primary structure is preferably elastic or superelastic and examples of such materials include (but are not limited to) titanium alloys (e.g., nitinol), elgiloy, stainless steel, and various polymers. Materials for the secondary coating can include polymeric materials such as polyether ether ketones (PEEK), polyurethanes, a polyetherimides (PEI) such as ULTEM, any of the artificial materials used to form leaflets 1110 and 2110, and others. Leaflets 1110 and 2110 can be fabricated from polymeric materials, including any biostable polyurethanes and polyurethane compositions (e.g., polysiloxane-containing polyurethanes, polysiloxane-containing polyurethane-ureas, etc.) known in the art. Examples of polyurethane-containing leaflets are described in U.S. Pat. Nos. 6,984,700, 7,262,260, 7,365,134, U.S. Patent Publ. No. 2017/0119923 ("Polyurethane/urea Compositions"), and Yilgor et al., "Silicone containing copolymers: Synthesis, properties and applications," Prog. Polym. Sci. (2013), all of which are incorporated by reference herein in their entirety for all purposes. Examples of polyurethane-urea-containing leaflets are described in U.S. Pat. No. 10,266,657, U.S. Patent Publ. No. 2018/0346654, and Dandeniyage, et al. "Development of high strength siloxane poly(urethane-urea) elastomers based on linked macrodiols for heart valve applications," J. Biomed. Mater. Res. Part B, 2018, 106(5), 1712-1720, all of which are incorporated by reference herein in their entirety for all purposes. Materials that approach ideal isotropic, non-creeping characteristics are particularly suitable for use in many embodiments. Leaflets can also be non-artificial and fabricated from biological tissue (e.g., a porcine valve).

In certain embodiments, the polymer used to form the leaflets, all or part of the support structure (e.g., the primary and/or secondary structure), and/or other components of the valve (e.g., an inner liner, outer liner, a seal or sewing cuff as described further herein) is a siloxane polyurethane urea (SiPUU).

In certain embodiments, the SiPUU polymer includes a first segment comprising a structure of Formula I:

$$-A^1-L^1-A^1-  \qquad \text{Formula I}$$

wherein $L^1$ is the residue of a first diisocyanate; and $A^1$ is the residue of a poly($C_1$-$C_{12}$alkane diol);

a second segment comprising the residue of a first siloxane-containing diol;

a third segment comprising the residue of a second siloxane-containing diol; and a fourth segment comprising the residue of a $C_1$-$C_{12}$alkane diamine, wherein the segments are each covalently bonded to each other through the residue of a diisocyanate. In certain embodiments, the polymer includes a plurality of any of the first, second, third, or fourth segments. In certain embodiments, the polymer includes a plurality of each of the first, second, third, and fourth segments.

In certain embodiments, the SiPUU polymer comprises a structure of Formula II:

$$A^4-L^4-A^3-L^3-A^2-L^2-A^1-L^1-A^1-L^2-A^2-L^3-A^3-L^4-A^4 \qquad \text{Formula II}$$

wherein $L^1$ is the residue of a first diisocyanate;

$A^1$ is the residue of a poly($C_1$-$C_{12}$alkane diol);

$L^2$ is the residue of a second diisocyanate;

$A^2$ is selected from -$A^1$-$L^1$-$A^1$-, the residue of a first siloxane-containing diol, the residue of a second siloxane containing diol, and the residue of a $C_1$-$C_{12}$alkane diamine;

$L^3$ is the residue of a third diisocyanate;

$A^3$ is selected from -$A^1$-$L^1$-$A^1$-, the residue of a first siloxane-containing diol, the residue of a second siloxane containing diol, and the residue of a $C_1$-$C_{12}$alkane diamine;

$L^4$ is the residue of a fourth diisocyanate; and $A^4$ is selected from -$A^1$-$L^1$-$A^1$-, the residue of a first siloxane-containing diol, the residue of a second siloxane containing diol, and the residue of a $C_1$-$C_{12}$alkane diamine, provided at least one instance of $A^2$, $A^3$, or $A^4$ is the residue of a second siloxane containing diol; and at least one instance of $A^2$, $A^3$, or $A^4$ is the residue of a $C_1$-$C_{12}$alkane diamine.

In certain embodiments the first diisocyanate, the second diisocyanate, the third diisocyanate, or the fourth diisocyanate is independently selected from 1,4-diisocyanatobutane, 1,12-diisocyanatododecane, 1,6-diisocyantehexane, 1,8-diisocyanateoctane, 4,4'-methylenediphenyl diisocyanate (MDI), 4,4'-methylenebis(cyclohexyl diisocyanate) (H12MDI), p-phenylene diisocyanate (p-PDI), m-phenylene diisocyanate (m-PDI), trans-cyclohexane-1,4-diisocyanate (CHDI) or a mixture of the cis and trans isomers, 1,6-hexamethylene diisocyanate (HDI), 2,4-toluene diisocyanate (2,4-TDI), 2,6-toluene diisocyanate (2,6-TDI), p-tetramethylxylene diisocyanate (p-TMXDI), isophorone diisocyanate or m-tetramethylxylene diisocyanate (m-TMXDI), 1,6-diisocyanatohexane (DICH), 1,3-bis(1-isocyanato-1-methylethyl)benzene, and 1,5-diisocyanatonaphthalene (NDI).

In certain embodiments, the first diisocyanate, the second diisocyanate, the third diisocyanate, and the fourth diisocyanate are the same, for example and preferably, the first diisocyanate, the second diisocyanate, the third diisocyanate, and the fourth diisocyanate are 4,4'-methylenediphenyl diisocyanate (MDI).

In some embodiments, the poly($C_1$-$C_{12}$alkane diol) is selected from poly(hexamethylene oxide), poly(heptamethylene oxide), poly(octamethylene oxide), and poly(decamethylene oxide), preferably the poly($C_1$-$C_{12}$alkane diol) is poly(hexamethylene oxide) (PHMO). In certain embodiments, the molecular weight of the PHMO is from about 660 g/mol to about 760 g/mol, preferably about 713 g/mol.

In certain embodiments, $A^2$ is the residue of a first siloxane-containing diol, for example, the first siloxane-containing diol is a poly(dimethylsiloxane) diol, preferably the first siloxane-containing diol is α,ω-bis-(6-hydroxyethoxypropyl) poly(dimethylsiloxane) (PDMS). In certain embodiments, the molecular weight of the PDMS is from about 950 g/mol to about 1050 g/mol, preferably about 998 g/mol.

In certain embodiments, the second siloxane-containing diol is a disiloxane-containing diol, preferably the second siloxane-containing diol is 1,3 bis-(4-hydroxybutyl)-1,1,3,3-tetramethyldisiloxane (BHTD).

In some embodiments, the $C_1$-$C_{12}$alkane diamine is selected from 1,2-ethylenediamine, 1,3-propanediamine, and 1,4-butanediamine, preferably the $C_1$-$C_{12}$alkane diamine is 1,2-ethylenediamine (EDA).

In certain preferred embodiments, the SiPUU polymer comprises a structure of Formula II or Formula III:

$$A^4-L^4-A^3-L^3-A^2-L^2-A^1-L^1-A^1-L^2-A^2-L^3-A^3-L^4-A^4 \qquad \text{Formula II}$$

$$A^4-L^4-A^2-L^3-A^3-L^2-A^1-L^1-A^1-L^2-A^3-L^3-A^2-L^4-A^4 \qquad \text{Formula III}$$

wherein $L^1$ is the residue of MDI;

$A^1$ is the residue of PHMO;

$L^2$ is the residue of MDI;

$A^2$ is the residue of PDMS;

$L^3$ is the residue of MDI;

$A^3$ is the residue of BHTD;

$L^4$ is the residue of MDI; and $A^4$ is the residue of EDA.

In certain embodiments, the polymer has a number-average molecular weight of at least 100,000 g/mol, for example, from about 100,000 g/mol to about 125,000 g/mol.

In certain embodiments, the polymer has a weight-average molecular weight of at least about 260,000 g/mol, for example, from about 260,000 g/mol to about 355,000 g/mol.

In some embodiments, the polydispersity index of the polymer is ≤3.00, for example, from 2.50 to 3.00.

In certain embodiments, the polymer is from about 20 wt % to about 60 wt % third segments and fourth segments, and the diisocyanate residues bonded to each. In certain embodiments, the polymer comprising Formula II or Formula III is from about 20 wt % to about 60 wt % $A^4$, $L^4$, and $A^3$.

In certain embodiments, has a molecular weight from about 400 g/mol to about 6,000 g/mol.

In certain embodiments, the polymer has an ultimate tensile strength of at least about 20 MPa at about 23° C., for example, an ultimate tensile strength from about 25 MPa to about 50 MPa at about 23° C., from about 30 MPa to about 45 MPa at about 23° C., or from about 30 MPa to about 40 MPa at about 23° C.

Example Embodiments of Prosthetic Valve Manufacturing Involving Leaflet Casting

Numerous embodiments of systems, devices, and methods of manufacturing valves 1000 and 2000 having artificial polymeric leaflets 1110 and 2110 are described herein. These systems, devices, and methods can be applied to any frame geometry or polymer, extending the valve's possible applications to involve the treatment of multiple conditions simultaneously, such as incorporating drug eluting technologies to reduce inflammation due to the foreign body response of the recipient's immune system. In addition, the manufacturing methods described here can be automated and/or robotized for inexpensive and repeatable manufacturing.

Certain manufacturing methods described herein involve the fabrication or receipt of frame 1020, 2020 and then either coupling leaflets 1110, 2110 or valvular body 1040, 2040 thereto, or integrally forming leaflets 1110, 2110 thereon. For ease of discussion, these systems, devices, and methods are described herein with respect to fabrication of a valve 2000 having frame 2020, however it is stressed that all such systems, devices, and methods can likewise be used to fabricate embodiments of valve 1000 and 100. Certain manufacturing embodiments described herein utilize a dip casting or dipping process, however those of ordinary skill in the art will recognize that other comparable formation processes (e.g., molding) can be used instead. Dipping is used because the uniform effect of gravity onto the polymer as it cures ensures that the resulting mold is created at the lowest energy state of the polymer. This eliminates stress concentrations in the macro and micro-structure of the polymer that can result from other common molding techniques such as injection molding, thus greatly extending the valve's lifespan.

The use of these dipping techniques in addition to the use of a contractable frame structure more readily allows valve 2000, 1000, 100 to be implanted in a minimally-invasive catheter based procedure because the frame will retain the ability to be contracted or crimped into a smaller diameter than its resting size. In one embodiment, the frame cells 1155, 1255 are designed in a way to limit the elastic stretch of the polymer. For instance, a fully expanded cell 1155, 1255 might be 8 millimeters (mm) in length and that same cell fully crimped may be 9.5 mm in length, therefore imparting 15% strain on the polymer. When designing the frame cell structure, it may be preferable to keep well under the limit of plastic deformation of the polymer to minimize deformation in the material.

Figure 6A:
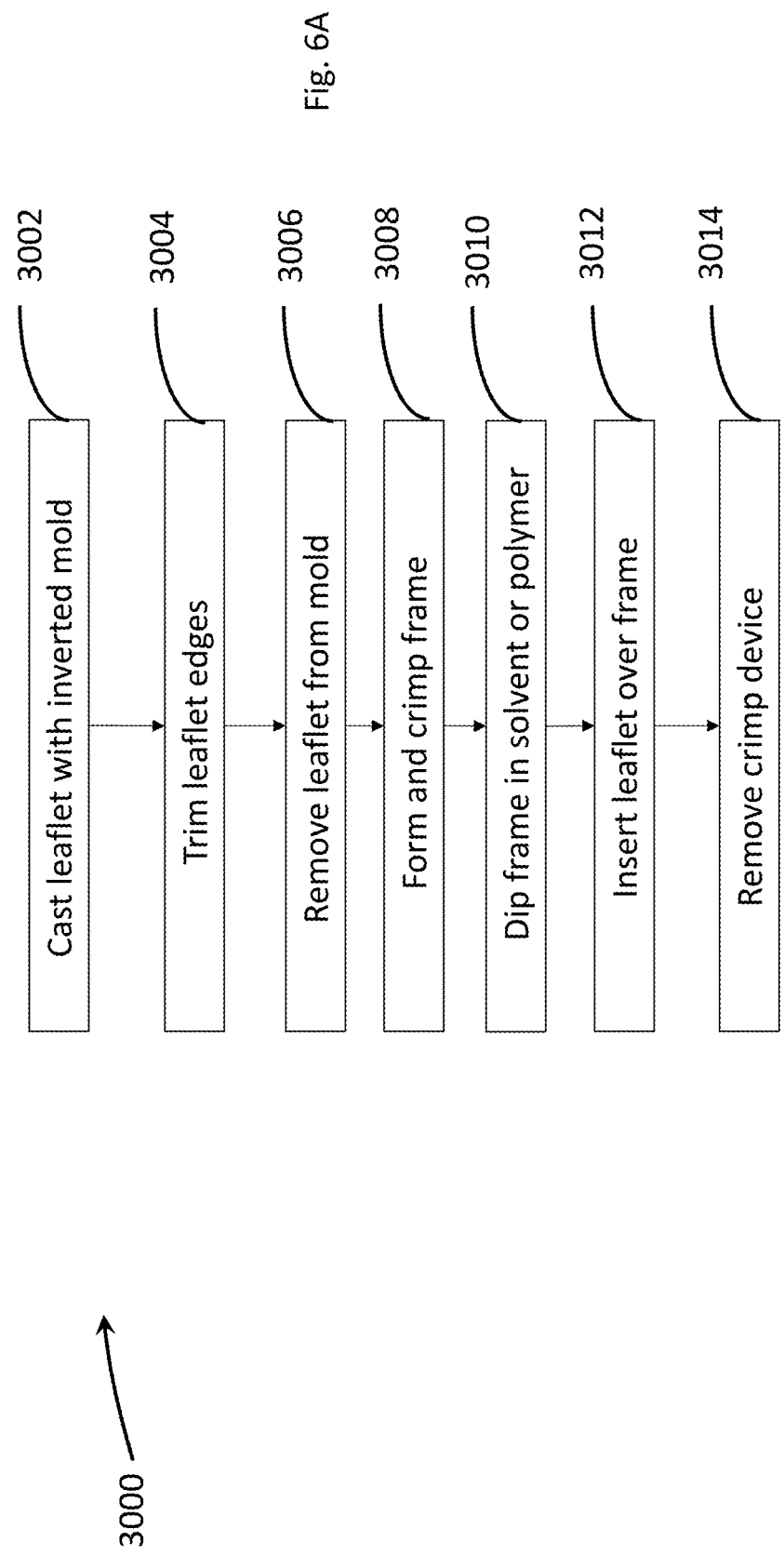
FIG. 6A is a flow diagram depicting an example embodiment of a method of manufacturing a valve.
Figure 6C:
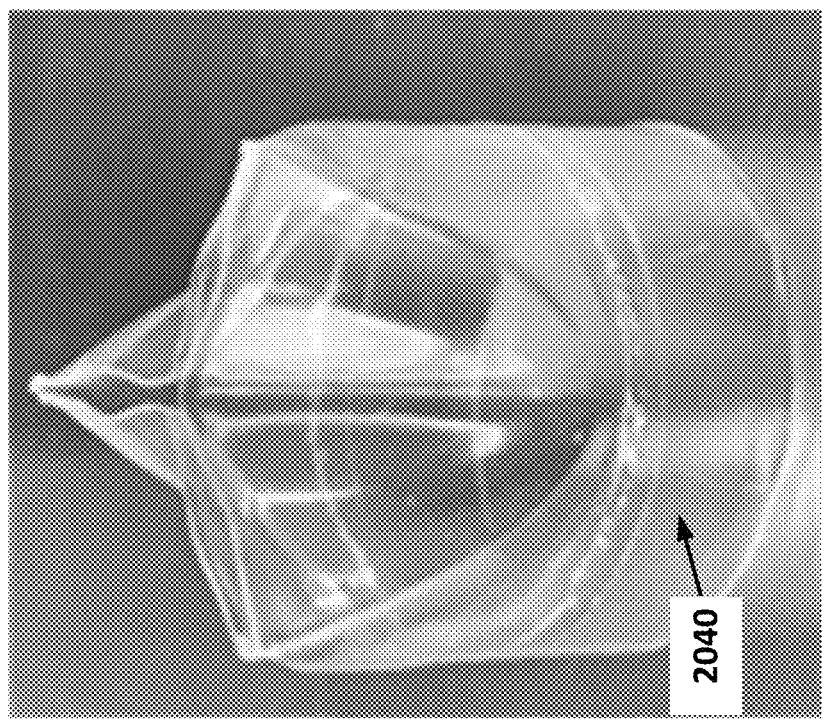
FIGS. 6B-6H are images depicting examples of a valve at various stages of manufacture.
Figure 6B:
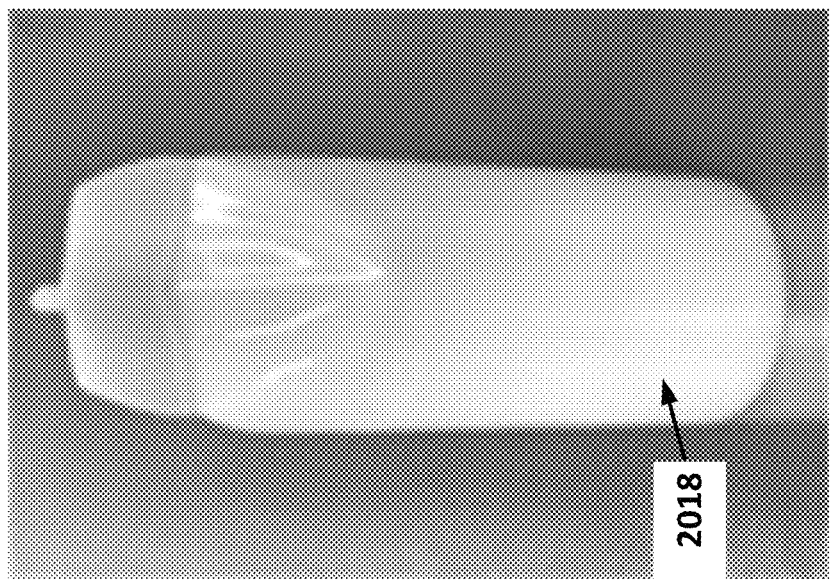
Figure 6E:
Figure 6D:
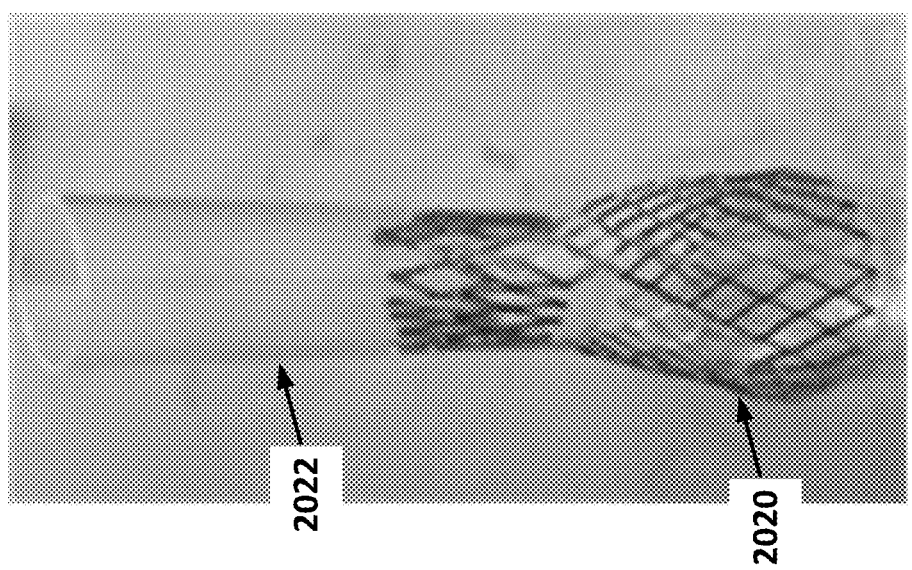

Numerous embodiments of manufacturing a valve are described herein. FIGS. 6A-6H are used to describe an embodiment of manufacturing a valve by placing a polymeric valvular body over a valve frame, embodied as method 3000. FIG. 6A is a flow diagram depicting method 3000 and FIGS. 6B-G illustrates various steps of flow 3000. FIGS. 6A-6G are described concurrently. At 3002, valvular body 2040 with leaflets 2110 is cast with an inverted mold (such as mold 2018 shown in FIG. 6B), which can also be referred to as an internal former or mandrel and can be shaped cylindrically or in any other desired fashion to produce the components of valve 2000. This involves dipping the mandrel in polymer. In this and all dipping stages described herein, the actual movement of the mandrel into the wet polymer can be automated with a computer-controlled device. Unless otherwise stated, as used herein, "dipping" refers to the acts of placing the element to be dipped (e.g., frame, mandrel, valve) into the wet polymer and subsequently removing it. Valvular body 2040 with leaflet 2110 is then cured as part of the casting process at 3002. Leaflet edges are then trimmed, e.g., using an ultrasonic knife at 3004 and then removed from the mandrel at 3006. A cured valvular body 2040 is depicted in FIG. 6C. Frame 2020 is at least partially crimped on the downstream or outflow side at 3008 to enable the cast leaflets 2110 to later be placed over frame 2020. FIG. 6D depicts frame 2020 partially crimped by a tubular member 2022.

Figure 6H:
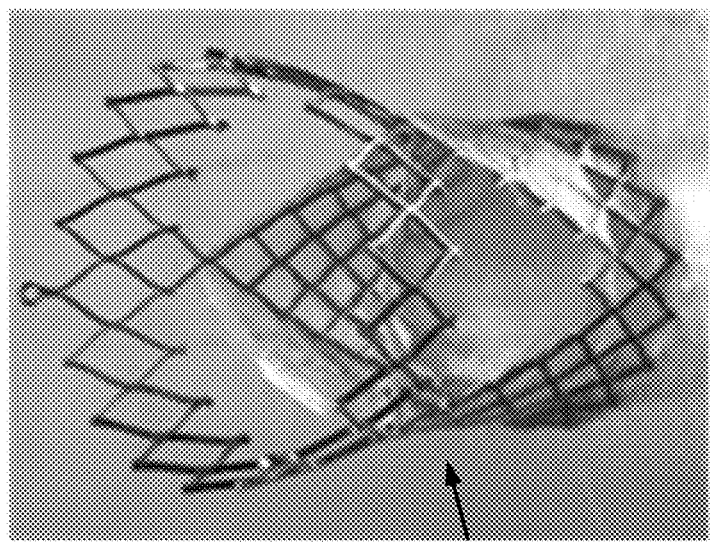
Figure 6G:
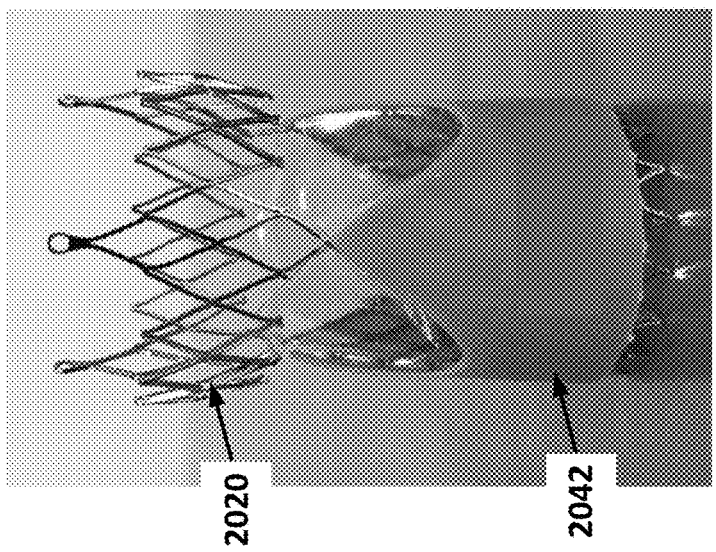
Figure 6F:
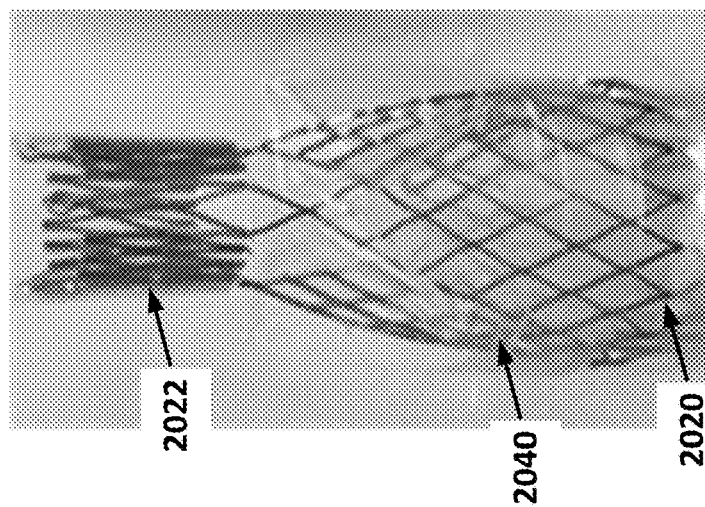

At 3010, frame 2020 is dipped to prepare it for bonding (FIG. 6E), preferably at least an inflow side, in either a strong solvent (e.g., Dimethylacetamide (DMAc)) or a low solid content polymer such as 10% solid polymer or 20% solid polymer. Example polymers include any of those described herein, but are not limited to such. The lower solid content makes the material less viscous. The pre-cast valvular body 2040 with leaflets 2110 is then inserted over the partially contracted or crimped frame 2020 at 3012 and as shown in FIG. 6F. The contracting or crimping apparatus is then removed at 3014. This allows frame 2020 to expand into the cast valvular body 2040 with leaflets 2110 and create a bond between the cast valvular body 2040 with leaflets 2110 and the solvent or low solid content polymer. During curing an external former 2042 (FIG. 6G), with a shape corresponding to the outer diameter of the valvular body (with cutouts for the leaflets), can be used to maintain a close fit between valvular body 2040 and the underlying frame 2020. This process allows for a robust bond while minimizing the contracted or crimped configuration. A finished valve prosthesis 2000 in the expanded state is depicted in FIG. 6H. While method 3000 is described with respect to frame 2020, the method can be applied to frames of differing configurations with side openings for leaflets and thus is not limited to only those frames configured like frame 2020.

Figure 7A:
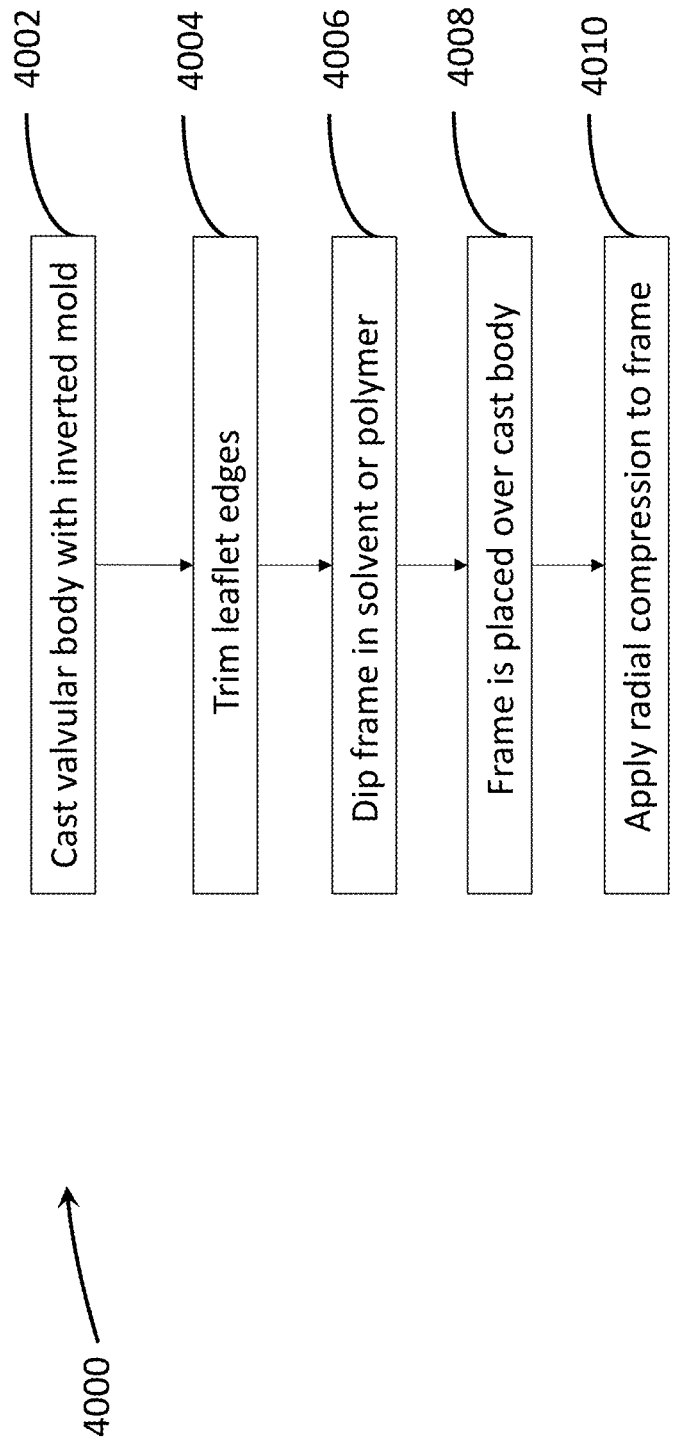
FIG. 7A is a flow diagram depicting an example embodiment of a method of manufacturing a valve.
Figure 7C:
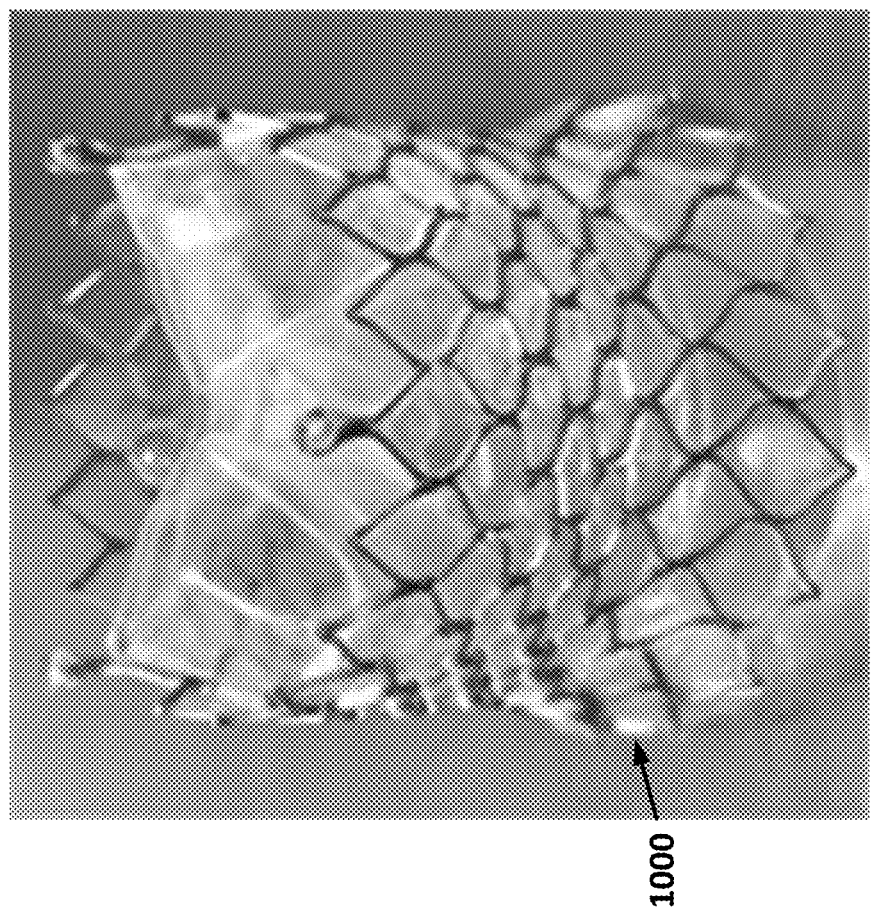
FIGS. 7B-7C are images depicting examples of a valve at various stages of manufacture.
Figure 7B:
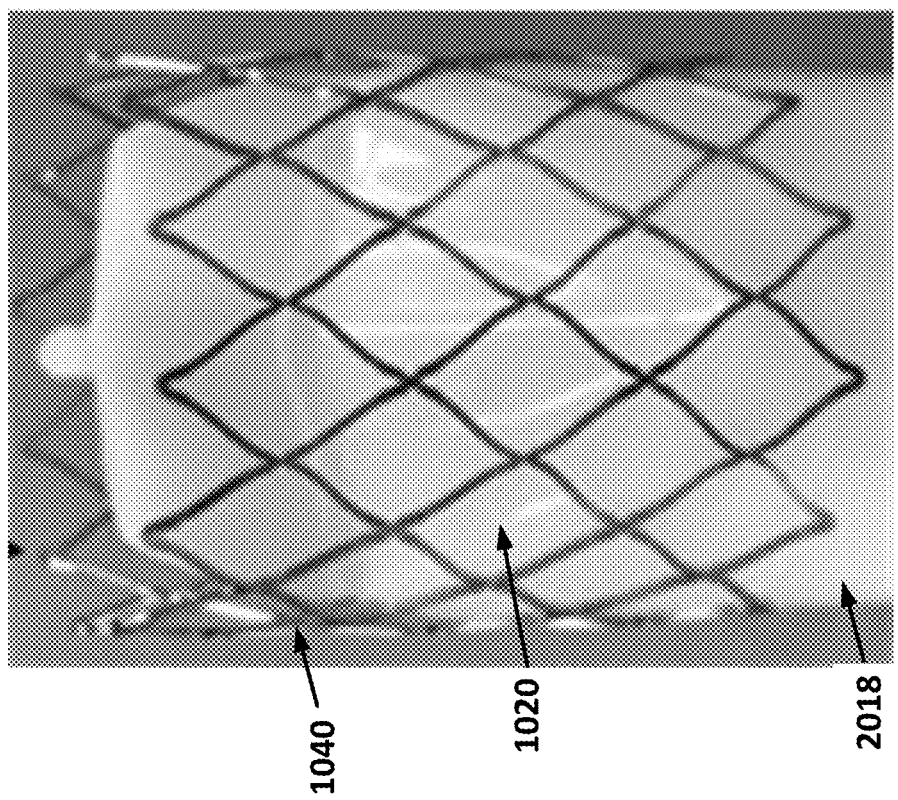

FIGS. 7A-7C are used to describe an embodiment of manufacturing a valve by placing a valve frame over a polymeric valvular body, embodied as method 4000. FIG. 7A is a flow diagram depicting method 4000, and FIGS. 7B-7C illustrate various aspects of method 4000 with photos of an example frame 1020 and valvular body 1040. At 4002, the valvular body 1040 is cast separately by upending a mandrel (e.g., FIG. 6B), dipping it in polymer (e.g., FIG. 6E), and curing it. Then, using an ultrasonic knife, leaflet edges 110 are trimmed in valvular body 1040 at 4004. At 4006, the frame 1020 is dipped to prepare it for bonding, e.g., in either a strong solvent (i.e. DMAc) or a low solid content polymer such as 10% solid polymer or 20% solid polymer. Example polymers could include any of those described herein, but are not limited to such. At 4008, the wet frame 1020 is placed over the cast valvular body 1040. The cast valvular body 1040 can be removed from the mandrel and then the frame 1020 placed over it, or the frame 1020 can be placed over the cast valvular body 1040 while still on the mandrel 2018, as shown in FIG. 7B. At 4010, radial compression is applied from the outside of frame 1020 to force the struts into the cast material and create a robust bond while the frame is still wet. The radial compression can be applied via an external clamp, a specifically designed fixture, or any other method of applying inward radial force (not shown) to create the robust bond between the valvular body 1040 and frame 1020. The prosthesis can be cured while radial compression is applied. FIG. 7C depicts the finalized prosthesis 1000 in the expanded state. While method 4000 is described with respect to frame 1020, the method can be applied to frames of differing configurations with or without side openings for leaflets and thus is not limited to only those frames configured like frame 1020.

Figure 8A:
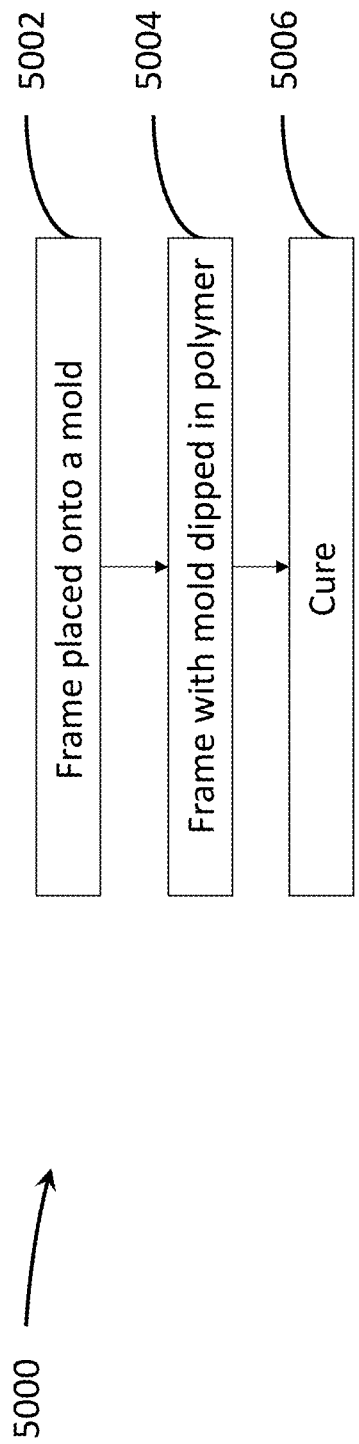
FIG. 8A is a flow diagram depicting an example embodiment of a method of manufacturing a valve.
Figure 8B:
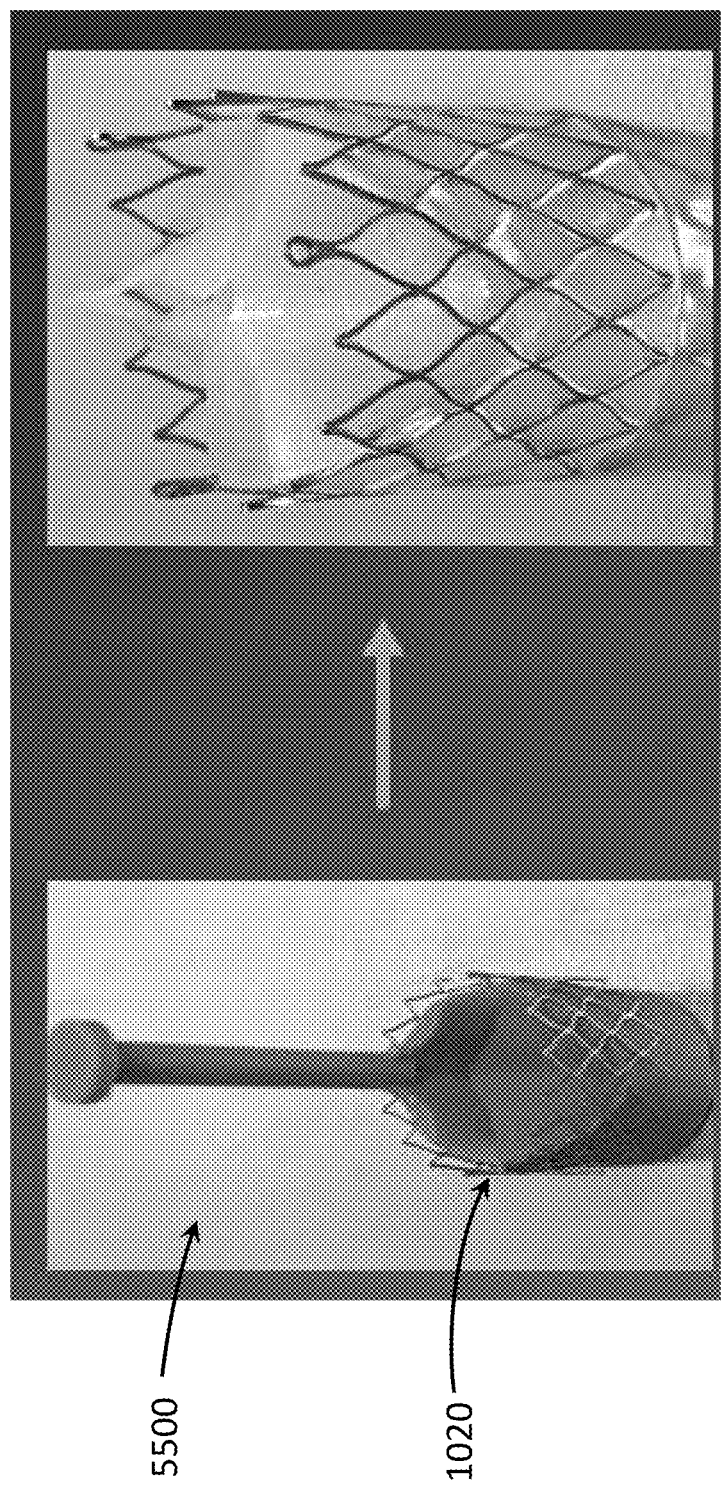
FIG. 8B is a flow diagram depicting an example embodiment of a valve at various stages of manufacture.

FIGS. 8A-8B are used to describe an embodiment of manufacturing a valve by forming the polymeric valvular body directly on the valve frame. FIG. 8A is a flow diagram depicting method 5000, and FIG. 8B illustrates some of the steps of method 5000 with photos. At 5002, a bare frame 1020 is placed onto a mandrel and, at 5004, is dipped into polymer with the outflow side of the valve towards the top of the container, as illustrated at 5500 shown in FIG. 8B. The dipping distance is tightly controlled and is stopped at the point where the leaflet edge is desired. Following this step, the valve 1000 is cured as normal at 5006. After curing, the leaflet 110 does not require trimming or altering in any way since the leaflet edge has already been formed by the precise dipping of the leaflet, but the leaflet can optionally be trimmed. While method 5000 is described with respect to frame 1020, the method can be applied to frames of differing configurations with or without side openings for leaflets and thus is not limited to only those frames configured like frame 1020.

Figure 9:
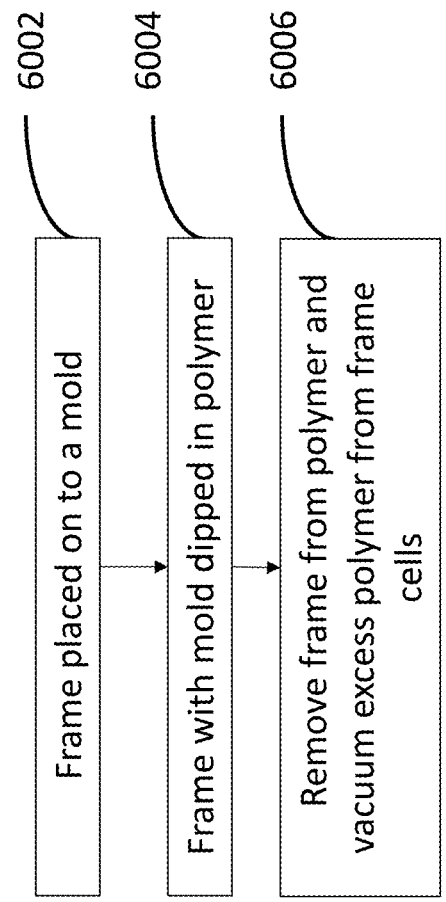
FIG. 9 is a flow diagram depicting an example embodiment of a method of manufacturing a valve.

FIG. 9 is a flow diagram depicting another example embodied as method 6000. This embodiment is for configurations like frame 102 where struts are present in the regions that will pass in front of the coronaries when implanted (e.g., the region generally corresponding to open region 2250 of frame 2200). At 6002 the frame is placed onto a mandrel. The mandrel is dipped in polymer at 6004. Next at 6006, the mandrel is removed from the polymer and vacuum suction is used to remove the excess polymer in the frame cells that are surrounding the leaflets. Alternatively, an inert gas may be used in a blow-off step, where the dipped frame is passed through a low pressure gaseous blade (e.g., nitrogen) which clears out polymer from within the cells but leaves a thin layer on the struts. This can be used to open up frame cells in front of the coronaries to leave open coronary access and un-impeded flow. The structural support of the coronary facing struts help the frame resist deflection under load. Further, a robust polymer coating is formed only on desired cells. Further, protecting, shielding, and masking of leaflets is enabled using secondary mandrel attachments (not shown). The polymer removal techniques of this embodiment can be used with any embodiment herein where polymer is to be removed from open regions of cells.

All method embodiments described herein can be expanded to include formation of sealing skirts in various manners, such as by electrospinning and other techniques. These embodiments can be used in conjunction with any method of forming the valve leaflets and/or any method of attaching the valve leaflets to the frame, regardless of whether those leaflet forming and attachment methods involve dipping, electrospinning, or other processes. For example, each of methods 3000-6000 described with respect to FIGS. 6A-9 can include one or more additional steps of forming an outer liner, forming a sealing skirt, and/or forming an inner liner. Sealing skirt and liner formation can be performed with any of the skirt formation techniques and methods described herein, or other methods not described herein. Each of methods 3000-6000 can include additional steps of finishing (e.g., trimming) any formed polymeric structure performed at the desired point in the methods. All of the methods described herein can be performed with a step of fabricating the frame. All of the methods described herein can be performed with a step of preparing the frame for dipping, electrospinning, or other polymer attachment processes, where preparing the frame includes any one or more of cleaning, washing, rinsing, and/or polishing the frame. All of the methods described herein can be performed with a step of receiving a prefabricated frame.

Example Embodiments of Prosthetic Valve Manufacturing Involving Electrospinning

Provided herein are example embodiments of using electric field assisted spray deposition (e.g., electro-spinning) to form a component of a valve. The polymer can be electrospun directly onto the valve's support structure (either a bare metallic frame or a polymer coated frame) or can be electrospun onto a mandrel or other substrate and then attached to the support structure (where attachment occurs before or after removal from the mandrel). The electrospun component can be any desired polymer component of the valve, such as the leaflets themselves, a sealing skirt, an inner liner, an outer liner, or a sewing cuff (for surgically implanted valves), to name a few. Below is a description for electrospinning of a polymer onto a metal or polymer frame-like structure. Experimentation with an electro-spin coating has shown strong bonding properties necessary for the attachment of any polymeric leaflet or other polymeric structure to the metallic frame or another polymer. This has a number of advantages over traditional dip-casting or molding of polymer for valves such as, for example, improved adhesion of the electrospun polymer to a metallic frame, excellent adhesion of the electrospun polymer to a dipped or cast polymer, and excellent adhesion of permeable electrospun polymer to impermeable electrospun polymer.

Electrospinning involves utilizing a fiber from a polymer substrate to form a desired structure. Electrospinning can use a high electrical current to draw a charged solution of polymer onto a charged collector and can create structures having features on the micron and even nanometer scale. By varying the production parameters, solution conditions, and collector design, various morphologies can be constructed and can be tailored to the desired application. The morphology of the electrospun structure can include, for example, a lattice construct of fibers that can be conformable to abnormal geometries and spikes of calcium typically seen in stenotic heart valves.

The polymer structures that are part of a valve prosthesis (e.g., leaflets, skirts, coatings, sewing cuffs, and the like) can be formed by electrospinning. These electrospun polymer structures can be formed using any type of polymer, including all SiPUU or other polymers described herein, and the type of polymer used for one structure (e.g., the leaflets) can be the same or different from the polymer used to form another structure (e.g., sealing skirt or sewing cuff). Multiple different materials can be used to form each structure as well. The embodiments below are described with respect to dry-spinning (with use of a whipping jet) and wet-spinning (without use of a whipping jet) types of electrospinning, which are familiar to those of ordinary skill in the art. These techniques can be used to electrospin polymers with varying degrees of fluid (e.g., blood) permeability, from impermeable or substantially impermeable polymers to polymers of relatively low or relatively high permeability.

FIG. 10A illustrates an electrospun sealing skirt resulting from a dry-spinning process. The electrospun sealing skirt includes a construct of polymer fibers 10200, which may be referred to as a lattice or web. The construct of polymer fibers 10200 is fabricated from an SiPUU and extends across or bridges the gap within each frame cell (1155, 1255 not shown). The construct of polymer fibers 10200 also extends past the frame and onto the underlying mandrel 10210. This highly porous, conformable polymer material is crimpable, seals irregularities at the annulus, and encourages healthy in-growth of tissue for long term anchoring. This dry-spinning process can also be combined with a wet-spinning process (or the wet spinning process can be used alone) to create an impermeable layer on the inner diameter (ID) of the valve to encourage laminar flow on the inner lumen of the frame, while also creating a robust sealing layer on the outer surface that is in contact with the native annulus.

Figure 10C:
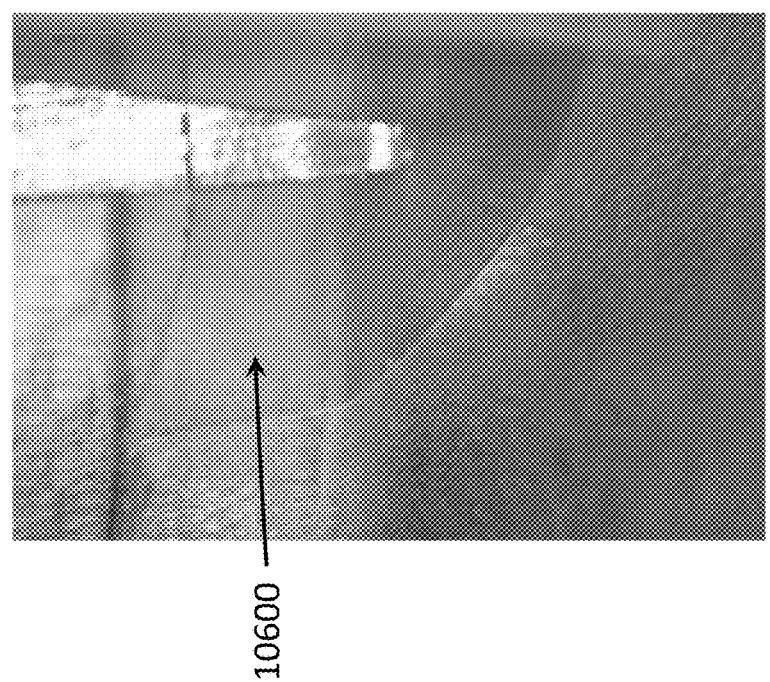
FIG. 10C is an image of a leaflet of a valve in closer detail.
Figure 10B:
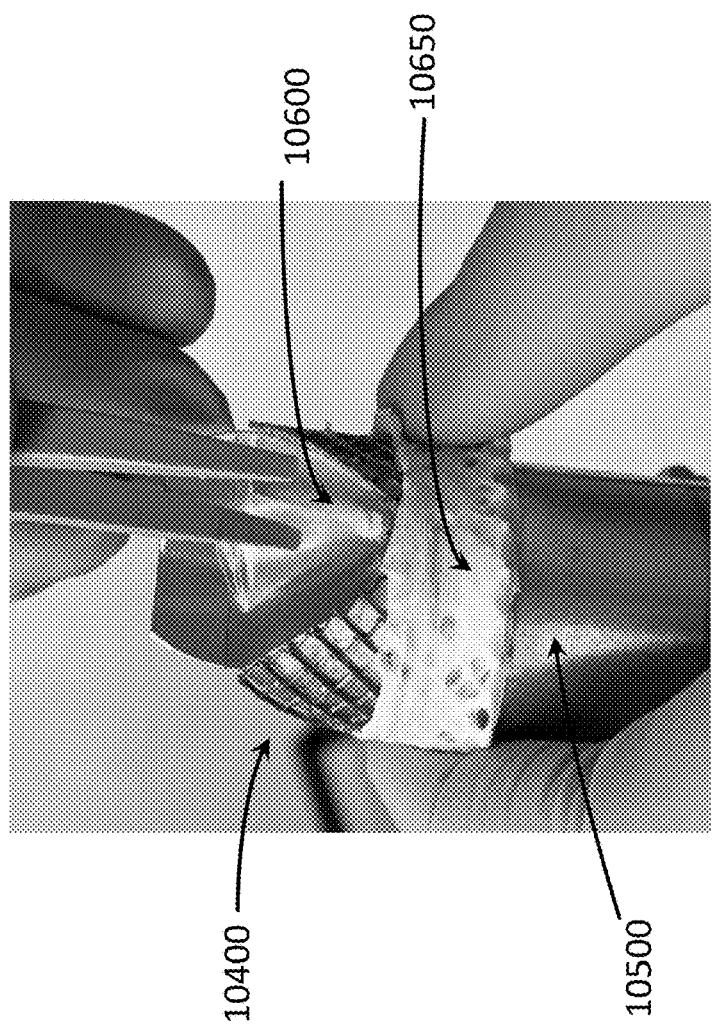
FIG. 10B is an image of an example embodiment of a valve.

FIG. 10B shows an example of a fully electrospun sealing skirt 10650 of a valve 10400 on the electrospinning mandrel 10500. Mandrel 10500 is conductive and can have 3-D concave or convex curvatures for formation of leaflets and any other structures. FIG. 10C is a photograph of leaflet 10600 in closer detail. Here, leaflet 10600 has a uniform thickness across its entirety, however the thickness can also be tailored if desired.

FIG. 10D shows an example embodiment of a valve 10400 with an electrospun sealing skirt 10650 and electrospun leaflets 10800 (three in total, one shown in FIG. 10D). The electrospun leaflet 10800 has a uniform thickness across its entirety. Here, sealing skirt 10650 is applied only to the exterior side along the outer circumference of the frame of valve 10400. In other embodiments, sealing skirt 10650 can be applied to both the interior side along the inner circumference and the exterior side along the outer circumference. In either embodiment, sealing skirt 10650 preferably extends around the entire outer circumference. Sealing skirt 10650 can extend along any longitudinal length (length as measured along the valve parallel to axis of blood flow) of valve 10400. Sealing skirt 10650 can extend from (or from beneath as depicted in FIG. 10D) the inflow terminus 10402 to a position located along the side of valve 10400 between inflow terminus 10402 and (or up to) the base 10403 of leaflet 10800. Here, sealing skirt 10650 extends from positions generally at or further upstream from (beneath as depicted here) terminus 10402 to an intermediate position 10404 between terminus 10402 and base 10403. In other embodiments, sealing skirt 10650 can extend from terminus 10402 to base 10403 (or beyond base 10403 in a further downstream position), can extend from a first intermediate position between terminus 10402 and base 10403 to a second intermediate position between terminus 10402 and base 10403, or from a first intermediate position between terminus 10402 and base 10403 to base 10403 (or beyond). The lower circumferential edge of sealing skirt 10650, beneath 10402 as depicted in FIG. 10D, can be referred to as the inflow edge, and the upper circumferential edge (at 10404) can be referred to as the outflow edge of skirt 10650.

FIG. 10E is a magnified image depicting sealing skirt 10650 in greater detail. In this embodiment, sealing skirt 10650 is a construct of fibers, and the individual polymer fibers 10200 forming the construct can be seen. Here, many fibers have diameters in the range of 2-3 microns (um) and gaps of 20-30 um and more. In any and all embodiments disclosed herein, the fibers can have diameters in the range of 10 nm to 10 um, more preferably in the range of 2 um and greater up to and including 4.5 um, with average gaps of greater than or equal to 27 um. The electrospun sealing skirt 10650 can be formed with any desired thickness with a preferred range of 0.25 mm to 5 mm. All of these are merely examples and those of ordinary skill in the art will recognize in light of this description that fibers of other sizes can likewise be used.

Figure 10G:
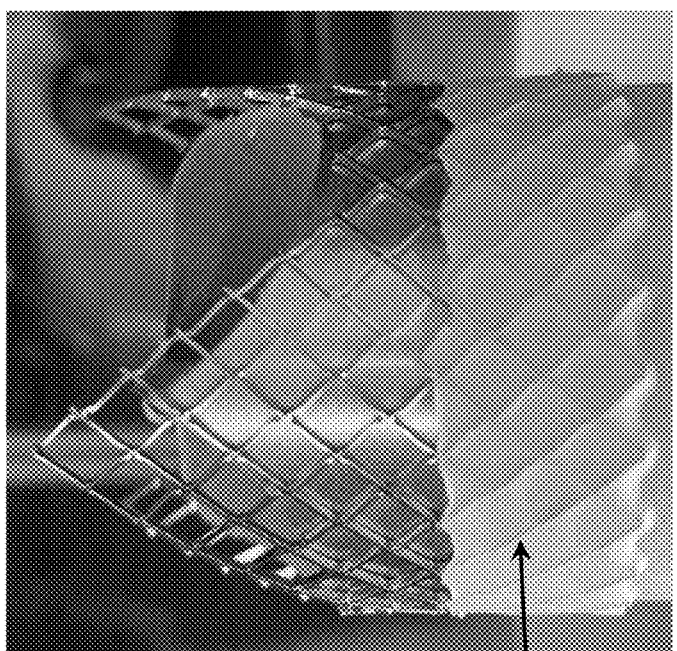
Figure 10F:
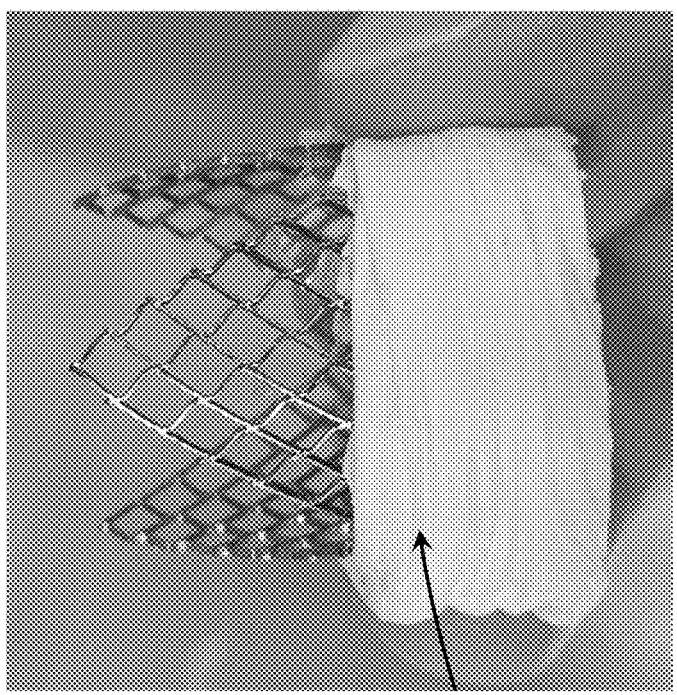

FIG. 10F shows an example of an embodiment of a valve frame with an electrospun sealing skirt 10650 having a relatively thick configuration (thickness being measured laterally perpendicular to the direction of blood flow). For example, the thickness in this embodiment is approximately 5 mm. FIG. 10G shows an example of an embodiment of a valve frame with an electrospun sealing skirt 10650 having a relatively thinner configuration, for example, approximately 0.25 mm. Depending on the desired level of annular sealing needed, the skirt can be tailored to any thickness desired.

FIG. 10H is a photograph depicting an example embodiment of a frame 10700 having an electrospun skirt 10650. Here, frame 10700 has a polymer substrate 10702 located thereon, and skirt 10650 is placed over the frame 10700 and substrate 10702. FIG. 10I depicts another example embodiment where frame 10700 is coupled with an electrospun inner liner 10704. In some embodiments, inner liner 10704 can be formed first, such as on the mandrel, and frame 10700 can then be attached thereto. In other embodiments inner liner 10704 can be formed directly on frame 10700. Inner liner 10704 can act as a solid impermeable inner skirt to prevent blood flow through the frame cells in either direction (either from the inner lumen of frame 10700 (regulated blood flow side) through to the exterior (tissue contacting side) or the reverse direction). Inner line 10704 can also act as a substrate, in addition to the frame itself, to which polymer (either electrospun or otherwise applied) can adhere to, e.g., to which the sealing skirt can adhere to through the frame cells, or to which polymer leaflets can adhere to. Inner liner 10704 can be used with all embodiments disclosed herein.

Figure 10K:
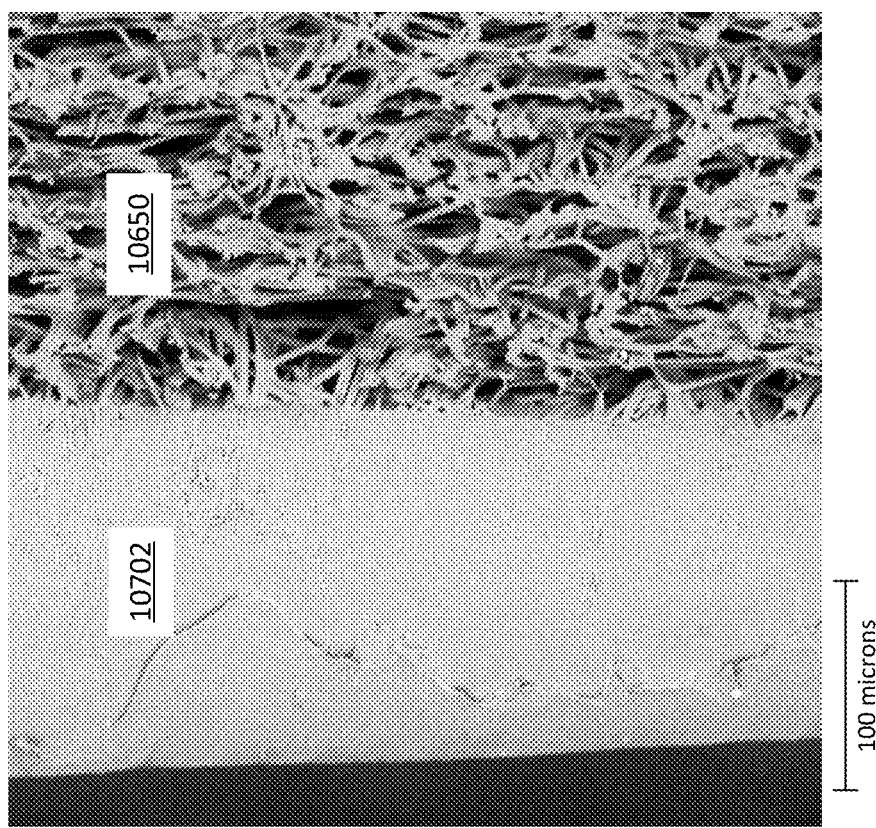
FIG. 10K is a further magnified image of the apparatus of FIG. 10J.
Figure 10J:
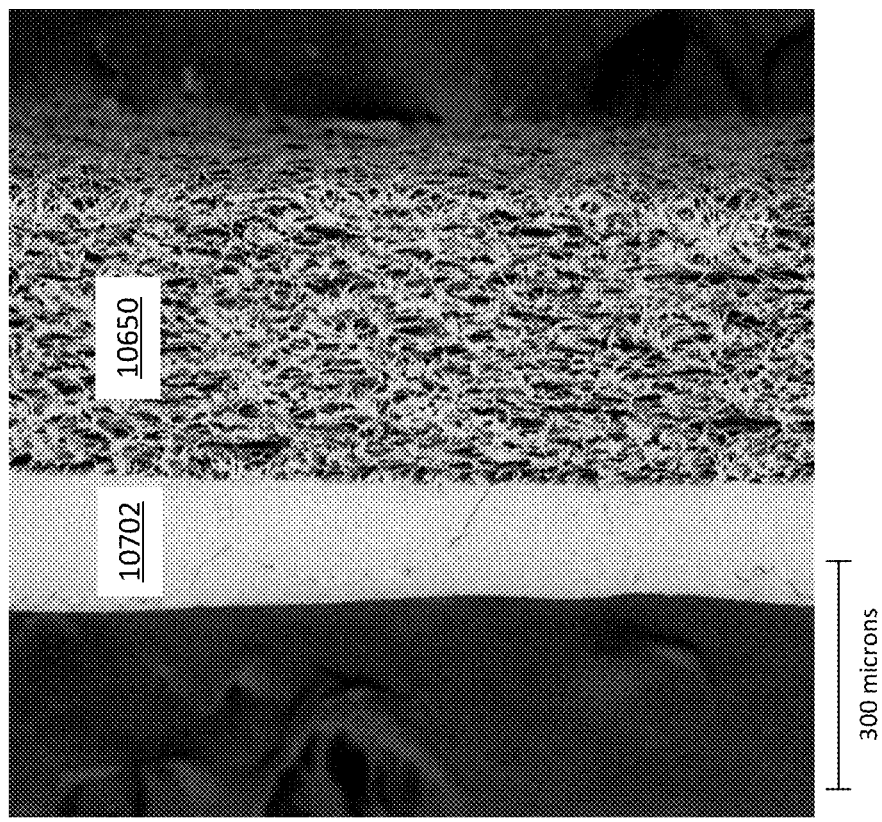
FIG. 10J is a magnified image of a cross-section of a cast polymer in contact with an electrospun polymer.

FIG. 10J is a cross-sectional image showing an example embodiment of an electrospun sealing skirt 10650 adhered to a dipped or cast polymer substrate 10702. FIG. 10K depicts the same structure under greater magnification. The electrospun porous and permeable polymer of skirt 10650 exhibits excellent adhesion to the impermeable polymer of substrate 10702, as can be seen here. Similarly, adequate adhesion can be achieved with dry electrospun permeable polymer coupled to wet electrospun impermeable polymer. Such contact and adhesion can be made in example embodiments when, for example, a permeable electrospun sealing skirt on the outer diameter of the valve bonds to a polymer coating covering the frame itself (e.g., through a dipping or casting process, or by wet electrospinning the covering over the frame), a permeable electrospun sealing skirt on the outer diameter of the valve bonds with a polymeric liner (e.g., a wet electrospun liner) on the inner diameter of a bare metallic frame through the open frame cells of the bare metallic frame, a permeable electrospun sealing skirt on the outer diameter of the valve bonds with a polymer coating covering the frame as well as a polymeric liner (e.g., a wet electrospun liner) on the inner diameter of the coated frame through open frame cells of the coated metallic frame, and others.

Figure 11A:
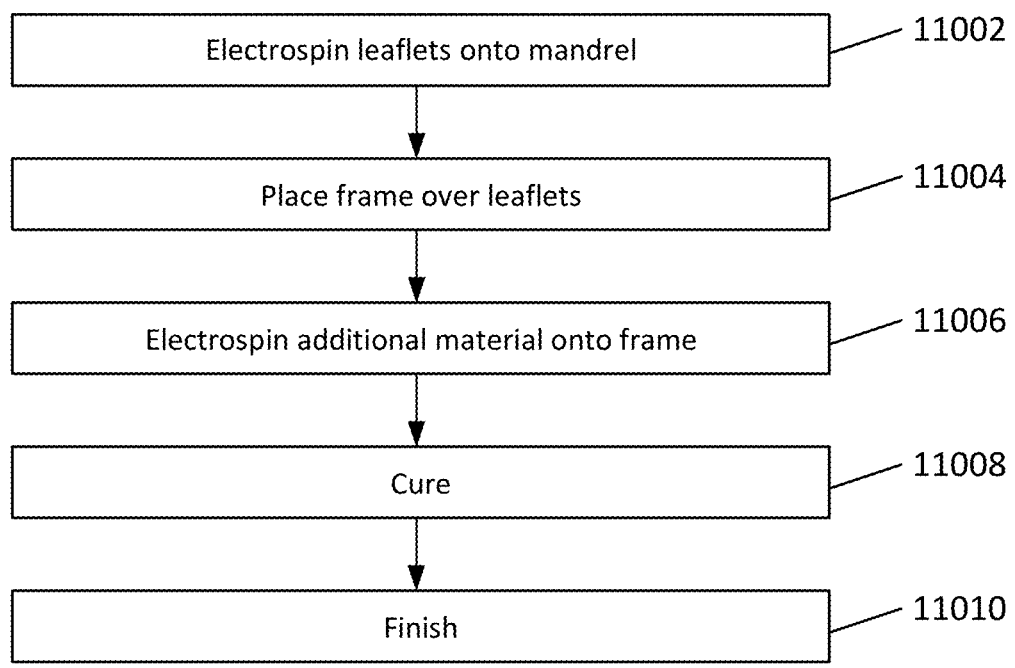
FIGS. 11A-D and 11J are flow diagrams depicting example embodiments of methods of manufacturing a valve.

FIGS. 11A-11D are used to describe example embodiments of manufacturing a valve with an electrospun sealing skirt, such as skirt 10650. FIG. 11A is a flow diagram depicting an example embodiment of an electrospinning process 11000 for manufacturing a portion of a valve prosthesis. The prosthesis is made by first electrospinning the valvular body and/or one or more leaflets onto the mandrel at 11002. This can be, for example, a wet-spun process that forms the valvular body of which each leaflet is a part. The valvular body can then be optionally cured or dried. At 11004, the frame can be placed over the valvular body such that each leaflet is positioned in the correct location with respect to the frame. At 11006, a second amount (e.g., in the form of a layer) of material is electrospun onto the prosthesis to bond the frame to the valvular body or leaflet(s) and also to create the sealing skirt, e.g. 10650 shown in FIG. 10A. At 11008, the prosthesis can be cured to at partially solidify the electrospun portions and/or remove solvent. Curing can be performed in an oven or other temperature and/or humidity controlled environment. At 11010, the prosthesis can be finished, such as by trimming the sealing skirt, trimming the leaflets, and/or sealing edges of the prosthesis (see description with respect to FIGS. 11K-11N herein). Removal of the electrospun valvular body and frame from the mandrel can be assisted by local cooling or heating of the conductive mandrel.

Figure 11B:
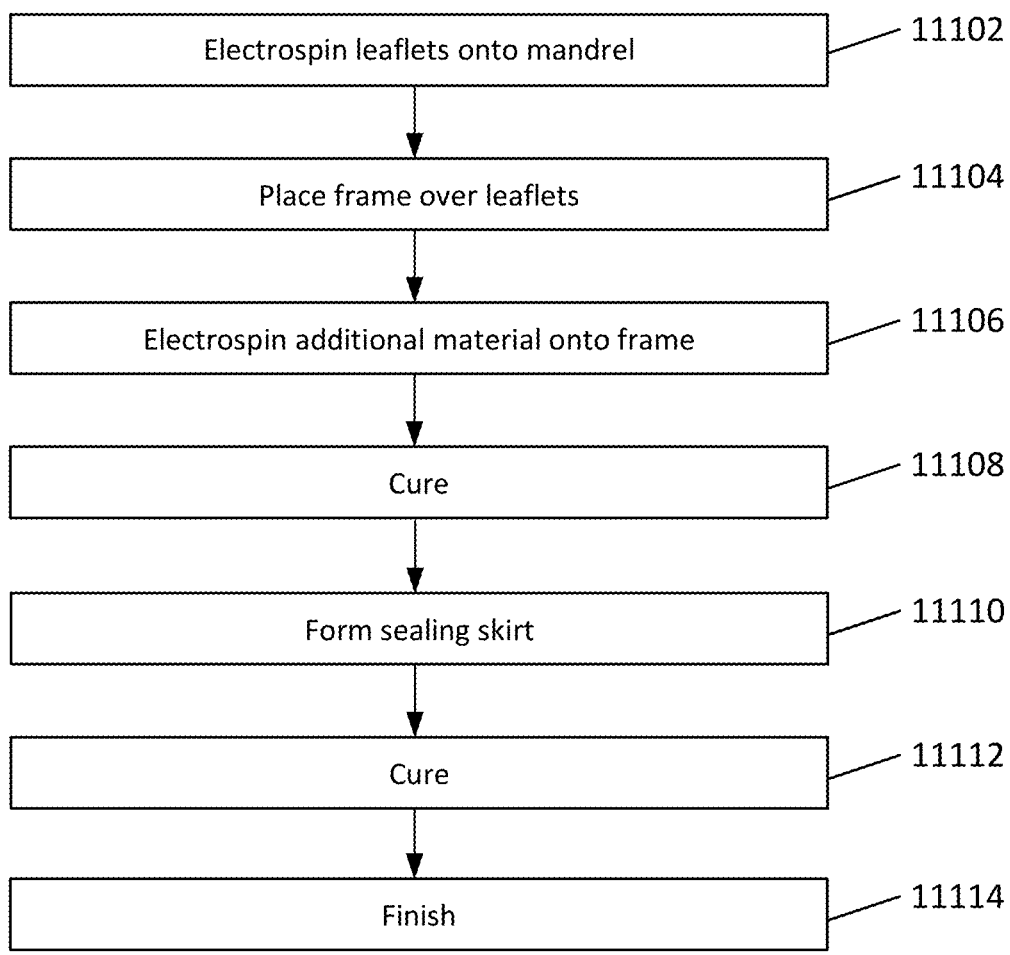

FIG. 11B is a flow diagram depicting another example embodiment of an electrospinning process 11100 for manufacturing a portion of a valve prosthesis. The prosthesis is made by first electrospinning the valvular body and/or one or more leaflets onto the mandrel at 11102. Again, this can be a wet-spun process that forms the valvular body of which each leaflet is a part. At 11104, the frame can be placed over the valvular body such that each leaflet is positioned in the correct location with respect to the frame. At 11106, a second amount (e.g., in the form of a layer) of material is electrospun onto the prosthesis to bond the frame to the valvular body or leaflet(s). In some variations this additional material can be applied by spraying or coating in a manner other than electrospinning. At 11108, the prosthesis is cured to at least partially solidify the electrospun portions and/or remove solvent. Next, at 11110, a sealing skirt can be electrospun onto the cured valve (e.g., the frame and/or polymeric layer). In some variations, step 11108 can be omitted and the process can proceed directly to step 11110. At 11112, the prosthesis can be cured to at least partially solidify the electrospun portions and/or remove solvent. At 11114, the prosthesis can be finished, such as by trimming the sealing skirt, trimming the leaflets, and/or sealing edges of the prosthesis (see description with respect to FIGS. 11K-11N herein).

Figure 11C:
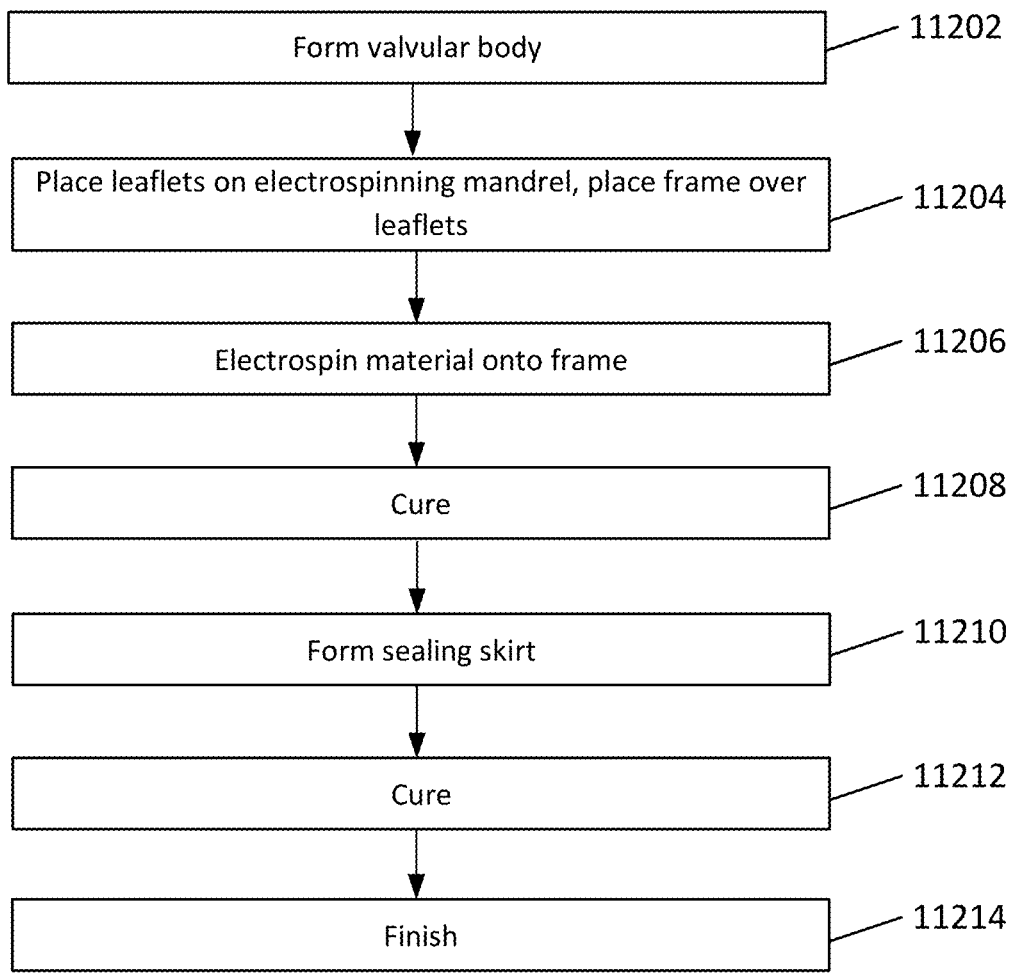

FIG. 11C is a flow diagram depicting another example embodiment of a process 11200 for manufacturing a portion of a valve prosthesis. At 11202, a valvular body having leaflets are formed on a mandrel or other former using a dipping process, e.g., such as those described herein. This step can include curing the leaflets and/or trimming the leaflets to their desired shape. At 11204, the valvular body is removed and placed on a second mandrel for electrospinning (or in some embodiments the same mandrel can be used), and a valve frame is placed over the leaflets. At 11206, polymer is electrospun on the prosthesis to attach the valvular body to the valve frame, or more particularly to attach a portion of the valvular body to the valve frame in a manner that permits movement of the leaflets to perform their blood regulation function. This can be a wet-spin process. In some variations this additional material can be applied by spraying or coating in a manner other than electrospinning. At 11208, the prosthesis is cured to at least partially solidify the electrospun portions and/or remove solvent. Next, at 11210, a sealing skirt can be electrospun on the cured valve (e.g., the frame or electrospun polymer). In some variations, step 11208 can be omitted and the process can proceed directly to step 11210. At 11212, the prosthesis can be cured to at least partially solidify the electrospun portions and/or remove solvent. At 11214, the prosthesis can be finished, such as by trimming the sealing skirt, trimming the leaflets, and/or sealing edges of the prosthesis (see description with respect to FIGS. 11K-11N herein).

Figure 11D:
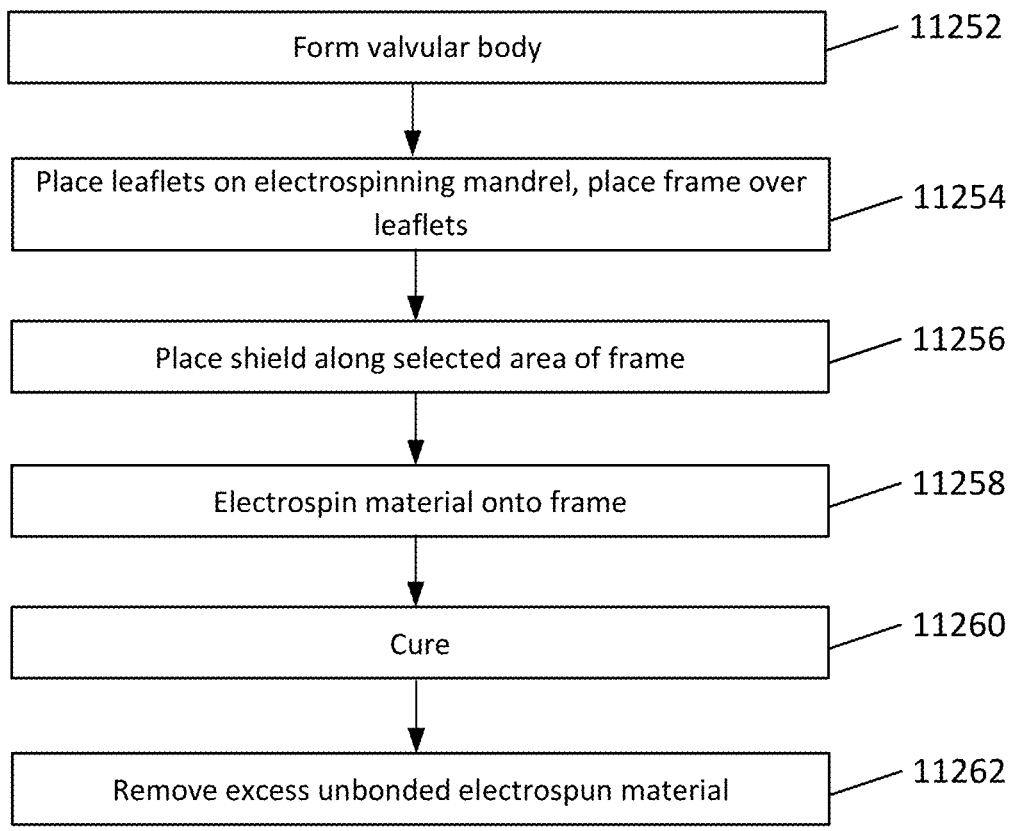

FIG. 11D is a flow diagram depicting another example embodiment of a process 11250 for manufacturing a portion of a valve prosthesis. At 11252, a valvular body having leaflets are formed on a mandrel or other former using a dipping process, e.g., such as those described herein. This step can include curing the leaflets and/or trimming the leaflets to their desired shape. At 11254, the valvular body is removed and placed on a second mandrel for electrospinning (or ins some embodiments the same mandrel can be used), and a valve frame is placed over the valvular body. If necessary, the frame is placed over the valvular body in a manner that aligns the leaflet commissures with corresponding commissure positions on the frame. At 11256, a shield or cover can be placed along the inner diameter (or outer diameter) of the frame in a position over the leaflets, if necessary.

At 11258, an electrospinning step is performed to attach the valvular body to the frame. The electrospinning is performed in a relatively high humidity environment. The relative humidity can be 60% up to and including 100% at a temperature of 20 degrees Celsius (C) up to and including a temperature of 40 degrees C., although the embodiments described herein are not limited to such. The polymer can be electrospun to the frame in a sweeping motion to a region directly over the unshielded valvular body such that the electrospun polymer passes through the open regions of the frame cells and contacts the polymer of the valvular body underneath. The polymer can be electrospun over the entire frame if desired. The electrospinning step can occur for the desired amount of time to achieve the desired bond strength and polymer thickness.

The polymer is electrospun on the prosthesis to attach the valvular body to the valve frame, or more particularly to attach a portion of the valvular body to the valve frame in a manner that permits movement of the leaflets to perform their blood regulation function. This can be a wet-spin process. In some variations this additional material can be applied by spraying or coating in a manner other than electrospinning.

Any leaflet shielding can be removed and the prosthesis, optionally while on the second mandrel, can be subjected to a curing environment (e.g., an oven). At 11260, the prosthesis is cured to at least partially solidify the electrospun portions and/or remove solvent. The prosthesis can be removed from the curing environment and the inflow side of the prosthesis can be trimmed if necessary. The prosthesis can be removed from the frame. Next, at 11262, unbonded electrospun polymer can be removed from the frame. For example, electrospun polymer that did not contact the underlying valvular body, such as electrospun polymer applied over the shielding and/or across coronary openings (e.g., 2250) of the frame embodiment, can be readily removed. A sealing skirt can also be added to the prosthesis if desired and/or further finishing can be performed.

Electrospinning of the polymer in the relatively high humidity environment can lead to strong bonds between polymers, in this case the electrospun polymer and the polymer of the valvular body. With conventional electrospinning, the solvent in the spun polymer would contact the dipped or cast polymer (after passing through openings in the frame) and cause the underlying dipped or cast polymer to disintegrate before fully curing. When electrospinning in this relatively high humidity environment, the solvent binds water and stays in a relatively highly tacky form that remains on the frame. A chemical bond forms between the cast polymer and the tacky electrospun polymer during curing. A mechanical bond forms as the electrospun polymer covers and wraps around the frame and the electrospun tacky polymer bonds to the underlying polymer substrate, in this example the cast polymer. Where there is no underlying substrate, the chemical and mechanical bond does not exist and therefore the electrospun polymer can easily be removed from the frame. While the embodiments described herein are not so limited, the siloxane polyurethane ureas (SiPUUs) described above are particularly suited for use as the electrospun polymer and substrate polymer in the techniques described with respect to FIGS. 11C-11I.

FIG. 11E is an illustration depicting a cross-section of an example embodiment where, prior to curing, substrate polymer 11270 is located on an inner diameter of a frame 11271 and electrospun polymer 11272 has been applied to the outer diameter of frame 11271. The electrospun polymer 11272 penetrates openings in frame 11271 and contacts substrate polymer 11270 (as indicated by the double-sided arrow). FIG. 11F depicts this example embodiment after curing. Here, substrate polymer 11270 has chemically bonded with electrospun polymer 11272 and the two have mechanically bonded with frame 11271 to form bonded structure 11273 in region 11274. No substrate polymer 11270 exists in region 11275, so electrospun polymer 11273 does not chemically bond and can be readily removed from frame 11271, as shown in FIG. 11G.

Figure 11I:
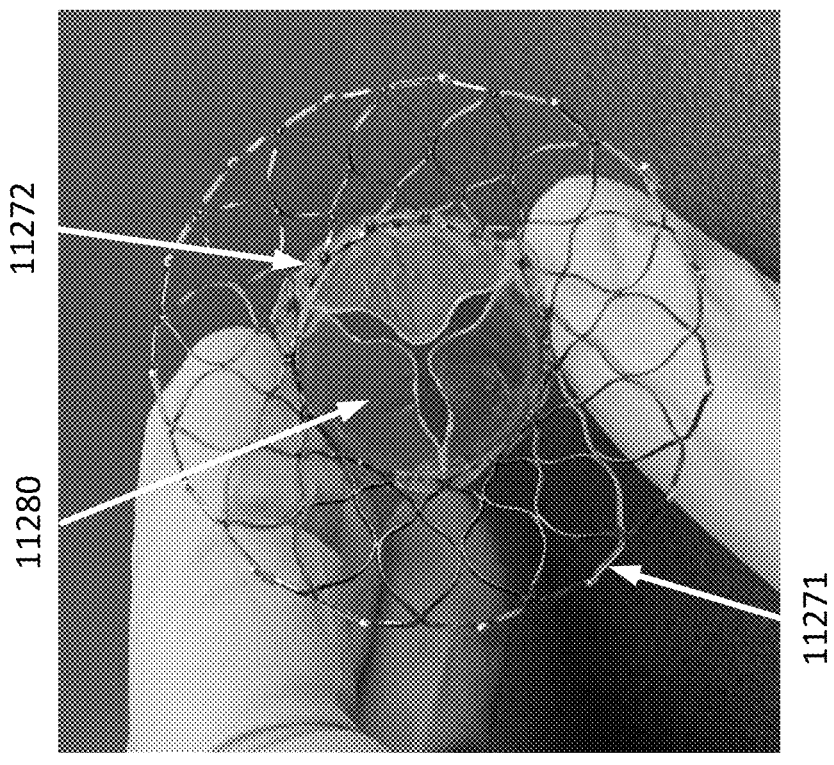
FIGS. 11H-11I are images of an example embodiment of a valve prosthesis at various stages of manufacture.
Figure 11H:
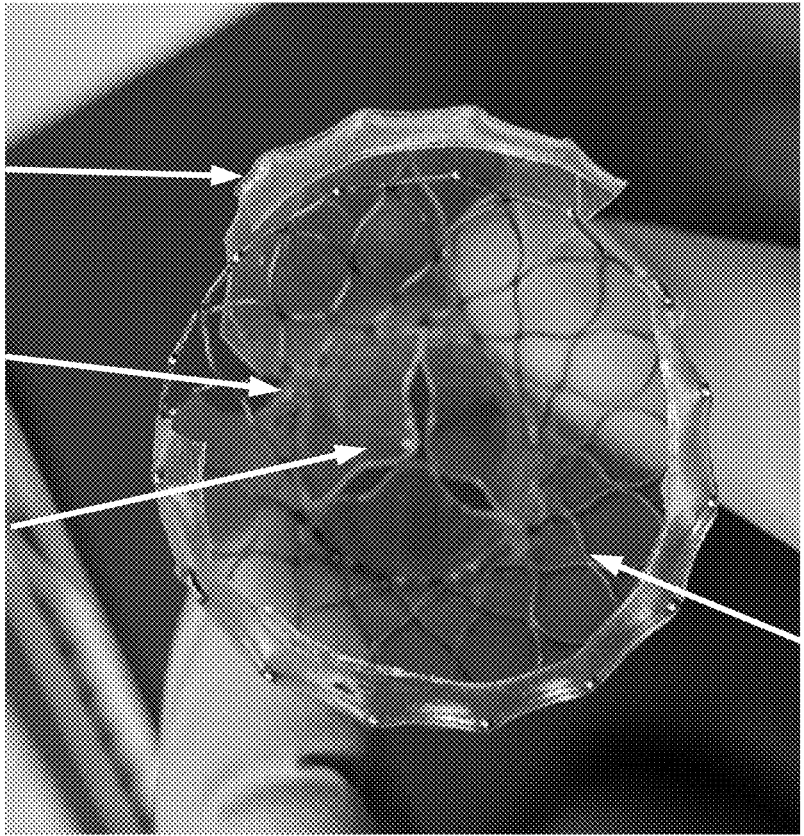

FIG. 11H is an image depicting a top down view of an example embodiment where process 11250 is applied to a frame 11271. Valvular body 11280 is shown at center, and has been cured and bonded to electrospun polymer 11272. Portions of electrospun polymer 11272 in the region adjacent the outflow end of the prosthesis (e.g., region 11275 with reference to FIGS. 11E-G) was applied without contacting substrate polymer, and can be readily removed as indicated by polymer section 11281 detached from frame 11271. The electrospun polymer 11272 in this region can be fully removed using a trimmer (e.g., ultrasonic knife), leaving valvular body 11280 fully bonded to both frame 11271 and the remaining electrospun polymer 11272, as shown in FIG. 11I and as described in step 11262 of FIG. 11D.

Figure 11J:
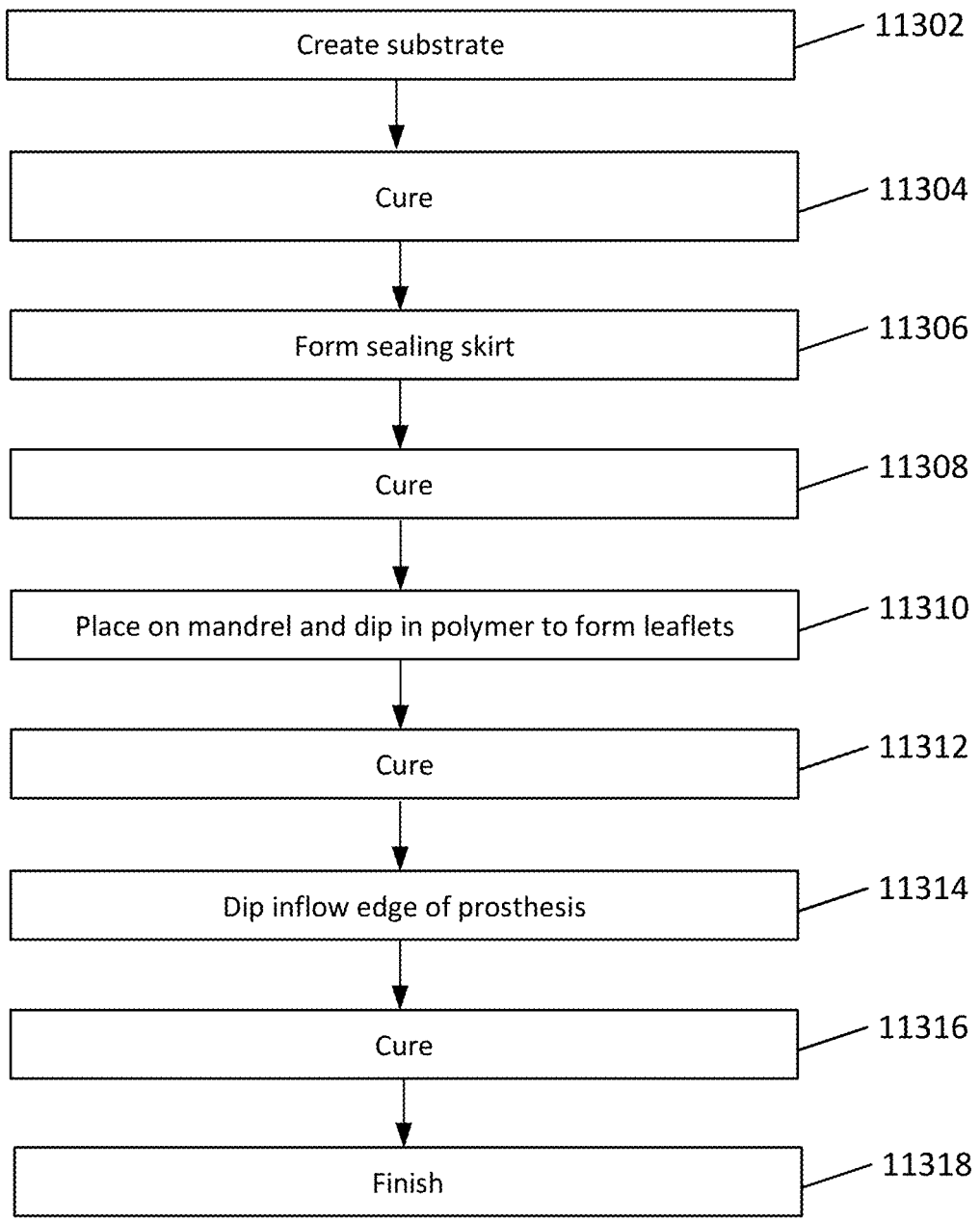

FIG. 11J is a flow diagram depicting another example embodiment of a process 11300 for manufacturing a portion of a valve prosthesis. At 11302, a frame is dipped in liquid polymer to create a substrate on the inflow side of the frame. The substrate can be used later as a base upon which a sealing skirt can be applied. At 11304, the prosthesis is cured to at least partially solidify the polymer and/or remove solvent. At 11306, a sealing skirt can be applied over the substrate, such as by electrospinning. At 11308, the prosthesis can again be cured. The inflow end with the sealing skirt can be trimmed or otherwise finished if desired.

At 11310, the prosthesis can be placed on a leaflet mandrel or other former and dipped into liquid polymer to form the valvular body with leaflets. In this and other embodiments, if the frame is configured with a crown section (e.g., 2500) and open regions adjacent the leaflets (e.g., 2250) then those open regions can be masked or otherwise shielded or covered to prevent polymer from filling or draping over those open regions during the dipping process. Also, in this embodiment the prosthesis, when dipped outflow side first, can be dipped up to and including the outflow edge of the sealing skirt so as to provide a small region of polymer over the sealing skirt's outflow edge, which can bond the edge to the frame and/or otherwise prevent the edge from delamination or detachment. The dipping preferably does not cover the entire sealing skirt so as to permit the sealing skirt to retain its highly conformable nature. At 11312, the prosthesis can be cured to at least partially solidify the polymer and/or remove solvent.

At 11314, the inflow side of the prosthesis can be dipped into polymer to cover the inflow edge of the sealing skirt with polymer (see description with respect to FIGS. 11K-11L below). At 11316, the prosthesis can again be cured. At 11318, the leaflets and other polymeric portions of the prosthesis can be finished (e.g., trimmed). Those of ordinary skill in the art will recognize, upon reading this description, that the curing steps and finishing steps can be performed at various different times, and the curing steps can be consolidated in certain instances as well. As such, the recitation of curing steps at various times should be considered optional.

Figure 11L:
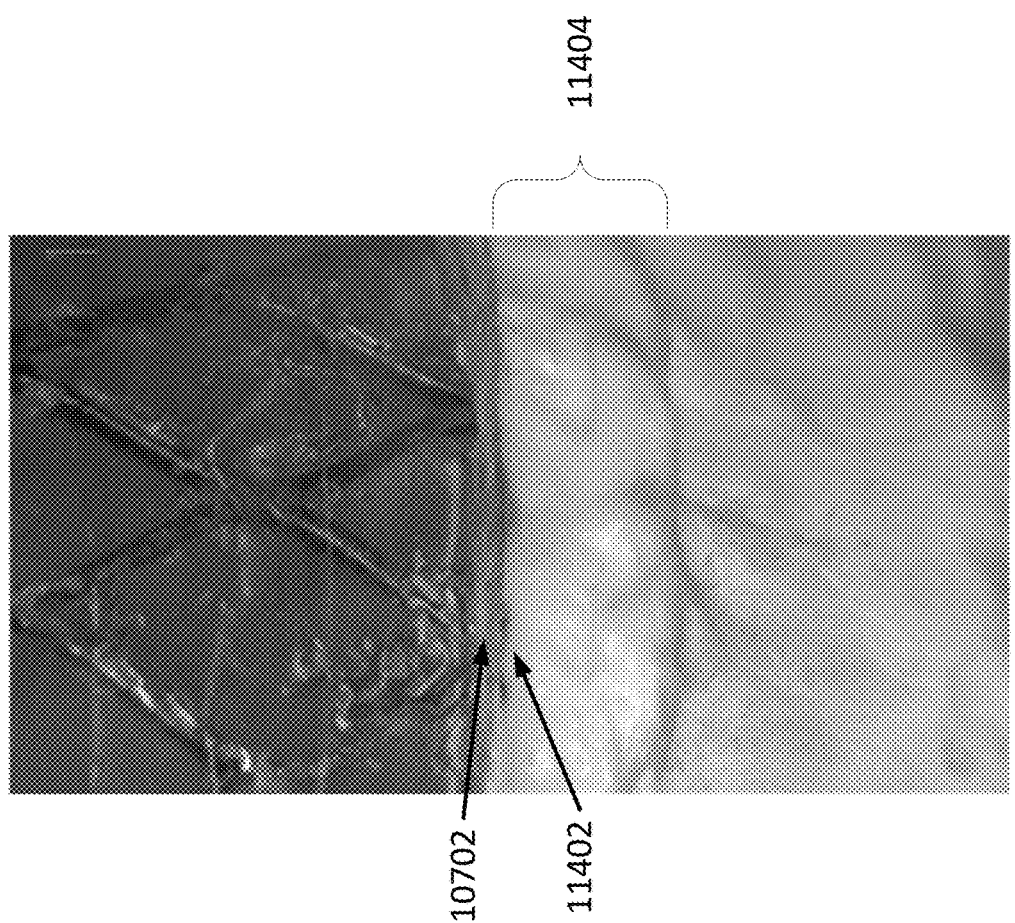
FIGS. 11K-11L are images of an example embodiment of an outflow edge of a sealing skirt before and after heat conditioning, respectively.
Figure 11K:
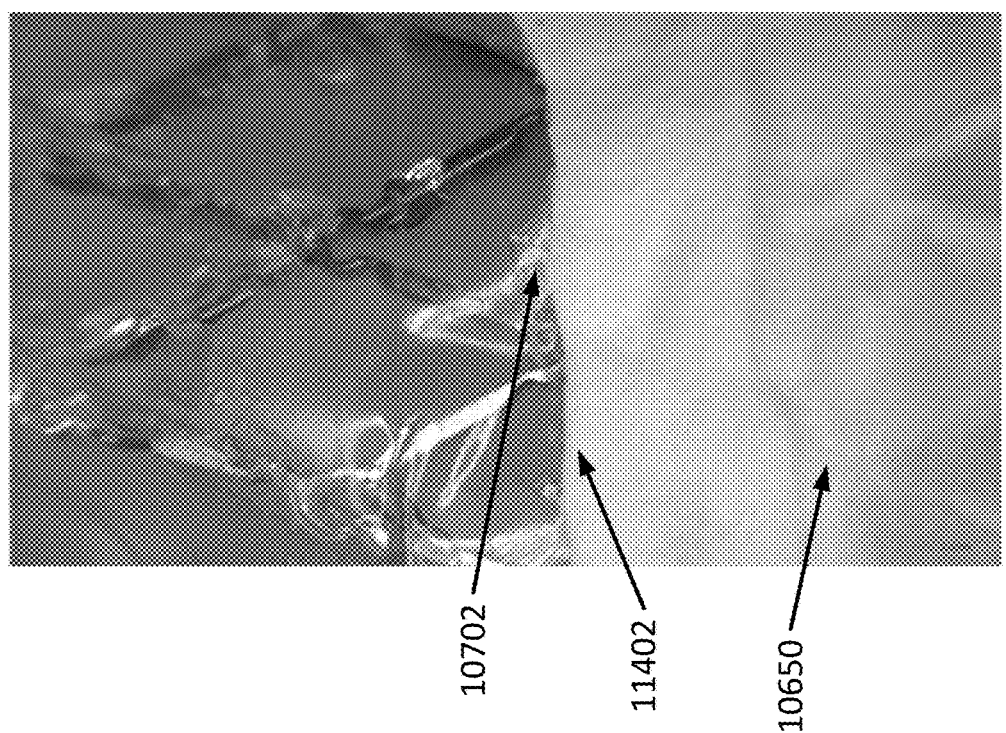

FIGS. 11K-11N are photographs depicting inflow and outflow edges of sealing skirt 10650, and are used to describe embodiments of conditioning those edges against detachment or delamination from the underlying structure (e.g., the frame and/or polymer substrate). FIG. 11K is a magnified view depicting outflow edge 11402 of skirt 10650 prior to conditioning. FIG. 11L depicts outflow edge 11402 after conditioning, which in this embodiment includes the application of heat so as to form a partially or fully melted region 11404 along outflow edge 11402. Application of heat causes skirt 10650 to fuse to the underlying polymer substrate 10702. This leads to an atraumatic edge region 11404 bonded to the underlying polymer that will not delaminate. Heat can be applied with any desired device including a heated filament, a soldering iron, an ultrasonic knife, or others.

Figure 11N:
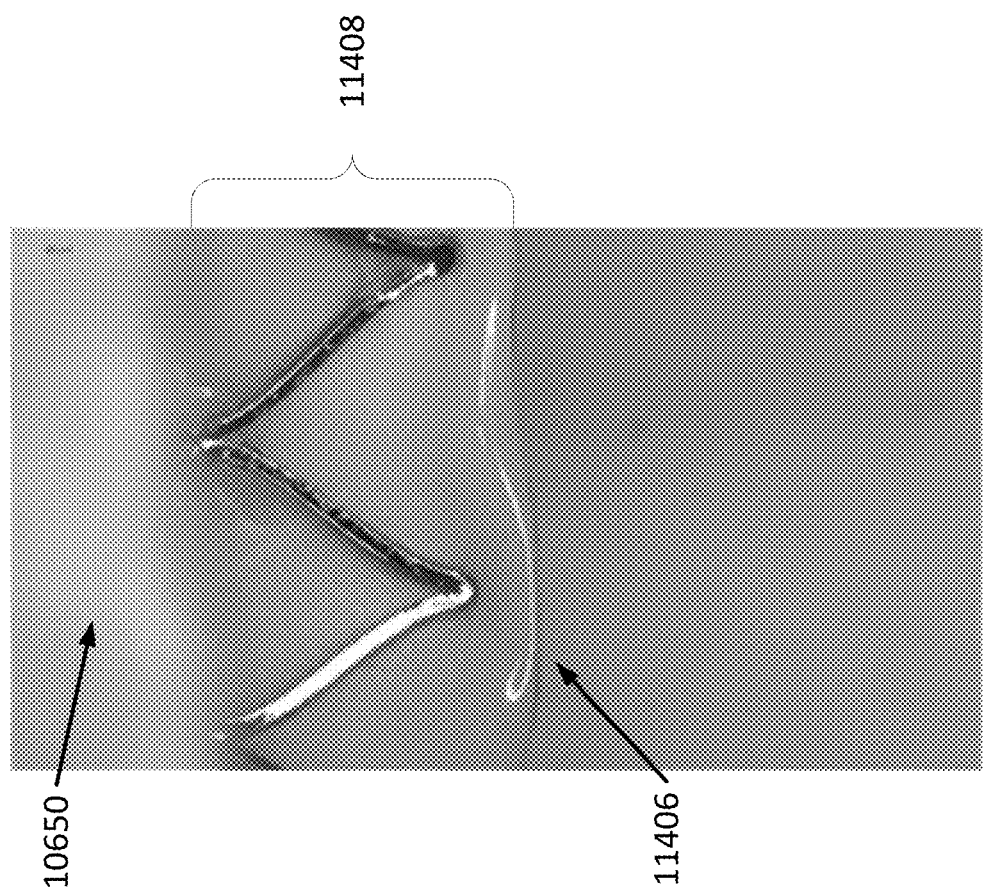
FIGS. 11M-11N are images of an example embodiment of an inflow edge of a sealing skirt after conditioning by polymer dipping, taken from the outer diameter and inner diameter, respectively.
Figure 11M:
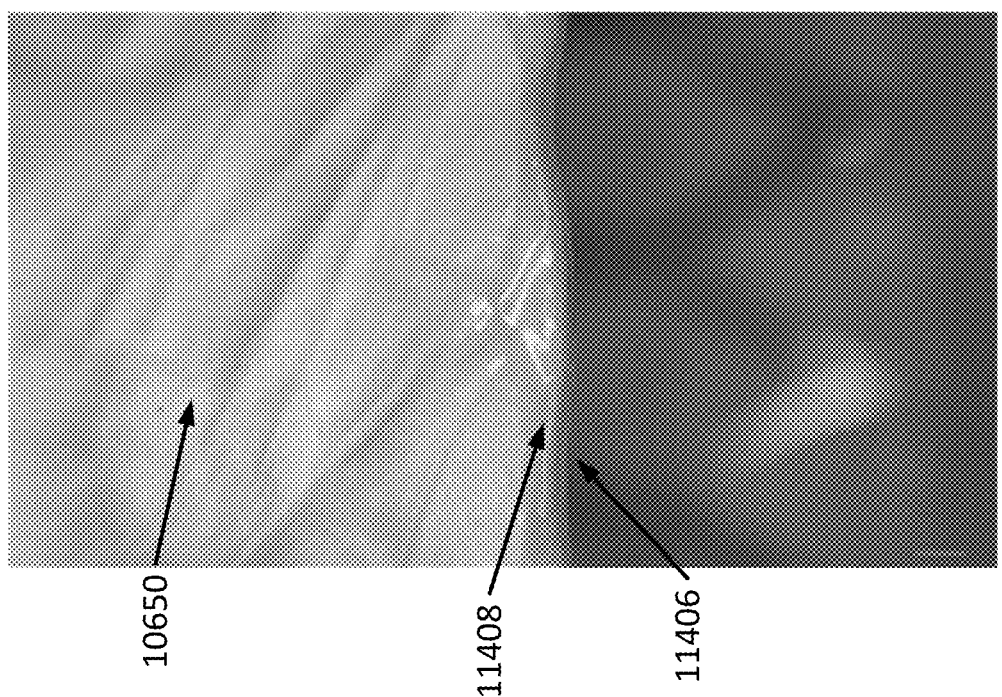

FIGS. 11M-11N are magnified views depicting the outer diameter and inner diameter, respectively, of inflow edge 11406 of skirt 10650 after conditioning, which in this embodiment was dipping or coating with polymer. A coated region 11408 is applied over inflow edge 11406 and bonds skirt 10650 to the underlying polymer substrate and/or frame. This also leads to an atraumatic edge region 11408 that will not delaminate.

Dry electrospinning can form a lattice-like structure that can be 70-90% air, in many examples approximately 80% air, and this range enables improved crimpability and relatively smaller delivery systems as measured in lateral dimension (e.g., French). Density is further reduced. The electrospun structure can be tailored geometrically in size and chemically in composition and/or drug incorporation to aid in the healing response and cell recruitment if desired. Alternatively, the electrospun structure can be applied in a fashion which remains inert and prevents any cell attachment or healing response if desired. The structure may include repeating normalized characteristics and may further include an amorphous web or matrix which may include variable and desired densities. Further, two types of polymers may be spun into the structure. For example, one fiber could form the structural portion and another fiber could include a drug releasing portion, which can be part of the skirt 10650.

In any and all embodiments described herein, the electrospun material can be different types of polymer from that used to form the leaflets and/or valvular body, or the electrospun material can be of the same or similar polymer type used to make the heart valve leaflets or valvular body. When the same polymer type(s) are used for both skirt and leaflets (or valvular body), then one material can be relied upon to create the entire valve and sealing apparatus, with the exception of the frame. This also leads to an even more robust bond and allows the valve to be made in its entirety on the frame using one manufacturing process.

The polymer used to form the leaflets can be selected from the siloxane polyurethane ureas (SiPUUs) described above. In preferred embodiments, the polymer used to form the leaflets comprises a SiPUU as described herein. SiPUUs have been demonstrated to be highly immune to protein deposition, clotting, or other biologic fouling, which is ideal for fabrication of valve leaflets where such deposition and fouling can impede performance. Conversely, those of ordinary skill in the art recognize that a structure for mitigating paravalvular leakage, such as a sealing skirt, should foster protein deposition, clotting, and/or biologic fouling as those mechanisms, by their very nature, act as a seal to the flow of blood, and thus further impede or prevent paravalvular leakage. Thus, those of ordinary skill in the art would not consider SiPUUs for use in mitigating paravalvular leakage.

However, this disclosure provides embodiments where SiPUUs, such as those comprising a structure of Formula I, are used in mitigating paravalvular leakage by forming an electrospun structure (e.g., a sealing skirt) with a densely arranged lattice of fibers, where the electrospun structure itself can promote sealing by, e.g., capturing protein and/or red blood cells thereby activating the fibrin and the healing and tissue ingrowth response. Electrospinning the exterior surface (that in contact with the tissue of the vessel walls) using a dry spinning technique as described herein can facilitate creation of this lattice structure. Furthermore, electrospinning the interior surface (the surface over which blood flows) with a wet spinning technique can result in a relatively smoother or atraumatic lattice surface that does not activate the healing response and also bonds well to the frame itself.

Thus, some advantages of electrospinning a sealing skirt can include: wet spinning for a relatively smooth inner surface and bonding to the frame material (e.g., Nitinol or other nickel-titanium alloys); dry spinning to promote healing, ingrowth, and/or anchoring at the annular region; compressibility, which helps conformity to abnormal geometries; smaller crimp profile; relatively faster application time; and the potential to avoid use of an oven. The skirt may also be trimmed via wet jet.

Advantages of electrospinning a leaflet can include: consistent wall thickness; fast application time; robust attachment; leaflet trimming via wet jet; and potential for single process valve manufacturing when the leaflet and skirt polymers are the same or similar.

Examples of Sponge-Like Polymers and Related Methods of Manufacturing

Figure 12B:
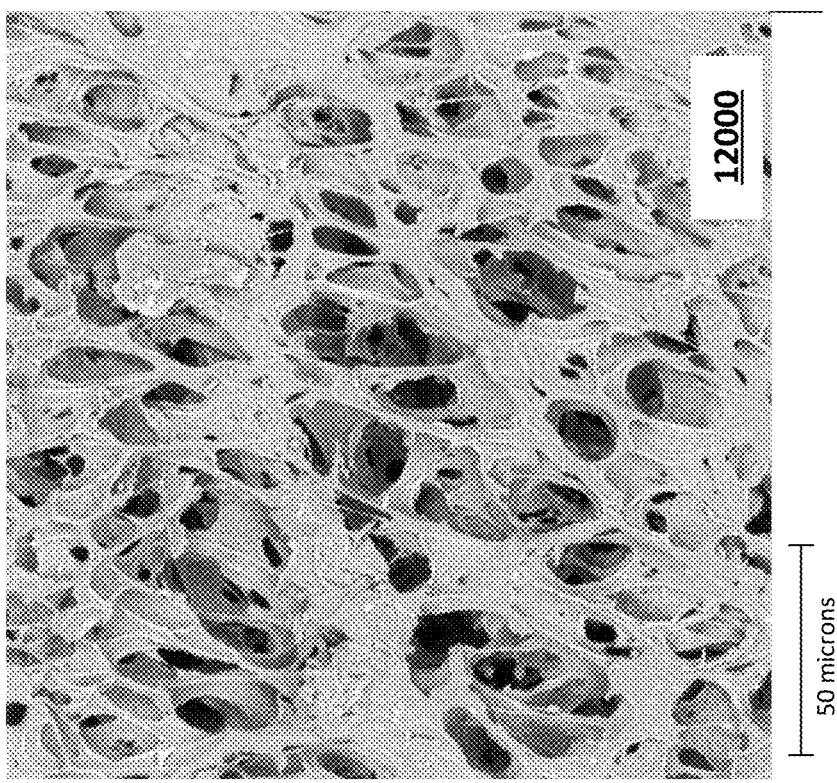
FIGS. 12A-12D are photographs of example embodiments of sponge-like polymers.
Figure 12A:
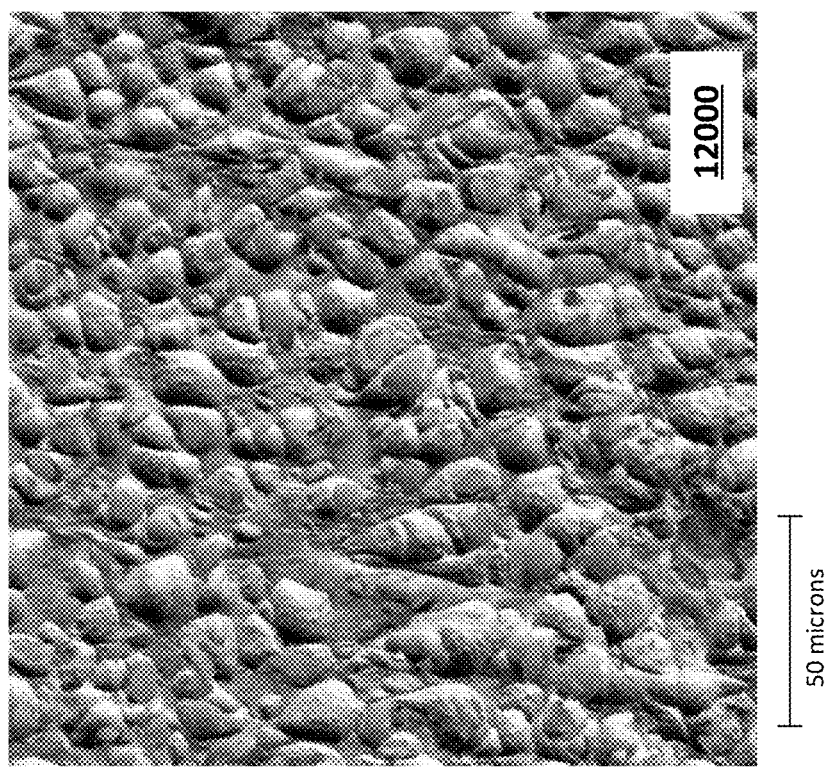
Figure 12D:
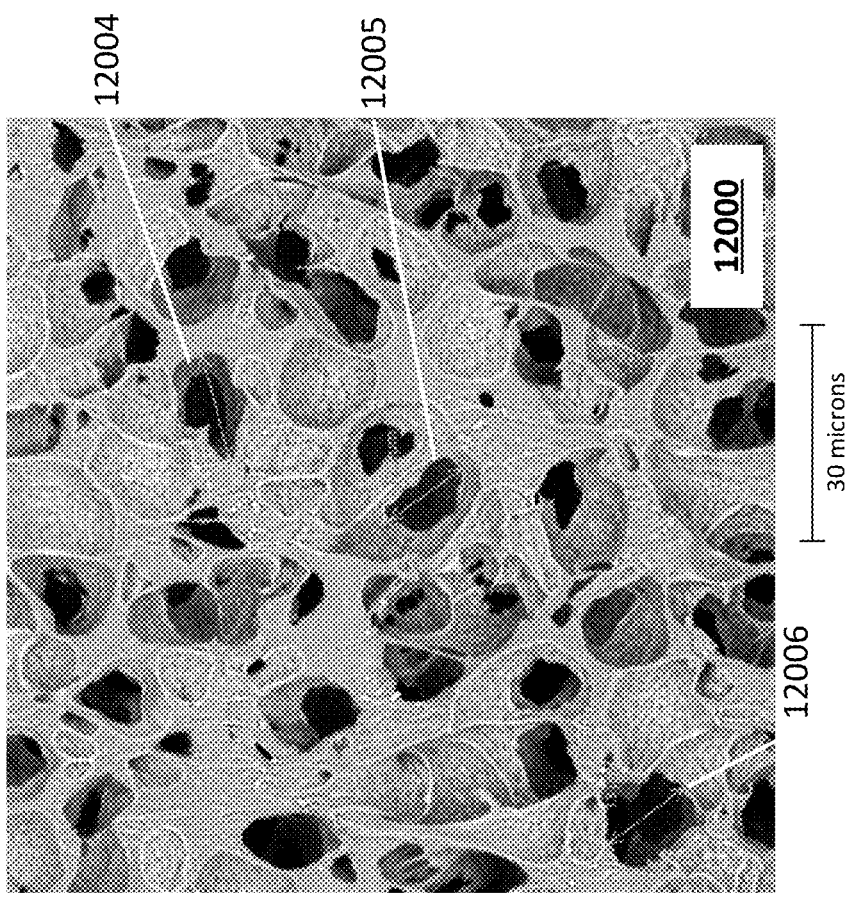
Figure 12C:
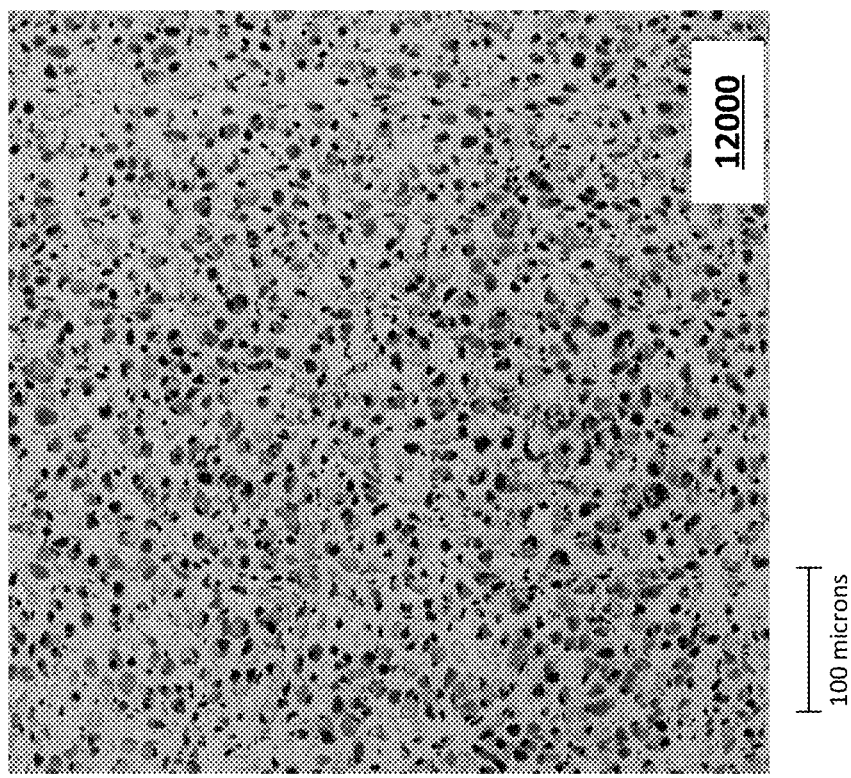
Figure 13B:
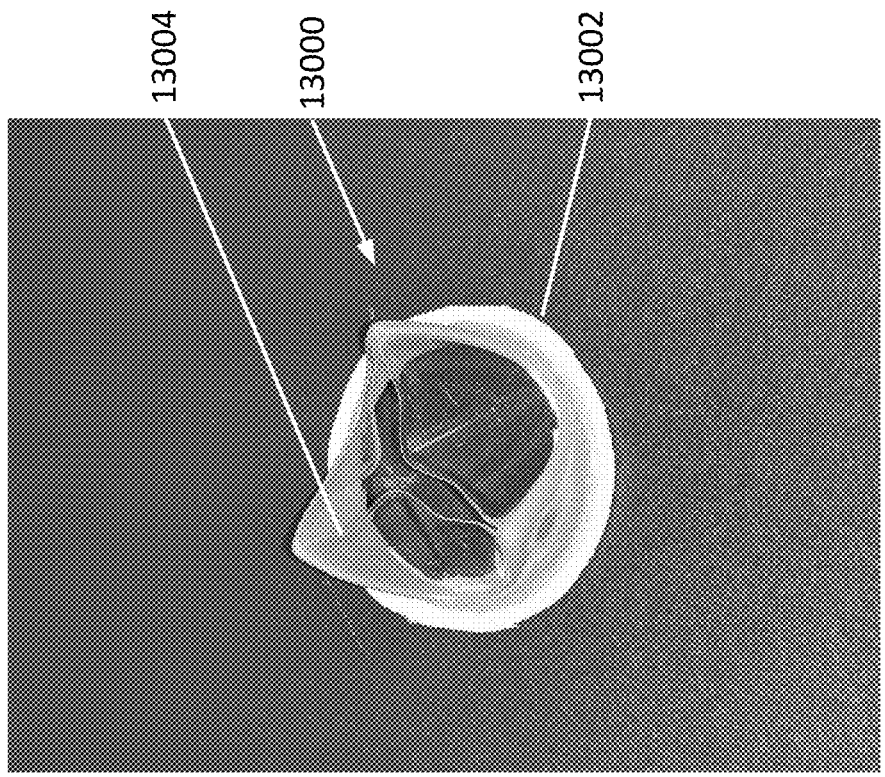
FIGS. 13A-D are photographs of an example embodiment of a surgical valve having a sewing cuff.
Figure 13A:
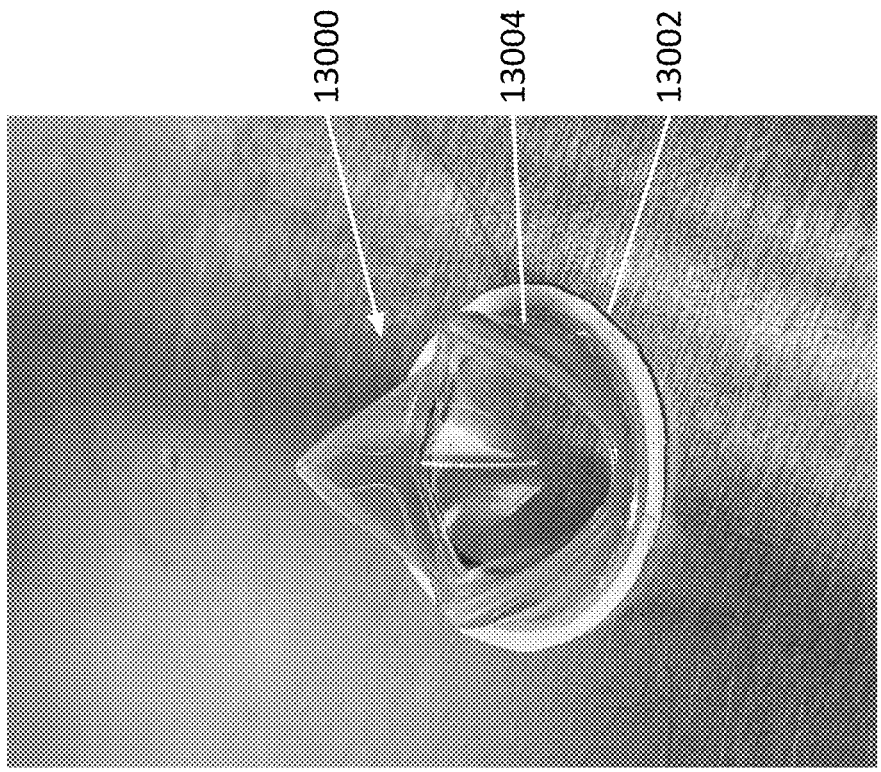
Figure 13D:
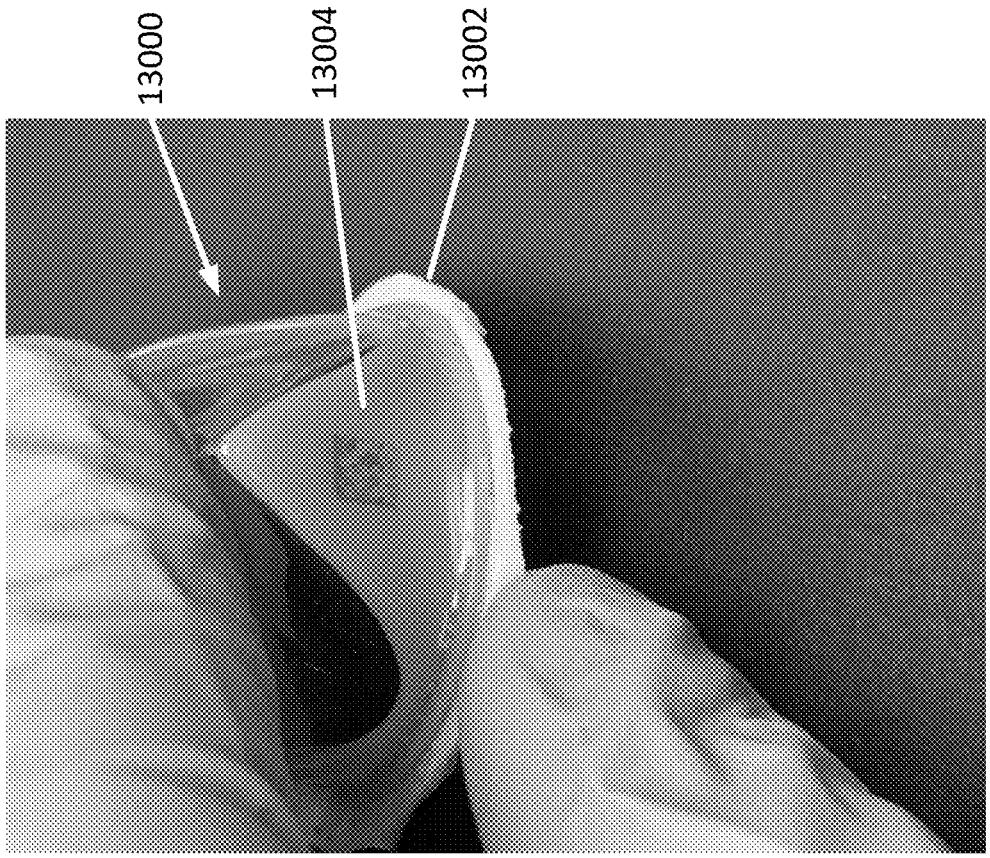
Figure 13C:
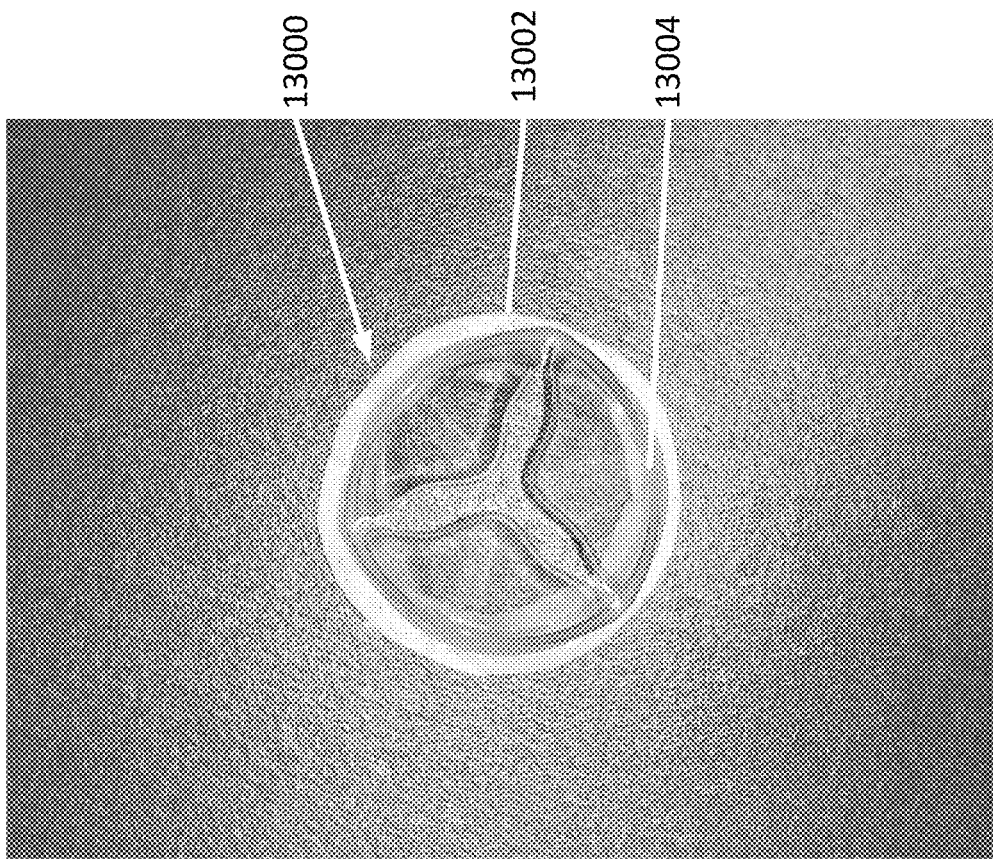

Also described herein are sponge or sponge-like polymers that are highly conformable and can be advantageously used in construction of a valve prosthesis. FIGS. 12A-12D are photographs of example embodiments of sponge or sponge-like polymers 12000. FIG. 12A depicts an example embodiment of sponge 12000 having a non-porous, rough exterior surface. FIG. 12B depicts an example embodiment of sponge 12000 having a more porous configuration. FIG. 12C is a macroscopic view of a highly porous sponge and FIG. 12D is a higher magnification of the sponge of FIG. 12C.

As can be seen, sponge 12000 includes multiple individual cells (also referred to as pores or microcells) 12002 of varying size that together form a matrix of cells. A significant percentage of cells can be open as depicted in FIGS. 12B-12D to impart both compressibility and conformability to the structure, which in turn makes the structure suited for use as a seal (e.g., a sealing skirt or sewing cuff) for mitigating paravalvular leakage. Open cells also make the structure porous or semi-porous to blood and tissue, which facilitates protein capture, thrombogenesis and tissue ingrowth, which in turn assists in mitigating leakage and anchoring the structure to the surrounding tissue. The percentage and size of open cells contributes to the degree of compressibility and conformability of the structure, and processing parameters can be adjusted to vary the relative percentage of open cells. Examples embodiments of sponge structures can have, e.g., 90% or more, 75% or more, 50% or more (i.e., a majority), less than 50% (i.e., a minority), 25% or less, or 10% or less open cells, to name a few examples. Dimensions of the cells can vary widely based on the needs of the application. For example, in FIG. 12D cells 12004, 12005, and 12006 have lateral dimensions of approximately 14.9 microns, 12.3 microns, and 13 microns, respectively. In general, sponge cells for use as seals have lateral dimensions of between 0.1 and 1000 microns, or more preferably 1 and 100 microns, and still more preferably greater than or equal to 12 microns.

FIGS. 13A-D depict a surgical valve 13000 having a sewing cuff 13002 extending about the outer periphery of the valve's support structure 13004. The sewing cuff is a sponge or sponge-like polymer, specifically a SiPUU. The sewing cuff was pre-manufactured and attached by first applying wet polymer to the support structure exterior and then applying the sewing cuff, such that upon curing of the polymer the sewing cuff is attached (bonded polymerically) to dip-cast polymer of the support structure by way of the removed solvent (e.g., dMAC). The bond strength can be controlled by the ratio of polymer to solvent and the amount of pressure applied to the structures during curing.

Figure 14:
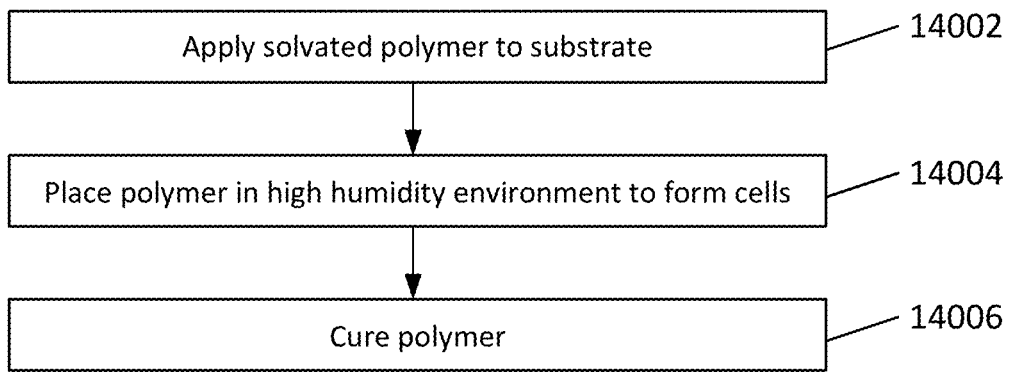
FIGS. 14-16 are flow diagrams depicting example embodiments of methods of fabricating a sponge-like polymer.
Figure 15:
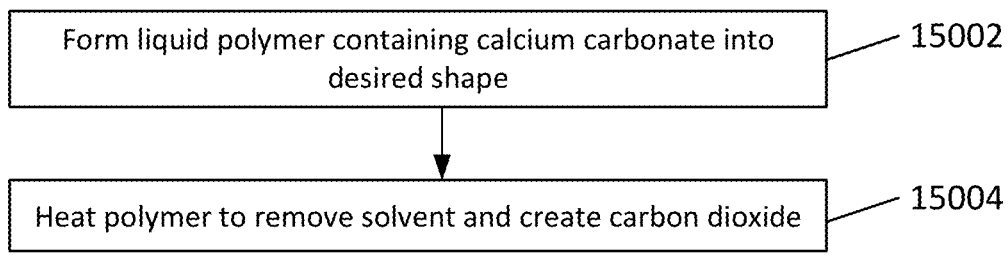
Figure 16:
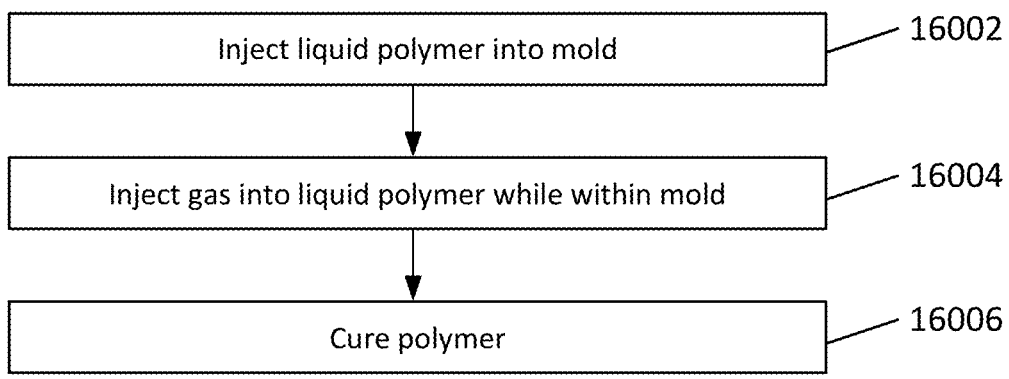

FIGS. 14-16 are flow diagrams depicting example embodiments of manufacturing sponge and sponge-like materials 12000. FIG. 14 depicts an example process 14000. At 14002, a solvated liquid polymer is applied to a substrate (e.g., a frame), for example by dipping or spraying, and that substrate is then placed into a relatively high humidity environment at 14004. Examples of high humidity environments are described in Int'l Publ. No. WO2019/028374, which is incorporated by reference herein in its entirety and for all purposes. After an extended period of time, the solvent (e.g., dimethylacetamide (DMAc)) in the polymer interacts with the water of the high humidity atmosphere and binds with water molecules, creating nascent cells. The solvent continues to draw water into the polymer and as a result the cells grow in size and the polymer swells. At 14006, the solvent and water is removed through a curing process, and the cavities left behind that were occupied by the solvent and water becomes a cellular structure as described herein. The cell size can be tailored by varying the humidity levels and pressure in the high humidity chamber.

FIG. 15 is a flow diagram depicting an example embodiment of a process 15000 for manufacturing a sponge or sponge-like material, where the process utilizes a solvated polymer with calcium carbonate ($CaCO_3$) dispersed therein. At 15002 the polymer is formed into the desired shape, such as by molding in a mold, dipping or spraying onto a substrate, or otherwise. At 15004 the solvated polymer is heated to remove the solvent (e.g., DMAc). This heating also causes the calcium carbonate to break down into gaseous carbon dioxide ($CO_2$) and calcium oxide (CaO). The carbon dioxide bubbles in the polymer like a foam, and upon curing at 15006 results in an at least partially open cell structure.

FIG. 16 is a flow diagram depicting an example embodiment of a process 16000 for manufacturing a sponge-like polymer utilizing the injection of gas. At 16002 the liquid polymer is injected into a mold having the desired shape.

Then at 16004 gas ports located along the sides mold are used to inject gas (e.g., nitrogen ($N_2$)) from a gas container into the liquid polymer within the mold. This creates small gas bubbles within the liquid polymer. The liquid polymer is then cured within the mold at 16006, forming a sponge-like structure of the desired shape.

In another embodiment, the sponge-like polymer can be formed from a liquid polymer that includes water soluble microparticles (e.g., polyethylene oxide (PEO)) that create controlled voids in the polymer when exposed to water.

Example Embodiments of Utilizing Sponge-Like or Latticed Materials for Carrying Agents In all of the embodiments described herein, materials with a sponge-like and/or latticed structure can be configured to carry one or more agents, such as a drug or other therapeutic agent, for release into the patient's body. The agent(s) can be applied into the sponge-like or latticed structure during manufacturing of the structure itself, or after manufacturing of the structure. The agent can be carried in solid, gel, or liquid form. Upon introduction to the body, the agent can be released into the bloodstream and/or surrounding tissue. The agent can have any desired effect, such as the promotion of tissue in-growth, the prevention or facilitation of thrombus formation or healing response, the reduction of inflammation, and the like. A non-exhaustive list of drugs for promoting tissue in-growth includes Fibronectin and bone morphogenic protein (BMPs). A non-exhaustive list of drugs for preventing thrombosis (anticoagulant) includes Warfarin (Coumadin), Heparin, and Lovenox. The agent can be configured to dissolve in a time-release fashion. For drug elution, the rate of uptake is generally dependent on the surface area, among other factors.

Polymer Crimpability

Another aspect of a preferred embodiment is the use of crimpable polymer structures. For instance, the number of frame cells is inversely related to crimpability (e.g., 24-cell design does not crimp as well as a 12-cell design). The use of a polymer on the outer diameter (OD) of the frame can crimp—as polymer moves within the wall of the frame, the crimpability goes down. It is further noted that the thickness of the polymer within each frame cell has a direct correlation to crimpability. Moreover, generally, polymer can be more aggressively crimped without damage than tissue.

Figures 17A, 17B:
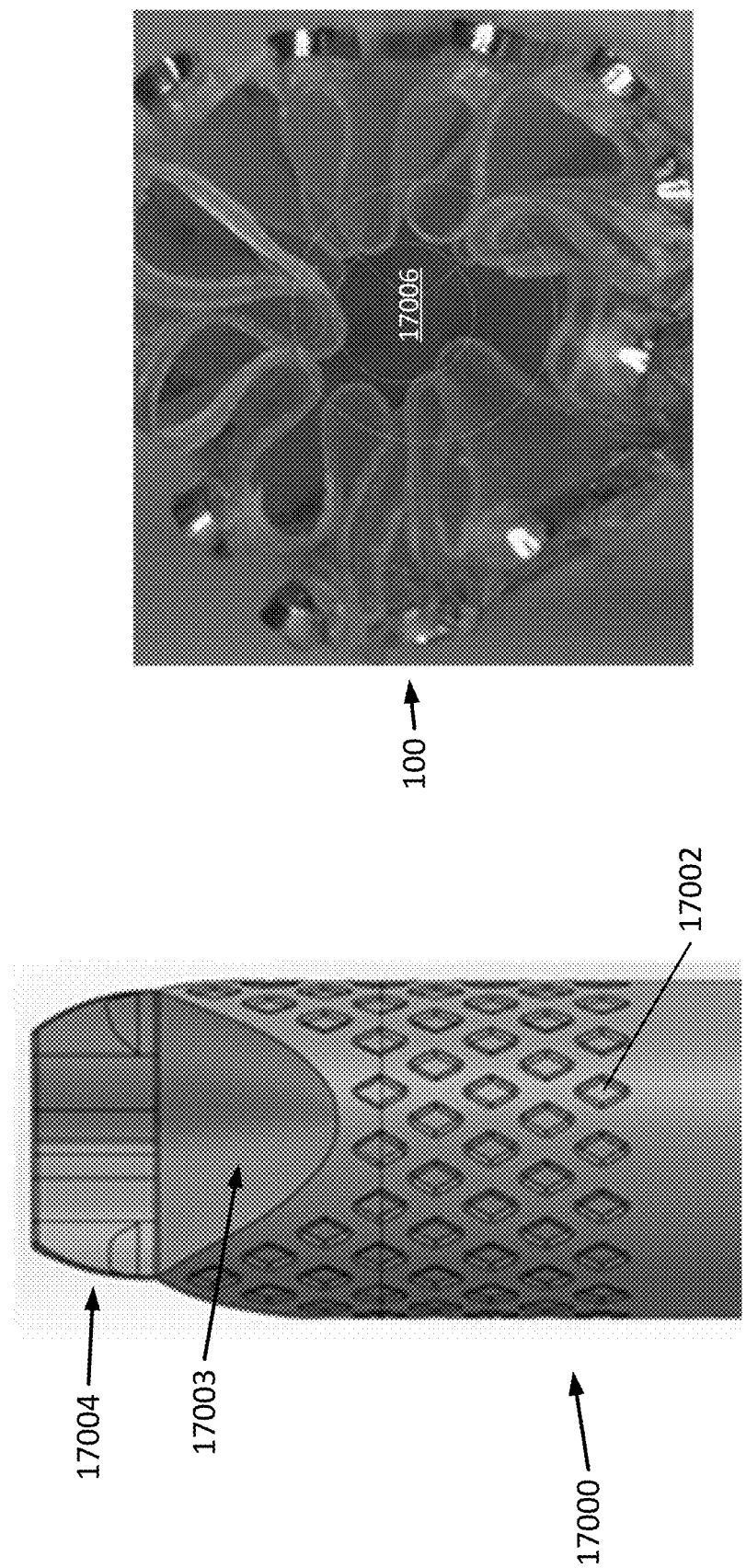
FIG. 17A is a side view of an example embodiment of a mandrel.
FIG. 17B is a top down view of an example embodiment of a valve in a crimped state.

FIG. 17A is a side view of a mandrel 17000 (or mold or former) having multiple recesses or indentations 17002 to assist the crimping of a valve having polymer adjacent to the cells of the frame (not shown). Mandrel 17000 also has a region 17003 for leaflet formation and a region 17004 to assist in polymer drain off after dipping. Mandrel 17000 is configured such that, when the frame is placed over mandrel 17000, each cell of the frame has a corresponding indentation 17002, where the indentation has a size and shape that matches (or is slightly smaller than) the interior region of the cell. When mandrel 17000 is dipped in polymer (either with or without the frame located thereon), the polymer fills indentations 17002. When the prosthesis is finally assembled, the polymer from the indentations, in the interior regions of cells, will be biased towards the inner diameter of the prosthesis. Thus, when the prosthesis is in the expanded state and is transitioned towards the crimped state, the polymer will tend to move towards and into the interior diameter of the prosthesis.

FIG. 17B is a photograph depicting an example of a valve 100 in a crimped state, where the polymer leaflets and polymer from the interior regions of the cells has moved into and is located within the inner lumen 17006 of the crimped valve. Use of mandrel 17000 has been found to reduce the diameter of a crimped valve 100 by up to 3 French. For example, a valve fabricated using mandrel 17000 was crimped to 19 French, and a similar valve fabricated with a mandrel not having indentations 17002 crimped to only 22 French. Mandrel 17000 can be configured for use in the formation of all embodiments of valves described herein, including valves having different shaped frames (such as with or without a crown) and valves formed via dipping and/or electrospinning.

FIGS. 18A-18B are used to described another feature that can enhance crimpability, which may be used in all embodiments herein that are susceptible to polymer pooling in cell apices, and which feature can be used instead of or in addition to the feature of FIGS. 17A-17B. Frames dipped in polymer, either to coat the frame struts while leaving the cell space open, or to fill the cell, are susceptible to polymer accumulation or pooling at the apices of the frame cells, where most compression occurs when entering the crimped or contracted state.

FIG. 18A depicts a first embodiment of a portion of a frame 18000 in an expanded state, and FIG. 18B depicts a second embodiment of a portion of frame 18000 in a crimped state. An interior region 18001-1 of a first cell is shown bordered by two struts 18002-1 and 18002-3. An interior region 18001-2 of a second cell is shown bordered by two struts 18002-2 and 18002-4. Struts 18002-1 and 18002-2 intersect at apex junction 18006, and are curved to form a pocket 18004-1 where polymer can accumulate or well. A similar pocket 18004-2 is shown at the intersection of struts 18002-3 and 18002-4. Pockets 18004 are positioned at each upper and lower apex of each frame cell where the polymer is subject to pooling and the most compression in crimping. Pockets 18004 alleviate some of this compression by providing additional space for the polymer to occupy during crimping, as seen in FIG. 18B, and thus a reduced diameter crimped state is achievable. In the embodiment of FIG. 18B, struts 18002 have a generally uniform width along their length. In the embodiment of FIG. 18A, struts 18002 taper down from a maximum width to a thinner width along the periphery of pocket 18004, which is shown partially filled with polymer.

In all of the embodiments described herein, polymers having different characteristics can be used. These characteristics can include viscosity, chemical composition, the presence of additives, and the like.

The embodiments of valve described herein are trileaflet (three leaflet) valves, although valve can be implemented and manufactured as a bileaflet (two leaflet) valve in the alternative. Upon review of the present document, those of ordinary skill in the art will readily recognize how to implement and manufacture valve as a bileaflet valve without requiring such to be shown in a figure.

Other Medical Devices

The embodiments described herein are not limited to use with valves. These embodiments or aspects of these embodiments can be applied to other medical devices as well. For example, the SiPUU polymers described herein can be used with any medical device, with a uniform solid structure devoid of gaps (e.g., not latticed and not sponge-like) or in a latticed and/or sponge-like structure. For example, sponge-like polymers can be used in replacement discs or vertebrae. In such embodiments a relatively high porosity is desirable to provide more mechanical support and less compressibility. For example, an 80% or higher porosity would help osteoblasts anchor to the implant.

Sponge-like polymers can also be used in tissue (graft) scaffold devices and frames. Sponge-like polymers can be used in vascular patches, where high porosity ensures the cells are interconnected. For example, lateral dimension sizes for jugular patches in the range of 4-6 microns are desirable.

Sponge-like polymers can also be used for vascular filters (e.g., inferior vena cava filters, embolic protection devices), for removing potential thrombi from the bloodstream. In such applications a high porosity is desirable to permit blood to flow through the sponge while still capturing other bodies. A cell (or pore) cross-sectional area of approximately 25×25 square microns or greater would permit red blood cells (8.2×2.5 square microns) and white blood cells to pass. The cell size for such applications depends on the intended placement location of the filter as the pressures dictate the ideal size and porosity (an IVC filter has different constraints than an embolic protection device).

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many embodiments, a first implantable valve can include: a frame and a polymeric valvular body. The frame can include a plurality of deflectable struts, an upstream end, a downstream end and a waist area in between the downstream and upstream ends. The polymeric valvular body is coupled with the frame and includes a plurality of artificial leaflets, where the frame defines a plurality of commissure positions, and the plurality of deflectable struts at the downstream end define a crown shape in between the plurality of commissure positions.

In some embodiments, the polymer of the valvular body can be a siloxane polyurethane urea.

In some embodiments, the implantable valve can include at least one open region defined in the waist area and has a length and width extended across multiple deflectable struts.

In some embodiments, the frame can have three commissure positions, each positioned near an artificial leaflet.

In some embodiments, the frame and valvular body can be coupled together with cured polymer in either film or fiber form.

In some embodiments, the frame can be encapsulated in the cured polymer in either film or fiber form.

In some embodiments, the polymeric valvular body can be made of cured polymer in either film or fiber form.

In some embodiments, the implantable valve can have a longitudinal axis and, when the implantable valve is in the expanded state, the plurality of deflectable struts are transverse to the longitudinal axis. When in a fully contracted state, the plurality of deflectable struts can be parallel or substantially parallel to the longitudinal axis.

In some embodiments, the plurality of deflectable struts can intersect and form a plurality of cells. The apex of each cell can have a pocket filled with polymer. The plurality of deflectable struts can be curved at the position of each pocket. The curved portions of the plurality of deflectable struts can be relatively thinner that straight portions of the plurality of deflectable struts.

In some embodiments, the valvular body can include a skirt located upstream from an upstream end of the frame. The skirt can extend over the upstream end of the frame. The skirt can also extend over an exterior upstream portion of the frame. The skirt can also extend over the exterior upstream portion of the frame and is not bonded to the exterior upstream portion of the frame. The skirt can be made of a polymer that is the same as the valvular body. The skirt can also be made of a polymer that is different from the polymer of the valvular body. The skirt can have an inflow edge portion that is covered with a polymer coating, which can cover only the inflow edge portion. The skirt can also have an outflow edge portion that is fused to an underlying polymer.

In some embodiments, the plurality of deflectable struts can define cells filled with polymer, where the polymer can be biased to deflect from within the cells into an inner lumen of the valve upon transitioning from an expanded state to a contracted state.

In some embodiments, the frame can include a primary structure with a secondary structure coated over the primary structure.

In some embodiments, the implantable valve can have a radial dimension and can be transitionable between a contracted state and an expanded state, where the radial dimension is relatively smaller in the contracted state than in the expanded state.

In some embodiments, a second example implantable valve can include a frame and a polymeric valvular body. The frame can include a plurality of deflectable struts, an upstream end, a downstream end, and a waist area in between the downstream and upstream ends. The polymeric valvular body can be coupled with the frame, the polymeric valve body can include a plurality of artificial leaflets. The frame can define a plurality of commissure positions, and the plurality of deflectable struts at the downstream end can define a continuous edge in between the plurality of commissure positions.

In some embodiments, the implantable valve can further include a strut formed with a deflection attenuation configuration on the downstream end of each of the plurality of commissure positions.

In some embodiments, the strut formed with a deflection attenuation configuration on the downstream end of each of the plurality of commissure positions can have a T-shape.

In some embodiments, the frame can have three commissure positions, each positioned near an artificial leaflet.

In some embodiments, the frame and valvular body can be coupled together with cured polymer in either film or fiber form.

In some embodiments, the frame can be encapsulated in the cured polymer in either film or fiber form.

In some embodiments, the polymeric valvular body can be composed of the cured polymer in either film or fiber form.

In some embodiments, the implantable valve can have a longitudinal axis and, when the implantable valve is in the expanded state, the plurality of deflectable struts are transverse to the longitudinal axis.

In some embodiments, when in a fully contracted state, the plurality of deflectable struts can be parallel or substantially parallel to the longitudinal axis.

In some embodiments, the plurality of deflectable struts cross and form a plurality of cells.

In some embodiments, the valvular body can include a skirt located upstream from an upstream end of the frame. The skirt can extend over the upstream end of the frame. The skirt can also extend over an exterior upstream portion of the frame. The skirt can also extend over the exterior upstream portion of the frame and is not bonded to the exterior upstream portion of the frame. The skirt can be made of a polymer that is the same as the valvular body. The skirt can be made of a polymer that is different from the polymer of the valvular body. The skirt can have an inflow edge portion that is covered with a polymer coating, which can cover only the inflow edge portion. The skirt can have an outflow edge portion that is fused to an underlying polymer.

In some embodiments, the plurality of deflectable struts can intersect and form a plurality of cells. The apex of each cell can have a pocket filled with polymer. The plurality of deflectable struts can be curved at the position of each pocket. The curved portions of the plurality of deflectable struts can be relatively thinner than straight portions of the plurality of deflectable struts.

In some embodiments, the plurality of deflectable struts can define cells filled with polymer, where the polymer is biased to deflect from within the cells into an inner lumen of the valve upon transitioning from an expanded state to a contracted state.

In any of the above embodiments, plurality of leaflets can be two or three leaflets.

In any of the above embodiments, the implantable valve can replace an aortic valve of a human heart.

In some embodiments, a first example method of manufacturing an implantable valve can include: forming a polymeric valvular body; forming and crimping a frame; dipping the crimped frame in wet polymer; positioning the polymeric valvular body over the crimped frame; and uncrimping the frame.

In some embodiments, forming the polymeric valvular body can include: dipping a mold in wet polymer to form a polymer coating on the mold; and allowing the polymer coating on the mold to cure.

In some embodiments, the mold can include a contoured surface to form the plurality of leaflets.

In some embodiments, the valvular body can be positioned over the frame such that the frame is aligned with a plurality of leaflets of the valvular body.

In some embodiments, the polymeric valvular body can be positioned over the frame such that commissure positions between adjacent leaflets of the polymeric valvular body are aligned with corresponding positions on the frame.

In some embodiments, the valvular body can include a plurality of leaflets, and the upstream portion of the frame and polymeric valvular body are dipped in wet polymer such that the polymer coating is placed on the upstream portion and not on the plurality of leaflets.

In some embodiments, allowing the polymer coating to cure can include allowing the polymer coating to cure while an upstream end of the valvular body is facing downward.

In some embodiments, the implantable valve can be formed after allowing the polymer coating to cure or after performing valve finishing to the frame or valvular body.

In some embodiments, a method of manufacturing an implantable valve can include: forming a polymeric valvular body; dipping a frame in wet polymer; positioning the frame over the polymeric valvular body; and applying radial compression to the frame.

In some embodiments, forming the polymeric valvular body can include: dipping a mold in wet polymer to form a polymer coating on the mold; and allowing the polymer coating on the mold to cure.

In some embodiments, the mold can include a contoured surface to form the plurality of leaflets.

In some embodiments, the frame can be positioned over the valvular body such that the frame can be aligned with a plurality of leaflets of the valvular body.

In some embodiments, the frame can be positioned over the polymeric valvular body such that commissure positions between adjacent leaflets of the polymeric valvular body are aligned with corresponding positions on the frame.

In some embodiments, the valvular body can include a plurality of leaflets, and the upstream portion of the frame and polymeric valvular body are dipped in wet polymer such that the polymer coating is placed on the upstream portion and not on the plurality of leaflets.

In some embodiments, allowing the polymer coating to cure can include allowing the polymer coating to cure while an upstream end of the valvular body is facing downward.

In some embodiments, the implantable valve can be formed after allowing the polymer coating to cure or after performing valve finishing to the frame or valvular body.

In many embodiments, a method of manufacturing an implantable valve can include placing a frame on a mold of a valvular body; and dipping the frame and mold in wet polymer to form a polymer coating; and curing the polymer.

In some embodiments, the mold can include a contoured surface to form the plurality of leaflets.

In some embodiments, the valvular body can be positioned over the frame such that the frame is aligned with a plurality of leaflets of the valvular body.

In some embodiments, the polymeric valvular body can be positioned over the frame such that commissure positions between adjacent leaflets of the polymeric valvular body are aligned with corresponding positions on the frame.

In some embodiments, the valvular body can include a plurality of leaflets, and the upstream portion of the frame and polymeric valvular body are dipped in wet polymer such that the polymer coating is placed on the upstream portion and not on the plurality of leaflets.

In some embodiments, allowing the polymer coating to cure can include allowing the polymer coating to cure while an upstream end of the valvular body is facing downward.

In some embodiments, the implantable valve can be formed after allowing the polymer coating to cure or after performing valve finishing to the frame or valvular body.

In some embodiments, the mold can include a plurality of indentations, each indentation having a position that corresponds to an interior region of a cell of the frame.

In some embodiments, each indentation can have a shape that corresponds to the interior region of a cell of the frame.

In many embodiments, a method of manufacturing an implantable valve can include: electrospinning a polymeric valvular body onto a mandrel; placing a frame over the valvular body; and electrospinning a skirt over the frame.

In some embodiments, the valvular body can be formed by wet electrospinning.

In some embodiments, the skirt can be formed by dry electrospinning.

In some embodiments, the valvular body can be formed of a first polymer and the skirt is formed of a second polymer.

In some embodiments, the skirt can be formed of a first polymer and a second polymer.

In some embodiments, the mold can include a contoured surface to form the plurality of leaflets.

In some embodiments, the frame can be positioned over the valvular body such that the frame is aligned with a plurality of leaflets of the valvular body.

In some embodiments, the frame can be positioned over the polymeric valvular body such that commissure positions between adjacent leaflets of the polymeric valvular body are aligned with corresponding positions on the frame.

In some embodiments, the method can further include conditioning an outflow edge and/or an inflow edge of the skirt. Conditioning the inflow edge of the skirt can include dipping only an inflow edge region of the skirt in polymer.

Conditioning the outflow edge of the skirt can also include fusing the outflow edge to an underlying polymer.

In many embodiments, an implantable valve can include: a support structure; a plurality of leaflets coupled with the support structure; and a sponge-like polymeric material coupled with the support structure.

In some embodiments, the sponge-like polymeric material can include a plurality of cells. The sponge-like polymeric material can include a first substance, and interiors of the plurality of cells can include a second substance different than the first substance. The second substance can be a solid, liquid, or gas. The second substance can be a gas, and the sponge-like polymeric material can be compressible. The second substance can be a therapeutic agent. The majority of the plurality of cells can have cross-sectional dimension in the range of 0.1 and 1000 microns.

In some embodiments, the sponge-like polymeric material can form a sewing cuff or seal coupled with the support structure.

In some embodiments, the sponge-like polymeric material can form a sewing cuff located about an outer periphery of the support structure, and configured to allow passage of a filament therethrough to couple that support structure to adjacent tissue.

In some embodiments, the sponge-like polymeric material can form a seal located about an outer periphery of the support structure, wherein the seal is configured to mitigate paravalvular leakage. The support structure can be radially compressible or radially collapsible for intravascular implantation. The support structure can also be radially compressible or radially collapsible for placement in an intravascular delivery device. The support structure can be self-expandable or balloon expandable. The seal can be a sealing skirt and the support structure can be a frame. The sealing skirt can be located upstream from an upstream end of the frame. The sealing skirt can extend over the upstream end of the frame. The skirt can also extend over an exterior upstream portion of the frame. The skirt can also extend over the exterior upstream portion of the frame and is not bonded to the exterior upstream portion of the frame.

In some embodiments, the plurality of leaflets and the sponge-like polymer are polymeric and can be the same polymer.

In any of the above embodiments, the implantable valve can be made to replace an aortic valve of a human heart.

In any of the above embodiments, the plurality of leaflets can be two or three leaflets.

In some embodiments, the plurality of cells each can include a therapeutic agent.

In some embodiments, the sponge-like polymer can be compressible.

In some embodiments, the sponge-like polymer can be porous or semi-porous.

In some embodiments, the sponge-like polymer can be used as a seal of a heart valve.

In many embodiments, a method of manufacturing a sponge-like polymer can include: applying a liquid polymer comprising a solvent to a substrate; exposing the substrate to a humid atmosphere such that the solvent binds with water molecules and form cells; and curing the polymer to remove the solvent and water, such that the polymer retains a sponge-like structure.

In some embodiments, the polymer can be a siloxane polyurethane urea.

In some embodiments, the substrate can be a support structure of a valve.

In many embodiments, a method of manufacturing a sponge-like polymer can include: forming a liquid polymer comprising calcium carbonate into a shape; heating the liquid polymer such that the calcium carbonate produces gaseous bubbles in the liquid polymer; and curing the polymer such that the polymer retains a sponge-like structure.

In some embodiments, the liquid polymer can be heated such that the solvent is removed.

In some embodiments, the gaseous bubbles can be carbon dioxide bubbles.

In some embodiments, polymer can be a siloxane polyurethane urea.

In many embodiments, a method of manufacturing a sponge-like polymer can include: placing liquid polymer into a mold, wherein a sidewall of the mold can include gas ports; injecting gas through the gas ports and into the liquid polymer such that bubbles are formed in the liquid polymer; curing the polymer such that the polymer retains a sponge-like structure.

In some embodiments, the gas can be nitrogen, and the polymer is a siloxane polyurethane urea.

In many embodiments, a method of manufacturing a heart valve can include: electrospinning a polymer onto a support structure of the valve, where the electrospun polymer has a latticed or fibrous structure.

In some embodiments, the electrospinning process can be a dry electrospinning process.

In some embodiments, the electrospun polymer can be in the shape of a seal about a periphery of the support structure.

In some embodiments, the seal can be a sealing skirt or a sewing cuff.

In some embodiments, the method of manufacturing a heart valve can further include embedding a therapeutic agent in the latticed structure.

In some embodiments, the electrospun polymer can be compressible.

In some embodiments, the support structure can be a radially compressible frame or a non-radially compressible structure.

In some embodiments, the electrospun polymer can be a siloxane polyurethane urea.

In some embodiments, the electrospun polymer can forms leaflet of the heart valve.

In many embodiments, a method of manufacturing a heart valve can include electrospinning a polymer and coupling the electrospun polymer to a support structure of a valve, where the electrospun polymer can have a latticed or fibrous structure.

In some embodiments, the electrospinning process is a dry electrospinning process.

In some embodiments, the electrospun polymer is in the shape of a seal about a periphery of the support structure.

In some embodiments, the method of manufacturing the heart valve can further include embedding a therapeutic agent in the latticed structure.

In some embodiments, the electrospun polymer can be compressible.

In some embodiments, the coupling the electrospun polymer to the support structure of the valve can include applying liquid polymer to the support structure and placing the electrospun polymer on the applied liquid polymer such that curing of the polymer couples the electrospun polymer to the support structure.

In some embodiments, the polymer can be a siloxane polyurethane urea.

In some embodiments, the electrospun polymer can form leaflets of the valve.

In many embodiments, a method of manufacturing a heart valve can include electrospinning a valvular body onto a mandrel; placing a frame over the valvular body; and electrospinning a polymeric layer over the frame to bond the frame to the valvular body through openings in the frame, where the polymeric layer forms a sealing skirt.

In some embodiments, a wet-spinning process is used to electrospun the valvular body onto the mandrel.

In some embodiments, the method of manufacturing the heart valve can further include curing the valvular body prior to placing the frame over the valvular body.

In some embodiments, the method of manufacturing the heart valve can further include curing the polymeric layer.

In some embodiments, the method of manufacturing the heart valve can further include finishing the heart valve.

In some embodiments, the method of manufacturing the heart valve can further include removing the heart valve from the mandrel by cooling or heating the mandrel.

In many embodiments, a method of manufacturing a heart valve can include: electrospinning a valvular body onto a mandrel; placing a frame over the valvular body; and applying a polymeric layer over the frame to bond the frame to the valvular body through openings in the frame.

In some embodiments, a wet-spinning process can be used to electrospun the valvular body onto the mandrel.

In some embodiments, the method of manufacturing the heart valve can further include curing the valvular body prior to placing the frame over the valvular body.

In some embodiments, the method of manufacturing the heart valve can further include curing the polymeric layer.

In some embodiments, the method of manufacturing the heart valve can further include electrospinning a sealing skirt onto the frame and/or polymeric layer.

In some embodiments, the method of manufacturing the heart valve can further include curing the heart valve.

In some embodiments, the method of manufacturing the heart valve can further include finishing the heart valve.

In some embodiments, the method of manufacturing the heart valve can further include removing the heart valve from the mandrel by cooling or heating the mandrel.

In many embodiments, a method of manufacturing a heart valve can include: forming a valvular body on a first mandrel; placing a frame over the valvular body; and electrospinning polymer onto the frame to bond the frame to the valvular body.

In some embodiments, the method of manufacturing the heart valve can further include electrospinning a sealing skirt onto the frame and/or electrospun polymer.

In some embodiments, the method of manufacturing the heart valve can further include curing the sealing skirt. A wet-spinning process can be used to electrospin the polymer to bond the frame and/or to electrospin the sealing skirt. Forming the valvular body can include dipping the mandrel into liquid polymer and curing the liquid polymer.

In many embodiments, a method of manufacturing a heart valve can include: dipping a frame in liquid polymer to create a substrate on an inflow side of the frame; applying a sealing skirt over the substrate on the frame; dipping the frame in liquid polymer to form leaflets; and curing the heart valve.

In some embodiments, the method of manufacturing the heart valve can further include curing the polymer prior to applying the sealing skirt.

In some embodiments, the method of manufacturing the heart valve can further include curing the sealing skirt prior to dipping the frame in liquid polymer to form leaflets. The method of manufacturing the heart valve can further include trimming the sealing skirt.

In some embodiments, the frame can include a crown and open regions between the crown and a main body of the frame, where dipping the frame in liquid polymer to form leaflets can include dipping the frame with a shield over the open regions.

In some embodiments, the dipping the frame in liquid polymer to form leaflets can include dipping an outflow side of the frame up to and including an outflow edge of the sealing skirt.

In some embodiments, the method of manufacturing the heart valve can further include dipping an inflow edge of the sealing skirt in liquid polymer.

In some embodiments, the method of manufacturing the heart valve can further include trimming the leaflets.

In many embodiments, a method of manufacturing a valve prosthesis can include: electrospinning a polymer comprising solvent onto a frame and at least a portion of an at least partially cured polymeric valvular body; and curing the electrospun polymer such that a chemical bond is formed between the electrospun polymer and the polymeric valvular body.

In some embodiments, the electrospinning can be performed in an environment having a relative humidity of 60-100%.

In some embodiments, the electrospinning is performed in an environment having a temperature of 20 to 40 degrees Celsius.

In some embodiments, the method of manufacturing the valve prosthesis can further include removing electrospun polymer that did not contact the cured polymeric valvular body, which include at least two leaflets; and covering the leaflets, prior to electrospinning, to shield the leaflets from contact with electrospun polymer. Curing can be performed in an oven.

In some embodiments, the method of manufacturing the valve prosthesis can further include the following steps performed prior to electrospinning the polymer: dipping a mandrel in liquid polymer, wherein the mandrel has a surface contour for forming the valvular body with the plurality of leaflets; and at least partially curing the dipped polymer to form the valvular body.

In some embodiments, the method of manufacturing further includes placing the frame over the at least partially cured valvular body prior to electrospinning the polymer.

In some embodiments, the method of manufacturing the valve prosthesis can further include forming a sealing skirt on the valve prosthesis.

In some embodiments, the method of manufacturing the valve prosthesis can further include electrospun polymer or the polymeric valvular body is a siloxane polyurethane urea.

In some embodiments, the electrospun polymer and the polymeric valvular body are both a siloxane polyurethane urea.

In some embodiments, the polymer of the valvular body can be a siloxane polyurethane urea. In all the aforementioned embodiments pertaining to a siloxane polyurethane urea, that siloxane polyurethane urea can include: a first, a second, a third, and a fourth segment. The first segment can have a structure of $-A^1-L^1-A^1-$, where $L^1$ is the residue of a first diisocyanate. $A^1$ is the residue of a poly($C_1$-$C_{12}$alkane diol). The second segment can have the residue of a first siloxane-containing diol. The third segment can have the residue of a second siloxane-containing diol, and the fourth segment can have the residue of a $C_1$-$C_{12}$alkane diamine, where the segments are each covalently bonded to each other through the residue of a diisocyanate.

In all of the aforementioned embodiments, the valve can be configured as a mitral or aortic valve.

In all the aforementioned embodiments pertaining to a siloxane polyurethane urea, that siloxane polyurethane urea can have a structure of $A^4$-$L^4$-$A^3$-$L^3$-$A^2$-$L^2$-$A^1$-$L^1$-$A^1$-$L^2$-$A^2$-$L^3$-$A^3$-$L^4$-$A^4$, where $L^1$ can be the residue of a first diisocyanate. $A^1$ can be the residue of a poly($C_1$-$C_{12}$alkane diol). $L^2$ can be the residue of a second diisocyanate. $A^2$ can be selected from -$A^1$-$L^1$-$A^1$-, the residue of a first siloxane-containing diol, the residue of a second siloxane containing diol, and the residue of a $C_1$-$C_{12}$alkane diamine. $L^3$ can be the residue of a third diisocyanate. $A^3$ can be selected from the residue of a first siloxane-containing diol, the residue of a second siloxane containing diol, and the residue of a $C_1$-$C_{12}$alkane diamine. $L^4$ can be the residue of a fourth diisocyanate. $A^4$ can be selected from -$A^1$-$L^1$-$A^1$-, the residue of a first siloxane-containing diol, the residue of a second siloxane containing diol, and the residue of a $C_1$-$C_{12}$alkane diamine. In the structure of $A^4$-$L^4$-$A^3$-$L^3$-$A^2$-$L^2$-$A^1$-$L^1$-$A^1$-$L^2$-$A^2$-$L^3$-$A^3$-$L^4$-$A^4$, at least one instance of $A^2$, $A^3$, or $A^4$ can be the residue of a second siloxane containing diol; and at least one instance of $A^2$, $A^3$, or $A^4$ can be the residue of a $C_1$-$C_{12}$alkane diamine.

In all the aforementioned embodiments pertaining to a siloxane polyurethane urea, that siloxane polyurethane urea can include: a first structure of A $A^2$-$L^3$-$A^3$-$L^4$-$A^4$ (Formula II), and/or a second structure of $A^4$-$L^4$-$A^2$-$L^3$-$A^3$-$L^2$-$A^1$-$L^1$-$A^1$-$L^2$-$A^3$-$L^3$-$A^2$-$L^4$-$A^4$ (Formula III). For the first and second structures:

$L^1$ can be the residue of MDI;
$A^1$ can be the residue of PHMO;
$L^2$ can be the residue of MDI;
$A^2$ can be the residue of PDMS;
$L^3$ can be the residue of MDI;
$A^3$ can be the residue of BHTD;
$L^4$ can be the residue of MDI; and
$A^4$ can be the residue of EDA.

In many example embodiments, an implantable valve is provided that includes: a frame including a plurality of deflectable struts; and a polymeric valvular body coupled with the frame, the polymeric valve body including a plurality of artificial leaflets, where the implantable valve has a radial dimension and is transitionable between a contracted state and an expanded state, where the radial dimension is relatively smaller in the contracted state than in the expanded state.

In these valve embodiments, the frame and valvular body can be coupled together with cured polymer. The frame can be encapsulated in the cured polymer. The polymeric valvular body can be composed of the cured polymer.

In these valve embodiments, the implantable valve can have a longitudinal axis and, when the implantable valve is in the expanded state, the plurality of deflectable struts are transverse to the longitudinal axis. When in a fully contracted state, the plurality of deflectable struts can be parallel or substantially parallel to the longitudinal axis. The valve can further include a plurality of longitudinal struts, each of the plurality of longitudinal struts positioned at a commissure between adjacent leaflets. Each of the plurality of longitudinal struts can be parallel to a longitudinal axis of the implantable valve when the implantable valve is in the expanded and contracted configurations. The plurality of deflectable struts can cross and form a plurality of cells. The frame can include a first row of cells located adjacent a downstream end of the frame, where the plurality of longitudinal struts are in the first row of cells. The frame can include a second row of cells located upstream of the first row of cells, where no longitudinal strut is in the second row of cells.

In these valve embodiments, the valvular body can include a skirt located upstream from an upstream end of the frame. The skirt can extend over the upstream end of the frame. The skirt can extend over an exterior upstream portion of the frame. The skirt can extend over the exterior upstream portion of the frame and can be unconnected (not bonded) to the exterior upstream portion of the frame.

In these valve embodiments, the plurality of leaflets can be two and only two leaflets, or the plurality of leaflets can be three and only three leaflets. Other numbers of leaflets can also be used. In these valve embodiments, the implantable valve can be configured to replace an aortic valve of a human heart. In these valve embodiments, the implantable valve can be configured to replace a mitral, tricuspid, and pulmonic valves of a human heart. In these valve embodiments, the frame can include a primary structure with a secondary structure coated over the primary structure.

In many example embodiments, methods of implanting a prosthetic valve are provided, where the methods include: moving the prosthetic valve, with an elongate delivery device while the prosthetic valve is in a contracted state, through a body of a recipient; and implanting the prosthetic valve in the body of the recipient by, at least, deploying the prosthetic valve from the delivery device, where the prosthetic valve is implanted in an expanded configuration, and where the prosthetic valve is in accordance with any of the aforementioned valve embodiments.

As used herein and in the appended claims, the singular forms "a", "an", and "the" include plural referents unless the context clearly dictates otherwise.

Where a range of values is provided, each intervening value, to the tenth of the unit of the lower limit unless the context clearly dictates otherwise, between the upper and lower limit of that range and any other stated or intervening value in that stated range, is encompassed within the disclosure and can be claimed as a sole value or as a smaller range. Where the stated range includes one or both of the limits, ranges excluding either or both of those included limits are also included in the disclosure.

Where a discrete value or range of values is provided, that value or range of values may be claimed more broadly than as a discrete number or range of numbers, unless indicated otherwise. For example, each value or range of values provided herein may be claimed as an approximation and this paragraph serves as antecedent basis and written support for the introduction of claims, at any time, that recite each such value or range of values as "approximately" that value, "approximately" that range of values, "about" that value, and/or "about" that range of values. Conversely, if a value or range of values is stated as an approximation or generalization, e.g., approximately X or about X, then that value or range of values can be claimed discretely without using such a broadening term.

However, in no way should this specification be interpreted as implying that the subject matter disclosed herein is limited to a particular value or range of values absent explicit recitation of that value or range of values in the claims. Values and ranges of values are provided herein merely as examples.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An implantable prosthetic heart valve, comprising:
an expandable support structure comprising a frame having a plurality of deflectable struts forming multiple rows of cells interconnected in a lattice, an upstream end embedded in polymer, a downstream end embedded in polymer, wherein the interconnected cells in the lattice form a continuous edge along the multiple rows of cells interconnected in the lattice and angled between the upstream end the downstream end, and an electrospun polymer sealed about a periphery of the support structure; and
a polymeric valvular body comprising a plurality of artificial leaflets formed from a cured polymer, coupled with and contoured to the frame between the upstream end embedded in polymer and the downstream end embedded in polymer and, encapsulating the lattice in the cured polymer and wherein the downstream ends of the leaflets engage the continuous edge along a length thereof;
wherein the frame defines a plurality of commissure positions and a plurality of deflectable struts at the downstream end forming a crest offset from the plurality of commissure positions,
wherein the electrospun polymer of the support structure comprises a skirt located upstream from an upstream end of the frame; and
wherein the skirt has an outflow edge portion that is fused to the polymer in which the upstream end is embedded.

2. The implantable prosthetic heart valve of claim 1, wherein the polymer of the valvular body is a siloxane polyurethane urea.

3. The implantable prosthetic heart valve of claim 1, further includes a waist area containing multiple rows of cells within the waist area.

4. The implantable prosthetic heart valve of claim 1, wherein the upstream end of the frame is encapsulated in both a cured polymer and an electrospun polymer.

5. The implantable prosthetic heart valve of claim 1, wherein cells of the lattice adjacent the polymeric valve body are dip cast with the polymeric valvular body.

6. The implantable prosthetic heart valve of claim 1, wherein the implantable valve has a longitudinal axis and, when the implantable valve is in the expanded state, the plurality of deflectable struts are transverse to the longitudinal axis.

7. The implantable prosthetic heart valve of claim 6, wherein, when in a fully contracted state, the plurality of deflectable struts are parallel or substantially parallel to the longitudinal axis.

8. The implantable prosthetic heart valve of claim 1, wherein the plurality of deflectable struts intersect.

9. The implantable prosthetic heart valve of claim 1, wherein the plurality of deflectable struts are each coupled to an adjacent strut at a deformable location.

10. The implantable prosthetic heart valve of claim 1, further comprising a locking feature at the downstream end thereof.

11. The implantable prosthetic heart valve of claim 10, wherein the locking feature is a loop.

12. The implantable prosthetic heart valve of claim 1, wherein the skirt extends over an exterior upstream portion of the frame.

13. The implantable prosthetic heart valve of claim 1, wherein the skirt is made of a polymer that is the same as the valvular body.

14. The implantable prosthetic heart valve of claim 1, wherein the skirt is made of a polymer that is different from the polymer of the valvular body.

15. The implantable prosthetic heart valve of claim 1, wherein the skirt has an inflow edge portion that is covered with a polymer coating.

16. The implantable prosthetic heart valve of claim 15, wherein the polymer coating covers only the inflow edge portion.

17. The implantable prosthetic heart valve of claim 1, wherein portions of deflectable struts forming the downstream portion of the lattice are coupled to form a smaller cell therebetween.

* * * * *